(12) United States Patent
Giacomini et al.

(10) Patent No.: US 10,392,412 B2
(45) Date of Patent: Aug. 27, 2019

(54) PLATINUM ANTICANCER AGENTS

(71) Applicants: THE REGENTS OF THE UNIVERSITY OF CALIFORNIA, Oakland, CA (US); CORNELL UNIVERSITY, Ithaca, NY (US)

(72) Inventors: Kathleen M. Giacomini, Atherton, CA (US); Swati More, Minneapolis, MN (US); Sook Wah Yee, San Francisco, CA (US); Ethan Geier, San Francisco, CA (US); Justin Wilson, Ithaca, NY (US)

(73) Assignees: THE REGENTS OF THE UNIVERSITY OF CALIFORNIA, Oakland, CA (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/778,213

(22) PCT Filed: Nov. 2, 2016

(86) PCT No.: PCT/US2016/063408
§ 371 (c)(1),
(2) Date: May 22, 2018

(87) PCT Pub. No.: WO2017/091616
PCT Pub. Date: Jun. 1, 2017

(65) Prior Publication Data
US 2018/0346499 A1    Dec. 6, 2018

Related U.S. Application Data

(60) Provisional application No. 62/259,842, filed on Nov. 25, 2015.

(51) Int. Cl.
C07D 487/04 (2006.01)
C07F 15/00 (2006.01)
A61P 35/04 (2006.01)
A61K 33/24 (2019.01)

(52) U.S. Cl.
CPC .......... *C07F 15/0093* (2013.01); *A61K 33/24* (2013.01); *A61P 35/04* (2018.01); *C07D 487/04* (2013.01)

(58) Field of Classification Search
None
See application file for complete search history.

(56) References Cited

U.S. PATENT DOCUMENTS

2011/0284799 A1   11/2011  Stoessel et al.
2014/0057869 A9    2/2014  Christian

OTHER PUBLICATIONS

Al-Muhammed, J. et al. (May-Jun. 1996). "In-vivo studies on dexamethasone sodium phosphate liposomes," J Microencapsul 13(3):293-306.

Badagnani, I. et al. (Aug. 2006, e-published May 15, 2006). "Interaction of methotrexate with organic-anion transporting polypeptide 1A2 and its genetic variants," *J Pharmacol Exp Ther* 318(2):521-529.

Chonn, A. et al. (Dec. 1995). "Recent advances in liposomal drug-delivery systems," *Curr Opin Biotechnol* 6(6):698-708.

Covell, D.G. et al. (Aug. 2007). "Anticancer medicines in development: assessment of bioactivity profiles within the National Cancer Institute anticancer screening data," Mol Cancer Ther 6(8):2261-2270.

Diop-Bove, N.K. et al. (Aug. 2009, e-published Aug. 11, 2009). "Hypermethylation of the human proton-coupled folate transporter (SLC46A1) minimal transcriptional regulatory region in an antifolate-resistant HeLa cell line," *Mol Cancer Ther* 8(8):2424-2431.

Eyles, J.E. et al. (Jul. 1997). "Oral delivery and fate of poly(lactic acid) microsphere-encapsulated interferon in rats," J Pharm Pharmacol 49(7):669-674.

Gao, Z.H. et al. (Jun. 1995). "Controlled release of a contraceptive steroid from biodegradable and injectable gel formulations: in vitro evaluation," *Pharm Res* 12(6):857-863.

Leamon, C.P. et al. (Dec. 2008, e-published Sep. 12, 2008). "Impact of high and low folate diets on tissue folate receptor levels and antitumor responses toward folate-drug conjugates," *J Pharmacol Exp Ther* 327(3):918-925.

Lovejoy, K.S. et al. (Jul. 1, 2008, e-published Jun. 25, 2008). "cis-Diammine(pyridine)chloroplatinum(II), a monofunctional platinum(II) antitumor agent: Uptake, structure, function, and prospects," *PNAS USA* 105(26):8902-8907.

Mendelsohn, L.G. et al. (1996). "The role of dietary folate in modulation of folate receptor expression, folylpolyglutamate synthetase activity and the efficacy and toxicity of lometrexol," *Adv Enzyme Regul* 36:365-381.

More, S.S. et al. (Apr. 2010, e-published Apr. 6, 2010). "Organic cation transporters modulate the uptake and cytotoxicity of picoplatin, a third-generation platinum analogue," *Mol Cancer Ther* 9(4):1058-1069.

Ostro, M.J. et al. (Aug. 1989). "Use of liposomes as injectable-drug delivery systems," *Am J Hosp Pharm* 46(8):1576-1587.

PubChem-CID-58517492, Create Date Aug. 19, 2012, located at <https://pubchem.ncbi.nlm.nih.gov/compound/58517492#section=Top> 10 pages.

Raghunathan, K. et al. (1997). "Disposition of leucovorin and its metabolites in dietary folic acid—deplete mice—comparison between tumor, liver, and plasma," *Cancer Chemother Pharmacol* 40(2):126-130.

Rao, K.P. et al. (1995). "Recent developments of collagen-based materials for medical applications and drug delivery systems," *J Biomater Sci Polym Ed* 7(7):623-645.

Uwai, Y. et al. (Nov. 6, 1998). "Functional characterization of the rat multispecific organic anion transporter OAT1 mediating basolateral uptake of anionic drugs in the kidney," *FEBS Lett* 438(3):321-324.

Vitols, K.S. et al. (1987). "Platinum-folate compounds: synthesis, properties and biological activity," *Adv Enzyme Regul* 26:17-27.

International Search Report dated Feb. 1, 2017, for PCT Application No. PCT/US2016/063408, filed Nov. 22, 2016, 2 pages.

Worzalla, J.F. et al. (Sep.-Oct. 1998). "Role of folic acid in modulating the toxicity and efficacy of the multitargeted antifolate, LY231514," *Anticancer Res* 18(5A):3235-3239.

(Continued)

*Primary Examiner* — Nyeemah A Grazier
(74) *Attorney, Agent, or Firm* — Doris Lee; Mintz, Levin, Cohn, Ferris, Glovsky and Popeo, P.C.

(57) ABSTRACT

Disclosed herein, inter alia, are platinum-based compounds useful for treating cancer.

25 Claims, 14 Drawing Sheets

(56) References Cited

OTHER PUBLICATIONS

Written Opinion dated Feb. 1, 2017, for PCT Application No. PCT/US2016/063408, filed Nov. 22, 2016, 3 pages.

Zhang, S. et al. (Sep. 1, 2006). "Organic cation transporters are determinants of oxaliplatin cytotoxicity," *Cancer Res* 66(17):8847-8857.

Zhao, R. et al. (Dec. 15, 2004). "Antifolate resistance in a HeLa cell line associated with impaired transport independent of the reduced folate carrier," *Clin Cancer Res* 10(24):8735-8742.

Zhao, R. et al. (Sep. 2008, e-published Jun. 4, 2008). "The proton-coupled folate transporter: impact on pemetrexed transport and on antifolates activities compared with the reduced folate carrier," *Mol Pharmacol* 74(3):854-862.

trans cis

AT-69 and CP cause significant weight loss by day 12

AT-70 causes significant weight loss by day 5

PLATINUM ANTICANCER AGENTS

CROSS-REFERENCES TO RELATED APPLICATIONS

This application is the national stage filing under USC 371 of international application PCT/US2016/063408, filed Nov. 22, 2016, which claims the benefit of U.S. Provisional Application No. 62/259,842, filed Nov. 25, 2015, which are incorporated herein by reference in their entirety and for all purposes.

BACKGROUND

Platinum-containing compounds form a major class of chemotherapeutic agents, which are used to treat a variety of solid tumors alone or in combinations with other drugs. Platinum compounds may bind to DNA and inhibit DNA replication. Though effective in killing cancer cells, these compounds lack specificity and kill normal healthy cells causing profound toxicities to patients, even at therapeutic doses. A major goal in the development of novel platinum compounds is to selectively target the tumor and avoid healthy cells. To this end, facilitating entry of the platinum into tumors while avoiding healthy tissues in which influx transporters are expressed at lower levels relative to cancer cells is highly desired. Further, targeting transporters that bring essential nutrients into tumor cells may also be highly desired. Finally constructing molecules with multiple mechanisms for killing tumors may also be desired. Folic acid is essential in tumor cells and hence transporters that bring folic acid into tumor cells could be important in the cancer cell growth. Designing platinum compounds which interact with one or more of these transporters would allow targeting of tumor cells, which express these transporters for folic acid uptake. These ligands would be highly effective because they contain a platinum, which may complex with DNA to inhibit DNA replication and a folic acid antagonist, which may interact with proteins in the folic acid pathway such as folic acid transporters, which are essential for cell growth. The folic acid antagonist moiety could directly inhibit these proteins or bring the platinum in contact with the proteins to form platinum adducts. Disclosed herein, inter alia, are solutions to these and other problems in the art.

BRIEF SUMMARY OF THE INVENTION

In an aspect is provided a compound, or a pharmaceutically acceptable salt thereof, having the formula:

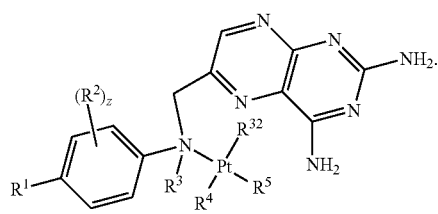

$R^1$ is independently hydrogen, halogen, —$CY^1_3$, —CN, —OH, —$NH_2$, —COOH, —$CONH_2$, —$NO_2$, —SH, —$SO_3H$, —$SO_4H$, —$SO_2NH_2$, —$ONH_2$, —NHC=(O)NHNH$_2$, —NHC=(O)NH$_2$, —NHSO$_2$H, —NHC=(O)H, —NHC(O)—OH, —NHOH, —$OCY^1_3$, —$OCHY^1_2$, —$OCF_3$, —$SR^9$, —$OSO_2R^8$, —$OSO_3H$, —$NH_2NH_2$, —$ONR^6R^7$, —$NH_2C$=(O)$NR^6R^7$, —$NR^6R^7$, —$OC(O)R^8$, —$OC(O)$ $NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCY^2_3$, —$OCHY^2_2$, —$OCF_3$, —$CY^2_3$, —$SO_qR^{10}$, —$SO_uNR^{11}R^{12}$, —$ONR^{11}R^{12}$, —NHC=(O)$NR^{11}R^{12}$, —N(O)$_m$, —$NR^{11}R^{12}$, —$C(O)R^{13}$, —$C(O)$—$OR^{13}$, —$C(O)$ $NR^{11}R^{12}$, —$OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is an unsubstituted $C_1$-$C_4$ alkyl or H. $R^4$, $R^5$ and $R^{32}$ are independently halogen,

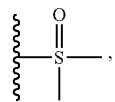

—$OH_2$, —$NH_2$, —$NH_3$, —OH, thiosulfate, unsubstituted alkyl (e.g. $C_1$-$C_4$ alkyl), —$N_3$, —SCN, or —CN. $R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl. $R^4$ and $R^{32}$ may optionally be joined to form a substituted or unsubstituted cycloalkyl, substituted or unsubstituted heterocycloalkyl, substituted or unsubstituted aryl, or substituted or unsubstituted heteroaryl. $R^5$ and $R^{32}$ may optionally be joined to form a substituted or unsubstituted cycloalkyl, substituted or unsubstituted heterocycloalkyl, substituted or unsubstituted aryl, or substituted or unsubstituted heteroaryl. $R^6$, $R^7$, $R^8$, $R^9$, $R^{10}$, $R^{11}$, $R^{12}$, and $R^{13}$ are independently hydrogen, halogen, —$CY^3_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCY^3_3$, —$OCHY^3_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ and $R^7$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. The symbol z is an integer from 0 to 4. The symbol u is independently an integer from 1 to 2. The symbol m is independently an integer from 1 to 2. The symbol q is independently an integer from 0 to 4. The symbols $Y^1$ and $Y^2$ are independently —Cl, —Br, —I, or —F.

In a second aspect is provided, a pharmaceutical composition including a pharmaceutically acceptable excipient and a compound as described herein, or a pharmaceutically acceptable salt of a compound described herein.

In an aspect is provided a method of treating cancer in a patient in need of such treatment, wherein the method includes administering a therapeutically effective amount of a compound as described herein or a pharmaceutically acceptable salt thereof.

In a further aspect is provided, a method of treating cancer in a patient in need of such treatment, wherein the patient has cancer cells expressing a folate transporter protein or mRNA, the method including administering a therapeutically effective amount of a compound as described herein or a pharmaceutically acceptable salt thereof.

In an aspect is provided, a method of treating cancer in a patient in need of such treatment, wherein the patient has cancer cells expressing an organic anion transporter protein or mRNA, the method including administering a therapeutically effective amount of a compound as described herein or a pharmaceutically acceptable salt thereof.

In an aspect is provided, a method of inhibiting replication of DNA (e.g., by causing crosslinking of DNA) in a cell, wherein the cell expresses a folate transporter protein or mRNA, the method including contacting the cell with an effective amount of a compound as described herein or a pharmaceutically acceptable salt thereof.

In an aspect is provided, is a method of inhibiting replication of DNA (e.g., by causing crosslinking of DNA) in a cell, wherein the cell expresses an organic anion transporter protein or mRNA, the method including contacting the cell with an effective amount of a compound as described herein or a pharmaceutically acceptable salt thereof.

In a further aspect is provided a method of inducing cell death in a cell, wherein the cell expresses a folate transporter protein or mRNA, the method including contacting the cell with an effective amount of a compound as described herein or a pharmaceutically acceptable salt thereof.

In a further aspect is provided a method of inducing cell death in a cell, wherein the cell expresses an organic anion transporter protein or mRNA, the method including contacting the cell with an effective amount of a compound as described herein or a pharmaceutically acceptable salt thereof.

In a further aspect is provided a method of inducing cell death in a cell, wherein the cell expresses proteins in the folic acid pathway, the method including contacting the cell with an effective amount of a compound as described herein.

BRIEF DESCRIPTION OF THE DRAWINGS

FIG. 2A shows the effect of folinic acid (1000 μM) on attenuating the cytotoxicity of SM-69 (AT-69). FIG. 2B shows the percent growth of HEK293T after 72 hours of knockdown by siRNAs (negative control, DHFR and SLC19A1). Reducing expression levels of SLC19A1 reduced cytotoxicity of SM-69 (AT-69) (triangle). Reducing expression levels of DHFR (square), a protein in the folic acid pathway, enhanced cytotoxicity of SM-69. This result is similar to methotrexate, although the potency of SM-69 to inhibit DHFR is much weaker compared to methotrexate.

FIG. 3A shows the cisplatin and SM-69 (AT-69) platinum content associated with genomic DNA was measured using ICP mass spectrometer. Methotrexate and saline treated HEK293 cells did not have strong intensity (binding) with the genomic DNA compared with cisplatin and SM-69 (AT-69). FIG. 3B displays the platinum content of SM-69 associated with genomic DNA. The content of SM-69 binding to DNA is higher with higher doses.

FIG. 5A: Pt levels (nmol/mg tissue). For each histogram group, test concentrations were AT-69 at 2.5 mpk (fine checks), AT-69 at 5 mpk (coarse checks), and cisplatin at 2 mpk (horizontal stripes). Bins in order (left to right): liver, kidney, bone marrow, and brain. FIG. 5B: Pt distribution (tissue/plasma). For each histogram group, test concentrations were AT-69 at 2.5 mpk (fine checks), AT-69 at 5 mpk (coarse checks), and cisplatin at 2 mpk (horizontal stripes). Bins in order (left to right): liver, kidney, bone marrow, and brain. FIG. 5C: Pt levels (nmol/mg tissue). For each histogram group, test concentrations were AT-70 at 2.5 mpk (fine checks), AT-70 at 5 mpk (coarse checks), and cisplatin at 2 mpk (horizontal stripes). Bins in order (left to right): liver, kidney and bone marrow. FIG. 5D: Pt distribution (tissue/plasma). For each histogram group, test concentrations were AT-70 at 2.5 mpk (fine checks), AT-70 at 5 mpk (coarse checks), and cisplatin at 2 mpk (horizontal stripes). Bins in order (left to right): liver, kidney, and bone marrow.

FIG. 7A shows the Blood urea nitrogen (BUN) levels in mice 4 weeks after treatment with the different dose of the platinum agents. Mice treated with cisplatin at 5 mg/kg showed significantly higher BUN compared with other groups. FIG. 7B shows Serum creatinine levels in mice 4 weeks after treatment with the different dose of the platinum agents. Mice treated with cisplatin at 5 mg/kg showed significantly higher creatinine levels compared with other groups.

FIG. 9 depicts that greater SLC19A1 (RFC) mRNA expression levels are correlated with increased sensitivity of SM-69 in 53 cancer cell lines. The mRNA expression levels of SLC19A1 were obtained from CellMiner™ Build 1.0 and the $GI_{50}$ (concentrations required to inhibit growth by 50%) were determined by the NCI Drug Therapeutic Program. There is a significant correlation between the expression levels and $GI_{50}$, where the greater expression levels of SLC19A1 (y-axis) correlate with lower $GI_{50}$ (x-axis) (Pearson coefficient, r=0.399, P-value=0.0031).

FIG. 10 depicts the inhibition of SLC19A1-mediated uptake of 3H-methotrexate by SM69. The $IC_{50}$ of SM69 was 6.5 μM, indicating the compound is a potent inhibitor of the transporter. SM69 inhibits DHFR to a lesser degree (at SM69 concentrations of only 10% to 20% of the enzyme activity was inhibited). The Log $IC_{50}$ of SM69 is 0.8121.

FIG. 11A: Body weight (% of vehicle) over 30-days for AT-69 at 2.5 mpk (circle), 5 mpk (square), 7.5 mpk (triangle tip up), and cisplatin at 5 mpk (triangle tip down). FIG. 11B: Body weight (% of vehicle) over 30-days for AT-70 at 2.5 mpk (circle), 5 mpk (square), 7.5 mpk (triangle tip up), and cisplatin at 5 mpk (triangle tip down).

FIG. 12A: cumulative food consumption (gm/mouse) over time for vehicle (circle), AT-69 at 2.5 mpk (square), AT-69 at 5 mpk (triangle tip up), AT-69 at 7.5 mpk (triangle tip down), and cisplatin at 5 mpk (diamond). FIG. 12B: cumulative food consumption (gm/mouse) over time for vehicle (circle), AT-70 at 2.5 mpk (square), AT-70 at 5 mpk (triangle tip up), AT-70 at 7.5 mpk (triangle tip down), and cisplatin at 5 mpk (diamond).

FIG. 13 depicts that significant increase with AT-69 and AT-70 of survival in SKNDZ xenograft model. Legend: vehicle (solid line); cisplatin at 5 mpk (dotted line), AT-69 at 5 mpk (equal spaced dashed line), AT-70 (alternating long and short dashed line).

FIG. 14 depicts that AT-69 and AT-70 significantly increase survival in RMS13 xenograft model. Legend: vehicle (solid line); cisplatin at 5 mpk (dotted line); AT-69 at 5 mpk (evenly spaced dashed line); AT-70 at 5 mpk (alternating long and short dashed line).

FIG. 15A depicts the cytotoxicity of SM-69 in HeLa R1-11 cells transiently transfected with EV and SLC19A1; with the IC50 reported as 0.9695 in HeLa R1-11 (EV) and 0.0284 in HeLa R1-11 (SLC19A1). FIG. 15B depicts the cytotoxicity of SM-69 in HeLa R1-11 cells transiently transfected with EV and SLC46A1; with the IC50 reported as 1.095 in HeLa R1-11 (EV) and 0.1594 in HeLa R1-11 (SLC46A1). FIG. 15C depicts the cytotoxicity of SM-69B in HeLa R1-11 cells transiently transfected with EV and SLC19A1; with the IC50 reported as 2.989 in HeLa R1-11 (EV) and 0.1094 in HeLa R1-11 (SLC19A1). FIG. 15D depicts the cytotoxicity of SM-69B in HeLa R1-11 cells transiently transfected with EV and SLC46A1; with the IC50 reported as 3.373 in HeLa R1-11 (EV) and 0.7024 in HeLa R1-11 (SLC46A1).

DETAILED DESCRIPTION

Figure 1A:
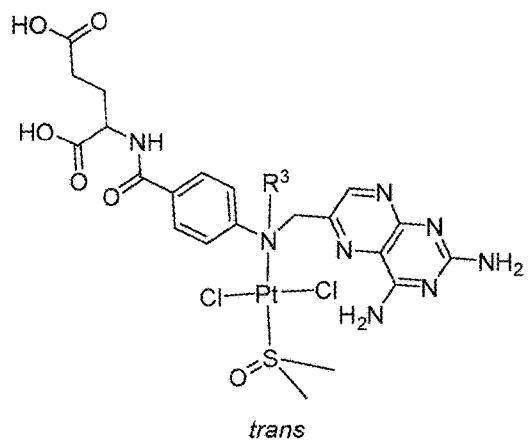
FIGS. 1A-1B. The proposed chemical structure of SM-69 ($R^3$=$CH_3$), a platinum-methotrexate complex, [Pt(DMSO)methotrexate(Cl)] and is assumed to encompass all stereoisomers. This structure includes one dimethyl sulfoxide (DMSO) ligand and one chloride ligand on the leaving group of the platinum complex. The methotrexate is the ligand of the non-leaving group. The synthesis of SM-70 (AT-70) is identical, however aminopterin was used instead of methotrexate thus, $R^3$=H. The synthesis without including DMSO to the solutions of methotrexate was also performed. As a result of this synthesis, the structure of the product does not have DMSO as ligand and instead will have two chloride ligands on the leaving group of the platinum complex. This product is called SM-69B (wherein $R^3$ of FIG. 1B is $CH_3$) or SM-70B (wherein $R^3$ of FIG. 1B is H).

Described herein are platinum analogs complexed to ligands that interact with transporters in cancer cells. The analogs contain a ligand that interacts with proteins in folic acid pathways including transporters for folic acid such as folate and various organic anion transporters. In embodiments, the transporter is a folate transporter. In embodiments, the transporter is an organic anion transporter. The potency of the platinum analogs is correlated with the expression levels of a folic acid transporter (e.g. SLC19A1) and are more potent than cisplatin in various cancer cell lines (e.g. neuroblastoma, osteosarcoma, rhabdomyosarcoma, ovarian cancer, prostate cancer and pancreatic cancer). Without being bound by theory or mechanism (e.g., mechanism of action of a compound in a method or use), described herein, inter alia, are compounds and methods of using the same for treating diseases.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R''—SR', -halogen, —SiR'R''R''', —OC(O)R', —C(O)R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R')=NR''', —S(O)R', —S(O)$_2$R', —S(O)$_2$NR'R'', —NRSO$_2$R', —NR'NR''R''', —ONR'R'', —NR'C=(O)NR''NR'''R'''', —CN, —NO$_2$, in a number ranging from zero to (2m'+1), where m' is the total number of carbon atoms in such radical. R, R', R'', R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR' R')=NR''', —S(O)R', —S(O)$_2$R', —S(O)$_2$NR'R'', —NRSO$_2$R', —NR'NR''R''', —ONR'R'', —NR'C=(O)NR''NR'''R'''', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, independently substituted with at least one or more substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, independently substituted with at least one or more substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer). For example certain methods herein treat cancer by decreasing or reducing or preventing the occurrence, growth, metastasis, or progression of cancer or by decreasing or reducing or preventing a symptom of cancer. Symptoms of cancer (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer) would be known or may be determined by a person of ordinary skill in the art. The term "treating" and conjugations thereof, include prevention of an injury, pathology, condition, or disease (e.g. preventing the development of one or more symptoms of cancer (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer).

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example cancer may be treated with an agent (e.g. compound as described herein) effective for inhibiting DNA replication.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In embodiments, inhibition refers to a decrease in DNA replication or transcription. In some embodiments inhibition refers to reduction of a disease or symptoms of disease (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer). Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments "cancer" refers to a cancer resistant to an anti-cancer therapy (e.g. treatment with an anti-cancer agent (e.g. hormonal therapy, hormonal therapeutic agent, tamoxifen, trastuzumab, or an aromatase inhibitor)).

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In embodiments, the disease is cancer. In embodiments, the disease is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents (e.g. anti-cancer agents) known to be useful in treating a disease described herein (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent (e.g. anti-cancer agent). Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In embodiments, the second active agent is folinic acid.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin—N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$ and/or $R^{2.4}$ respectively, wherein the definition of $R^2$ is assumed by $R^{2.1}$, $R^{2.2}$, $R^{2.3}$ and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

The term "organic anion transporter" refers to a protein that mediates the transport of organic anions (e.g., folic acid) across the cell membrane. In embodiments, an "organic anion transporter" is a reduced folate carrier (e.g. RFC, SLC19A1), a proton-coupled folate transporter (PCFT), an organic anion transporter 1 (e.g. OAT1 (SLC22A6)), an organic anion transporter 3 (e.g. OAT3 (SLC22A8)), or an organic anion-transporting polypeptide 1A2 (e.g. OATP1A2 (SLCO1A2)) or an organic anion-transporting polypeptide 2B1 (e.g. OATP2B1 (SLCO2B1)).

The term "folate transporter" or "Solute carrier family 19 (folate transporter), member 1" or "SLC19A1" or "RFC1" or "RFC" refers to an organic anion transporter protein that transports folate compounds. The term "folate transporter" may refer to the nucleotide sequence or protein sequence of human folate transporter encoded by the SLC19A1 gene (with three different isoforms: RefSeq NM_001205206, GI: 327199313, NP_001192135, and/or RefSeq NM_001205207, GI: 327199316, NP_001192136, and/or RefSeq NM_194255, GI: 34808710, NP_919231). The term "folate transporter" includes both the wild-type form of the nucleotide sequences or proteins as well as any mutants thereof. In some embodiments, "folate transporter" is wild-type folate transporter. In embodiments, "folate transporter" is one or more mutant forms. In embodiments, folate transporter is the human folate transporter. In embodiments, the folate transporter has the nucleotide sequence corresponding to reference number GI: 327199313. In embodiments, the folate transporter has the nucleotide sequence corresponding to RefSeq NM_001205206.1. In embodiments, the folate transporter has the protein sequence corresponding to reference number GI: 327199314. In embodiments, the folate transporter has the protein sequence corresponding to RefSeq NP_001192135.1.

The term "proton-coupled folate transporter" or "Solute carrier family 46 (folate transporter), member 1" or "SLC46A1" or "PCFT" refers to an organic anion transporter protein that transports folate compounds. The term "proton-coupled folate transporter" may refer to the nucleotide sequence or protein sequence of human proton-coupled folate transporter (e.g., Entrez 113235, Uniprot Q96NT5, RefSeq NM_001242366, GI: 530788235, RefSeq NP_001229295, and/or RefSeq NM_080669, GI: 530788234, RefSeq NP_542400). The term "proton-coupled folate transporter" includes both the wild-type form of the nucleotide sequences or proteins as well as any mutants thereof. In some embodiments, "proton-coupled folate transporter" is wild-type proton-coupled folate transporter. In embodiments, "proton-coupled folate transporter" is one or more mutant forms. In embodiments, proton-coupled folate transporter is the human proton-coupled folate transporter. In embodiments, the proton-coupled folate transporter has the nucleotide sequence corresponding to reference number GI: 530788235. In embodiments, the proton-coupled folate transporter has the nucleotide sequence corresponding to RefSeq NM_001242366.2. In embodiments, the proton-coupled folate transporter has the protein sequence corresponding to reference number GI: 334688816. In embodiments, the proton-coupled folate transporter has the protein sequence corresponding to RefSeq NP_001229295.1.

The term "organic anion transporter 1" or "OAT1" refers to an organic anion transporter protein that transports folate compounds. The term "organic anion transporter 1" may refer to the nucleotide sequence or protein sequence of human organic anion transporter 1 encoded by the SLC22A6 gene (e.g., Entrez 9356, Uniprot Q4U2R8, RefSeq NM_004790, GI: 332164709, RefSeq NP_004781, and/or RefSeq NM_153276, GI: 332164711, RefSeq NP_695008 and/or RefSeq NM_153277, GI: 24497478, RefSeq NP_695009 and/or RefSeq NM_153278, GI: 24497480, RefSeq NP_695010 GI: 20070188). The term "organic anion transporter 1" includes both the wild-type form of the nucleotide sequences or proteins as well as any mutants thereof. In some embodiments, "organic anion transporter 1" is wild-type organic anion transporter 1. In embodiments, "organic anion transporter 1" is one or more mutant forms. In embodiments, organic anion transporter 1 is the human organic anion transporter 1. In embodiments, the organic anion transporter 1 has the nucleotide sequence corresponding to reference number GI: 332164709. In embodiments, the organic anion transporter 1 has the nucleotide sequence corresponding to RefSeq NM_004790.4. In embodiments, the organic anion transporter 1 has the protein sequence corresponding to reference number GI: 20070188. In embodiments, the organic anion transporter 1 has the protein sequence corresponding to RefSeq NP_004781.2.

The term "organic anion transporter 3" or "OAT3" refers to an organic anion transporter protein that transports folate compounds. The term "organic anion transporter 3" may refer to the nucleotide sequence or protein sequence of human organic anion transporter 3 encoded by the SLC22A8 gene (e.g., Entrez 9376, Uniprot Q8TCC7, RefSeq NM_001184732, GI: 296080718, RefSeq NP_001171661, and/or RefSeq NM_001184733, RefSeq NP_001171662, GI: 296080721, and/or RefSeq NM_001184736, RefSeq NP_001171665, GI: 296080734, and/or RefSeq NM_004254, RefSeq NP_004245, GI: 24497499). The term "organic anion transporter 3" includes both the wild-type form of the nucleotide sequences or proteins as well as any mutants thereof. In some embodiments, "organic anion transporter 3" is wild-type organic anion transporter 3. In embodiments, "organic anion transporter 3" is one or more mutant forms. In embodiments, organic anion transporter 3 is the human organic anion transporter 3. In embodiments, the organic anion transporter 3 has the nucleotide sequence corresponding to reference number GI: 296080718. In embodiments, the organic anion transporter 3 has the nucleotide sequence corresponding to RefSeq NM_001184732.1. In embodiments, the organic anion transporter 3 has the protein sequence corresponding to reference number GI: 296080719. In embodiments, the organic anion transporter 3 has the protein sequence corresponding to RefSeq NP_001171661.1.

The term "organic anion-transporting polypeptide 1A2" or "OATP1A2" or "SLCO1A2" refers to an organic anion transporter protein that transports folate compounds. The term "organic anion-transporting polypeptide 1A2" may refer to the nucleotide sequence or protein sequence of human organic anion-transporting polypeptide 1A2 encoded by the SLCO1A2 gene (e.g., Entrez 6579, Uniprot P46721, RefSeq NM_005075, GI: 19913400, RefSeq NP_066580, and/or RefSeq NM_021094, NP_066580, GI: 10835099, and/or RefSeq NM_134431, NP_602307, GI:19913403). The term "organic anion-transporting polypeptide 1A2" includes both the wild-type form of the nucleotide sequences or proteins as well as any mutants thereof. In some embodiments, "organic anion-transporting polypeptide 1A2" is wild-type organic anion-transporting polypeptide 1A2. In embodiments, "organic anion-transporting polypeptide 1A2" is one or more mutant forms. In embodiments, organic anion-transporting polypeptide 1A2 is the human organic anion-transporting polypeptide 1A2. In embodiments, the organic anion-transporting polypeptide 1A2 has the nucleotide sequence corresponding to reference number GI: 19913400. In embodiments, the organic anion-transporting polypeptide 1A2 has the nucleotide sequence corresponding to RefSeq NM_005075.1. In embodiments, the organic anion-transporting polypeptide 1A2 has the protein sequence corresponding to reference number GI: 10835099. In embodiments, the organic anion-transporting polypeptide 1A2 has the protein sequence corresponding to RefSeq NP_066580.1.

The term "organic anion-transporting polypeptide 2B1" or "OATP2B1" or "SLCO2B1" refers to an organic anion transporter protein that transports folate compounds. The term "organic anion-transporting polypeptide 2B1" may refer to the nucleotide sequence or protein sequence of human organic anion-transporting polypeptide 2B1 encoded by the SLCO2B1 gene (e.g., Entrez 11309, Uniprot O94956, RefSeq NM_001145211, GI: 312176373, RefSeq NP_001138683, and/or GI: 223634012). The term "organic anion-transporting polypeptide 2B1" includes both the wild-type form of the nucleotide sequences or proteins as well as any mutants thereof. In some embodiments, "organic anion-transporting polypeptide 2B1" is wild-type organic anion-transporting polypeptide 2B1. In embodiments, "organic anion-transporting polypeptide 2B1" is one or more mutant forms. In embodiments, organic anion-transporting polypeptide 2B1 is the human organic anion-transporting polypeptide 2B1. In embodiments, the organic anion-transporting polypeptide 2B1 has the nucleotide sequence corresponding to reference number GI: 312176373. In embodiments, the organic anion-transporting polypeptide 2B1 has the nucleotide sequence corresponding to RefSeq NM_001145211.2. In embodiments, the organic anion-transporting polypeptide 2B1 has the protein sequence corresponding to reference number GI: 223634012. In embodiments, the organic anion-transporting polypeptide 2B1 has the protein sequence corresponding to RefSeq NP_001138683.1.

The term "platinum-based compound" is used in accordance with its normal meaning and refers to a coordinated platinum agent. For example, a platinum-based compound may be cisplatin, carboplatin, oxaliplatin, satraplatin, picoplatin, nedaplatin, triplatin, or a compound described herein.

II. Compounds

In an aspect is provided a compound, or a pharmaceutically acceptable salt thereof, having the formula:

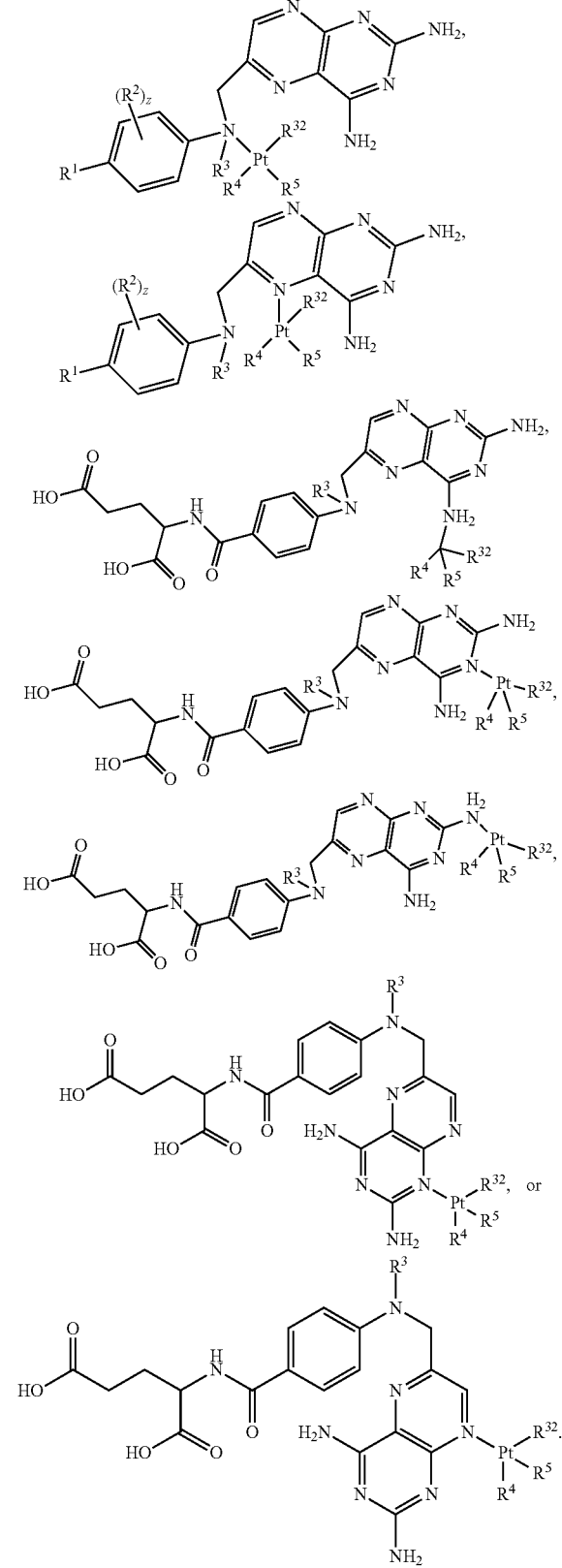

$R^1$ is independently hydrogen, halogen, —$CY^1_3$, —CN, —OH, —$NH_2$, —COOH, —$CONH_2$, —$NO_2$, —SH, —$SO_3H$, —$SO_4H$, —$SO_2NH_2$, —$ONH_2$, —NHC=(O)

$NHNH_2$, $-NHC=(O)NH_2$, $-NHSO_2H$, $-NHC=(O)H$, $-NHC(O)-OH$, $-NHOH$, $-OCY^1_3$, $-OCHY^1_2$, $-OCF_3$, $-SR^9$, $-OSO_2R^8$, $-OSO_3H$, $-NH_2NH_2$, $-ONR^6R^7$, $-NH_2C=(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently halogen, $-CY^1_3$, $-CN$, $-SR^9$, $-OSO_2R^8$, $-OSO_3H$, $-NH_2NH_2$, $-ONR^6R^7$, $-NH_2C(O)NHNH_2$, $-C(O)R^8$, $-C(O)NR^6R^7$, $-NH_2C(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCY^2_3$, $-OCHY^2_2$, $-OCF_3$, $-CY^2_3$, $-SO_qR^{10}$, $-SO_nNR^{11}R^{12}$, $-ONR^{11}R^{12}$, $-NHC=(O)NR^{11}R^{12}$, $-N(O)_m$, $-NR^{11}R^{12}$, $-C(O)R^{13}$, $-C(O)-OR^{13}$, $-C(O)NR^{11}R^{12}$, $-OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently halogen, $-CY^2_3$, $-CN$, $-SO_qR^{10}$, $-SO_nNR^{11}R^{12}$, $-NHNH_2$, $-ONR^{11}R^{12}$, $-NHC=(O)NHNH_2$, $-NHC=(O)NR^{11}R^{12}$, $-N(O)_m$, $-NR^{11}R^{12}$, $-C(O)R^{13}$, $-C(O)-OR^{13}$, $-C(O)NR^{11}R^{12}$, $-OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is an unsubstituted $C_1$-$C_4$ alkyl or H. $R^4$, $R^5$ and $R^{32}$ are independently halogen,

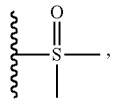

$-OH_2$, $-NH_3$, $-NH_2$, $-OH$, thiosulfate, unsubstituted alkyl (e.g. $C_1$-$C_4$ alkyl), $-N_3$, $-SCN$, or $-CN$. $R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl. $R^4$ and $R^{32}$ may optionally be joined to form a substituted or unsubstituted cycloalkyl, substituted or unsubstituted heterocycloalkyl, substituted or unsubstituted aryl, or substituted or unsubstituted heteroaryl. $R^5$ and $R^{32}$ may optionally be joined to form a substituted or unsubstituted cycloalkyl, substituted or unsubstituted heterocycloalkyl, substituted or unsubstituted aryl, or substituted or unsubstituted heteroaryl. $R^6$, $R^7$, $R^8$, $R^9$, $R^{10}$, $R^{11}$, $R^{12}$, and $R^{13}$ are independently hydrogen, halogen, $-CY^3_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCY^3_3$, $-OCHY^3_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ and $R^7$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. The symbol z is an integer from 0 to 4. The symbol u is independently an integer from 1 to 2. The symbol m is independently an integer from 1 to 2. The symbol q is independently an integer from 0 to 4. The symbols $Y^1$ and $Y^2$ are independently $-Cl$, $-Br$, $-I$, or $-F$.

In embodiments, the compound has the formula:

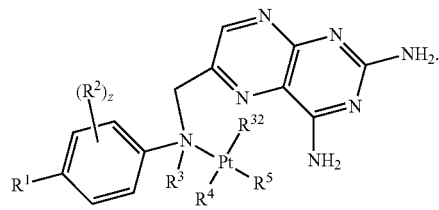

In embodiments $R^1$ is independently halogen, $-SR^9$, $-OSO_2R^8$, $-OSO_3H$, $-NH_2NH_2$, $-ONR^6R^7$, $-NH_2C=(O)NHNH_2$, $-NH_2C=(O)NR^6R^7$, $-NR^6R^7$, $-OC(O)R^8$, $-OC(O)NR^6R^7$, $-OR^9$, $-CH_2C=(O)NR^6R^7$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^1$ is hydrogen.

In embodiments, $R^1$ is independently halogen, $-CY^1_3$, $-CN$, $-OH$, $-NH_2$, $-COOH$, $-CONH_2$, $-NO_2$, $-SH$, $-SO_3H$, $-SO_4H$, $-SO_2NH_2$, $-ONH_2$, $-NHC=(O)$ $NHNH_2$, $-NHC=(O)NH_2$, $-NHSO_2H$, $-NHC=(O)H$, $-NHC(O)-OH$, $-NHOH$, $-OCY^1_3$, $-OCHY^1_2$, $-OCF_3$, $-SR^9$, $-OSO_2R^8$, $-OSO_3H$, $-NH_2NH_2$, $-ONR^6R^7$, $-NH_2C=(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently halogen, $-CY^1_3$, $-CN$, $-SR^9$, $-OSO_2R^8$, $-OSO_3H$, $-NH_2NH_2$, $-ONR^6R^7$, $-NH_2C(O)NHNH_2$, $-C(O)R^8$, $-C(O)NR^6R^7$, $-NH_2C(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is substituted or unsubstituted heteroalkyl. In embodiments, $R^1$ is substituted or unsubstituted 2 to 10 membered heteroalkyl. In embodiments, $R^1$ is substituted or unsubstituted 4 to 8 membered heteroalkyl. In embodiments, $R^1$ is substituted with oxo, —OH, —NH$_2$, —SH, —COOH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^1$ is substituted or unsubstituted $C_1$-$C_8$ alkyl. In embodiments, $R^1$ is substituted or unsubstituted $C_1$-$C_6$ alkyl. In embodiments, $R^1$ is substituted or unsubstituted $C_1$-$C_4$ alkyl. In embodiments, $R^1$ is substituted or unsubstituted 2 to 10 membered heteroalkyl. In embodiments, $R^1$ is substituted or unsubstituted 2 to 8 membered heteroalkyl. In embodiments, $R^1$ is substituted or unsubstituted 4 to 8 membered heteroalkyl. In embodiments, $R^1$ is substituted or unsubstituted 2 to 6 membered heteroalkyl. In embodiments, $R^1$ is substituted or unsubstituted 2 to 4 membered heteroalkyl. In embodiments, $R^1$ is substituted or unsubstituted 5 membered heteroalkyl.

In embodiments, $R^1$ is substituted alkyl (e.g. $C_1$-$C_8$ alkyl, $C_1$-$C_6$ alkyl, or $C_1$-$C_4$ alkyl), substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^1$ is substituted $C_1$-$C_8$ alkyl. In embodiments, $R^1$ is substituted $C_1$-$C_6$ alkyl. In embodiments, $R^1$ is substituted $C_1$-$C_4$ alkyl. In embodiments, $R^1$ is substituted 2 to 10 membered heteroalkyl. In embodiments, $R^1$ is substituted 2 to 8 membered heteroalkyl. In embodiments, $R^1$ is substituted 4 to 8 membered heteroalkyl. In embodiments, $R^1$ is substituted 2 to 6 membered heteroalkyl. In embodiments, $R^1$ is substituted 2 to 4 membered heteroalkyl. In embodiments, $R^1$ is substituted 5 membered heteroalkyl. In embodiments, $R^1$ is substituted with oxo, —OH, or —COOH. In embodiments, $R^1$ is substituted with oxo. In embodiments, $R^1$ is substituted with —OH. In embodiments, $R^1$ is substituted with —COOH.

In embodiments, $R^1$ is —C(O)NR$^6$R$^7$. In embodiments, $R^1$ is —C(O)NHR$^7$. In embodiments, $R^7$ is a substituted $C_1$-$C_8$ alkyl. In embodiments, $R^7$ is a substituted $C_1$-$C_4$ alkyl. In embodiments, $R^7$ is a substituted $C_1$-$C_3$ alkyl. In embodiments, $R^7$ is a substituted $C_2$-$C_4$ alkyl. In embodiments, $R^7$ is substituted with oxo, —OH, or —COOH. In embodiments, $R^7$ is substituted with oxo. In embodiments, $R^7$ is substituted with —OH. In embodiments, $R^7$ is substituted with —COOH.

In embodiments, $R^1$ is selected from the following group:

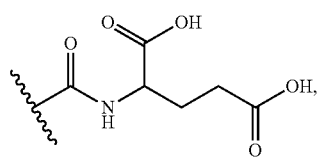

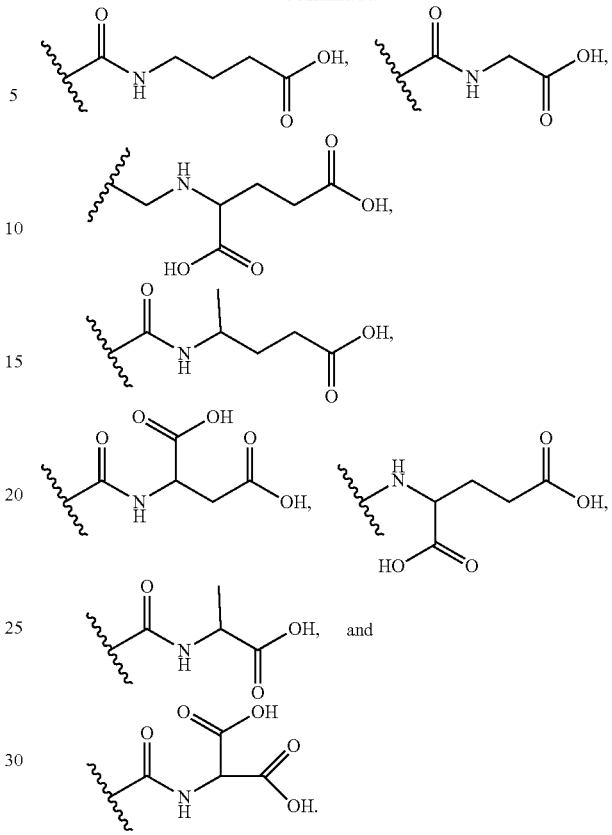

In embodiments, $R^1$ is substituted with oxo, —OH, —NH$_2$, —SH, —COOH, —CN, —CF$_3$, —NO$_2$, halogen, unsubstituted alkyl (e.g., $C_1$-$C_4$ alkyl), unsubstituted heteroalkyl, unsubstituted cycloalkyl, unsubstituted heterocycloalkyl, unsubstituted aryl, or unsubstituted heteroaryl. In embodiments, $R^1$ is substituted with oxo, —OH, or —COOH.

In embodiments, $R^1$ is independently halogen, —CY$^1$$_3$, —SR$^9$, —OSO$_2$R$^8$, —OSO$_3$H, —NH$_2$NH$_2$, —ONR$^6$R$^7$, —NH$_2$C(O)NHNH$_2$, —C(O)R$^8$, —C(O)NR$^6$R$^7$, —NH$_2$C(O)NR$^6$R$^7$, —NR$^6$R$^7$, —OC(O)R$^8$, —OC(O)NR$^6$R$^7$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^6$R$^7$, —OC(O)R$^8$, —OC(O)NR$^6$R$^7$, —OR$^9$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

In embodiments $R^1$ is independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O) OC(O)R$^8$, —OC(O)NR$^6$R$^7$, —OR$^9$, $R^{14}$-substituted or unsubstituted alkyl (e.g. $C_1$-$C_8$ alkyl, $C_1$-$C_6$ alkyl, or $C_1$-$C_4$ alkyl), $R^{14}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14}$-substituted or unsubstituted aryl (e.g. $C_6$-$C_{10}$ aryl or $C_6$ aryl), or $R^{14}$-substituted or unsubstituted heteroaryl (e.g. 5 to 10 membered heteroaryl, 5 to 9 membered heteroaryl, or 5 to 6 membered heteroaryl).

$R^{14}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{15}$-substituted or unsubstituted alkyl (e.g. $C_1$-$C_8$ alkyl, $C_1$-$C_6$ alkyl, or $C_1$-$C_4$ alkyl), $R^{15}$-substituted or unsubstituted heteroalkyl (e.g. 2 to 8 membered heteroalkyl, 2 to 6 membered heteroalkyl, or 2 to 4 membered heteroalkyl), $R^{15}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15}$-substituted or unsubstituted aryl (e.g. $C_6$-$C_{10}$ aryl or $C_6$ aryl), or $R^{15}$-substituted or unsubstituted heteroaryl (e.g. 5 to 10 membered heteroaryl, 5 to 9 membered heteroaryl, or 5 to 6 membered heteroaryl). In embodiments, $R^{14}$ is glutamic acid. In embodiments, $R^{14}$ is oxo. In embodiments, $R^{14}$ is —COOH. In embodiments, $R^{14}$ is —OH. In embodiments, $R^{14}$ is —$CH_3$.

In embodiments, $R^{14}$ is oxo, —OH, —$NH_2$, —SH, —COOH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound has the formula:

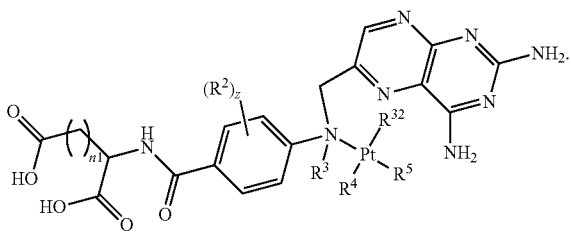

wherein $R^2$, z, $R^3$, $R^4$, $R^5$, and $R^{32}$ are as described herein. The symbol n1 is an integer from 0 to 8. The symbol n1 is an integer from 1 to 8. The symbol n1 is an integer from 2 to 8. In embodiments, n1 is an integer from 2 to 6. In embodiments, n1 is an integer from 2 to 4. In embodiments, n1 is 2.

In embodiments, the compound has the formula

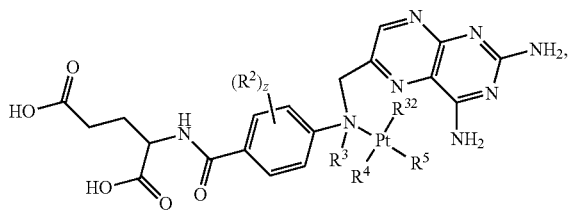

wherein $R^2$, z, $R^3$, $R^4$, $R^5$, and $R^{32}$ are as described herein.

In embodiments, $R^2$ is independently halogen, —$CY^2_3$, —CN, —$SO_qR^{10}$, —$SO_nNR^{11}R^{12}$, —$NHNH_2$, —$ONR^{11}R^{12}$, —NHC=(O)$NHNH_2$, —NHC=(O)$NR^{11}R^{12}$, $N(O)_m$, —$NR^{11}R^{12}$, —$C(O)R^{13}$, —C(O)—$OR^{13}$, —$C(O)NR^{11}R^{12}$, —$OR^{10}$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). Two adjacent $R^2$ substituents may optionally be joined to form a substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl).

In embodiments, $R^2$ is unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). Two adjacent $R^2$ substituents may optionally be joined to form a unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). In embodiments, $R^2$ is unsubstituted alkyl (e.g. $C_1$-$C_8$ alkyl, $C_1$-$C_6$ alkyl, or $C_1$-$C_4$ alkyl), or unsubstituted heteroalkyl (e.g. 2 to 8 membered heteroalkyl, 2 to 6 membered heteroalkyl, or 2 to 4 membered heteroalkyl).

In embodiments, $R^3$ is unsubstituted butyl. In embodiments, $R^3$ is unsubstituted propyl. In embodiments, $R^3$ is unsubstituted ethyl. In embodiments, $R^3$ is unsubstituted methyl. In embodiments, $R^3$ is hydrogen.

In embodiments, $R^4$, $R^5$ and $R^{32}$ are independently halogen

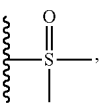

—$OH_2$, —$NH_3$, —$NH_2$, —OH, thiosulfate, —$N_3$, —SCN, or —CN. In embodiments, $R^4$ and $R^5$ may optionally be joined to form a substituted (e.g., independently substituted with one or more substituent groups, size-limited substituents, or lower substituents) or unsubstituted cycloalkyl, substituted (e.g., independently substituted with one or more substituent groups, size-limited substituents, or lower substituents) or unsubstituted heterocycloalkyl, substituted (e.g., independently substituted with one or more substituent groups, size-limited substituents, or lower substituents) or unsubstituted aryl, or substituted or unsubstituted heteroaryl. In embodiments, $R^4$ and $R^{32}$ may optionally be joined to form a substituted (e.g., independently substituted with one or more substituent groups, size-limited substituents, or lower substituents) or unsubstituted cycloalkyl, substituted (e.g., independently substituted with one or more substituent groups, size-limited substituents, or lower substituents) or unsubstituted heterocycloalkyl, substituted (e.g., independently substituted with one or more substituent groups, size-limited substituents, or lower substituents) or unsubstituted aryl, or substituted (e.g., independently substituted with one or more substituent groups, size-limited substituents, or lower substituents) or unsubstituted heteroaryl. In embodiments, $R^5$ and $R^{32}$ may optionally be joined to form substituted (e.g., independently substituted with one or more substituent groups, size-limited substituents, or lower substituents) or unsubstituted cycloalkyl, substituted (e.g., independently substituted with one or more substituent groups, size-limited substituents, or lower substituents) or unsubstituted heterocycloalkyl, substituted (e.g., independently substituted with one or more substituent groups, size-limited substituents, or lower substituents) or unsubstituted aryl, or substituted (e.g., independently substituted with one or more substituent groups, size-limited substituents, or lower substituents) or unsubstituted heteroaryl. In embodiments, $R^4$ and $R^5$ may optionally be joined to form a unsubstituted cycloalkyl, unsubstituted heterocycloalkyl, unsubstituted aryl, or substituted or unsubstituted heteroaryl. In embodiments, $R^4$ and $R^{32}$ may optionally be joined to form a unsubstituted cycloalkyl, unsubstituted heterocycloalkyl, unsubstituted aryl, or unsubstituted heteroaryl. In embodiments, $R^5$ and $R^{32}$ may optionally be joined to form unsubstituted cycloalkyl, unsubstituted heterocycloalkyl, unsubstituted aryl, or unsubstituted heteroaryl.

In embodiments, $R^4$ is halogen or

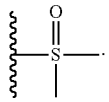

In embodiments, $R^4$ is halogen. In embodiments, $R^4$ is Cl. In embodiments, $R^4$ is

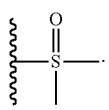

In embodiments, $R^5$ is halogen or

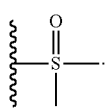

In embodiments, $R^5$ is halogen. In embodiments, $R^5$ is Cl. In embodiments, $R^5$ is

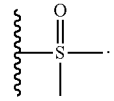

In embodiments, $R^{32}$ is halogen or

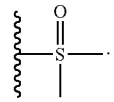

In embodiments, $R^{32}$ is halogen. In embodiments, $R^{32}$ is Cl. In embodiments, $R^{32}$ is

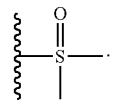

In embodiments, $R^4$ and $R^5$ are halogen and $R^{32}$ is

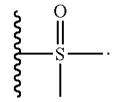

In embodiments, $R^4$ and $R^5$ are Cl and $R^{32}$ is

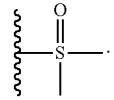

In embodiments, $R^4$ is halogen, dimethyl sulfoxide, $-H_2O$, $-N_3$, $-NH_2$, $-NH_3$, $-SCN$, $-CN$, $-OH$, thiosulfate, or unsubstituted alkyl (e.g. $C_1$-$C_4$ alkyl). In embodiments, $R^4$ is halogen or dimethyl sulfoxide. In embodiments, $R^4$ is halogen. In embodiments, $R^4$ is $-H_2O$. In embodiments, $R^4$ is dimethyl sulfoxide. In embodiments, $R^4$ is $-Cl$. In embodiments, $R^4$ is $-NH_2$. In embodiments, $R^4$ is $-NH_3$.

In embodiments, $R^5$ is halogen, dimethyl sulfoxide, $-H_2O$, $-N_3$, $-NH_2$, $-NH_3$, $-SCN$, $-CN$, $-OH$, thiosulfate, or unsubstituted alkyl (e.g. $C_1$-$C_4$ alkyl). In embodiments, $R^5$ is halogen or dimethyl sulfoxide. In embodiments, $R^5$ is halogen. In embodiments, $R^5$ is $-H_2O$ In embodiments, $R^5$ is dimethyl sulfoxide. In embodiments, $R^5$ is $-Cl$. In embodiments, $R^5$ is $-NH_2$. In embodiments, $R^5$ is $-NH_3$.

In embodiments, $R^{32}$ is halogen, dimethyl sulfoxide, $-H_2O$, $-N_3$, $-NH_2$, $-NH_3$, $-SCN$, $-CN$, $-OH$, thiosulfate, or unsubstituted alkyl (e.g. $C_1$-$C_4$ alkyl). In embodiments, $R^{32}$ is halogen or dimethyl sulfoxide. In embodiments, $R^{32}$ is halogen. In embodiments, $R^{32}$ is $-H_2O$ In embodiments, $R^{32}$ is dimethyl sulfoxide. In embodiments, $R^{32}$ is $-Cl$. In embodiments, $R^{32}$ is $-NH_2$. In embodiments, $R^{32}$ is $-NH_3$.

In embodiments, $R^4$ and $R^5$ may optionally be joined to form oxalate, cyclobutane dicarboxylic acid, or cis-1,2-diaminocyclohexane. In embodiments, $R^4$ and $R^{32}$ may optionally be joined to form oxalate, cyclobutane dicarboxylic acid, or cis-1,2-diaminocyclohexane. In embodiments, $R^{32}$ and $R^5$ may optionally be joined to form oxalate, cyclobutane dicarboxylic acid, or cis-1,2-diaminocyclohexane.

In embodiments, $R^4$ is —Cl and $R^5$ is dimethyl sulfoxide. In embodiments, $R^4$ is dimethyl sulfoxide and $R^5$—Cl. In embodiments, $R^4$ and $R^5$ are joined to form a substituted or unsubstituted cycloalkyl, substituted or unsubstituted heterocycloalkyl, substituted or unsubstituted aryl, or substituted or unsubstituted heteroaryl. It will be understood that in embodiments, the moiety formed by the joining of $R^4$ and $R^5$, as described above does not include the Pt atom and the bonds between the Pt atom and $R^4$ and between the Pt atom and $R^5$, which will be understood to exist between the Pt and $R^4$ and $R^5$ regardless of the substituent formed by the joining of $R^4$ and $R^5$. For example, when $R^4$ and $R^5$ are joined to form a substituted cycloalkyl, it will be understood that the substituted cycloalkyl includes substitutions on the cycloalkyl ring in addition to forming bonds to the Pt atom. As another example, when $R^4$ and $R^5$ are joined to form an unsubstituted heterocycloalkyl, the resulting unsubstituted heterocycloalkyl will include bonds from the unsubstituted ring to the Pt atom. In embodiments, $R^4$ and $R^5$ are joined to form a substituted or unsubstituted heterocycloalkyl, wherein the substituted or unsubstituted heterocycloalkyl includes the Pt atom as a ring heteroatom and the bond between the Pt atom and $R^4$ and the bond between the Pt atom and $R^5$ are ring bonds in the substituted or unsubstituted heterocycloalkyl. It will be understood that the substituted or unsubstituted heterocycloalkyl formed by the joining of $R^4$ and $R^5$ and the Pt atom is a heterocycloalkyl ring at least because of the inclusion of the Pt ring atom, although additional ring heteroatoms may also be included.

In embodiments, $R^4$ is —Cl and $R^{32}$ is dimethyl sulfoxide. In embodiments, $R^4$ is dimethyl sulfoxide and $R^{32}$—Cl. In embodiments, $R^4$ and $R^{32}$ are joined to form a substituted or unsubstituted cycloalkyl, substituted or unsubstituted heterocycloalkyl, substituted or unsubstituted aryl, or substituted or unsubstituted heteroaryl. It will be understood that in embodiments, the moiety formed by the joining of $R^4$ and $R^{32}$, as described above does not include the Pt atom and the bonds between the Pt atom and $R^4$ and between the Pt atom and $R^{32}$, which will be understood to exist between the Pt and $R^4$ and $R^{32}$ regardless of the substituent formed by the joining of $R^4$ and $R^{32}$. For example, when $R^4$ and $R^{32}$ are joined to form a substituted cycloalkyl, it will be understood that the substituted cycloalkyl includes substitutions on the cycloalkyl ring in addition to forming bonds to the Pt atom. As another example, when $R^4$ and $R^{32}$ are joined to form an unsubstituted heterocycloalkyl, the resulting unsubstituted heterocycloalkyl will include bonds from the unsubstituted ring to the Pt atom. In embodiments, $R^4$ and $R^{32}$ are joined to form a substituted or unsubstituted heterocycloalkyl, wherein the substituted or unsubstituted heterocycloalkyl includes the Pt atom as a ring heteroatom and the bond between the Pt atom and $R^4$ and the bond between the Pt atom and $R^{32}$ are ring bonds in the substituted or unsubstituted heterocycloalkyl. It will be understood that the substituted or unsubstituted heterocycloalkyl formed by the joining of $R^4$ and $R^{32}$ and the Pt atom is a heterocycloalkyl ring at least because of the inclusion of the Pt ring atom, although additional ring heteroatoms may also be included.

In embodiments, $R^5$ is —Cl and $R^{32}$ is dimethyl sulfoxide. In embodiments, $R^5$ is dimethyl sulfoxide and $R^{32}$—Cl. In embodiments, $R^5$ and $R^{32}$ are joined to form a substituted or unsubstituted cycloalkyl, substituted or unsubstituted heterocycloalkyl, substituted or unsubstituted aryl, or substituted or unsubstituted heteroaryl. It will be understood that in embodiments, the moiety formed by the joining of $R^5$ and $R^{32}$, as described above does not include the Pt atom and the bonds between the Pt atom and $R^5$ and between the Pt atom and $R^{32}$, which will be understood to exist between the Pt and $R^5$ and $R^{32}$ regardless of the substituent formed by the joining of $R^5$ and $R^{32}$. For example, when $R^5$ and $R^{32}$ are joined to form a substituted cycloalkyl, it will be understood that the substituted cycloalkyl includes substitutions on the cycloalkyl ring in addition to forming bonds to the Pt atom. As another example, when $R^5$ and $R^{32}$ are joined to form an unsubstituted heterocycloalkyl, the resulting unsubstituted heterocycloalkyl will include bonds from the unsubstituted ring to the Pt atom. In embodiments, $R^5$ and $R^{32}$ are joined to form a substituted or unsubstituted heterocycloalkyl, wherein the substituted or unsubstituted heterocycloalkyl includes the Pt atom as a ring heteroatom and the bond between the Pt atom and $R^5$ and the bond between the Pt atom and $R^{32}$ are ring bonds in the substituted or unsubstituted heterocycloalkyl. It will be understood that the substituted or unsubstituted heterocycloalkyl formed by the joining of $R^5$ and $R^{32}$ and the Pt atom is a heterocycloalkyl ring at least because of the inclusion of the Pt ring atom, although additional ring heteroatoms may also be included.

In embodiments, the compound has the formula:

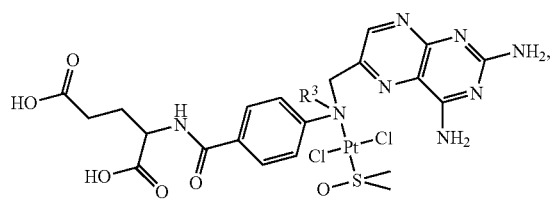

wherein $R^3$ is as described herein. In embodiments, the compound has the formula:

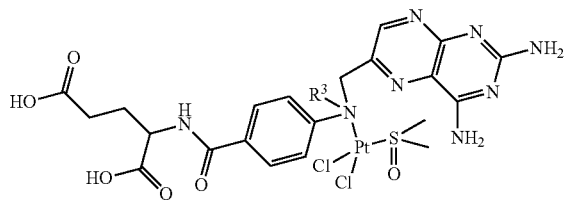

wherein $R^3$ is as described herein.

In embodiments, the compound has the formula:

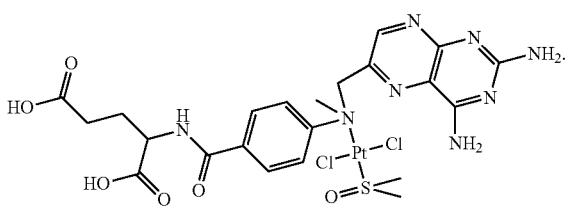

In embodiments, the compound has the formula:

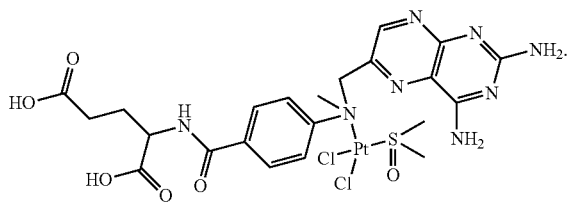

In embodiments, the compound has the formula:

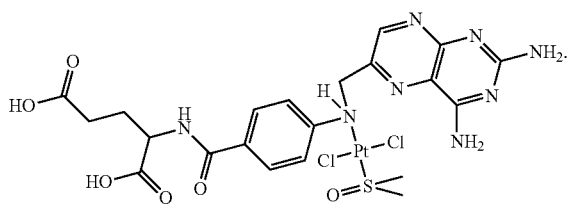

In embodiments, the compound has the formula:

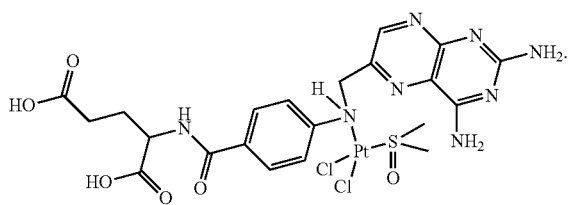

In embodiments, the compound has the formula:

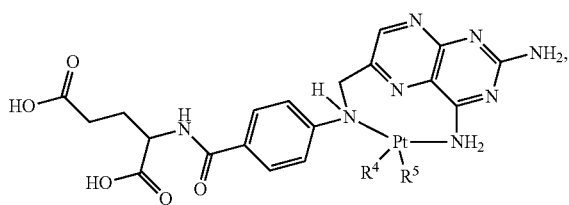

wherein $R^3$, $R^4$, and $R^5$ are as described herein, including embodiments. In embodiments, $R^3$ is H. In embodiments, $R^3$ is —CH$_3$.

In embodiments, the compound has the formula:

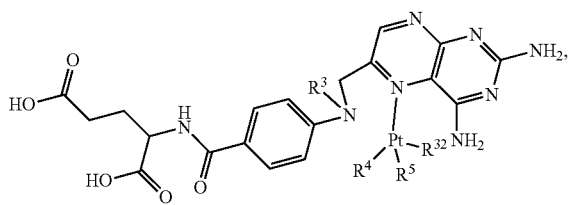

wherein $R^3$, $R^4$, $R^5$ and $R^{32}$ are as described herein, including embodiments. In embodiments, $R^3$ is H. In embodiments, $R^3$ is —CH$_3$.

In embodiments, the compound has the formula:

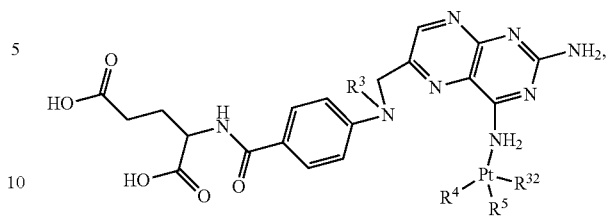

wherein $R^3$, $R^4$, $R^5$ and $R^{32}$ are as described herein, including embodiments. In embodiments, $R^3$ is H. In embodiments, $R^3$ is —CH$_3$.

In embodiments, the compound has the formula:

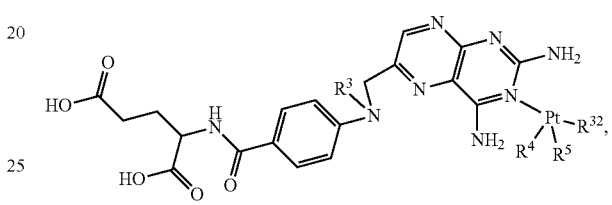

wherein $R^3$, $R^4$, $R^5$ and $R^{32}$ are as described herein, including embodiments. In embodiments, $R^3$ is H. In embodiments, $R^3$ is —CH$_3$.

In embodiments, the compound has the formula:

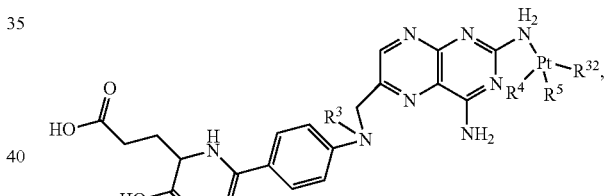

wherein $R^3$, $R^4$, $R^5$ and $R^{32}$ are as described herein, including embodiments. In embodiments, $R^3$ is H. In embodiments, $R^3$ is —CH$_3$.

In embodiments, the compound has the formula:

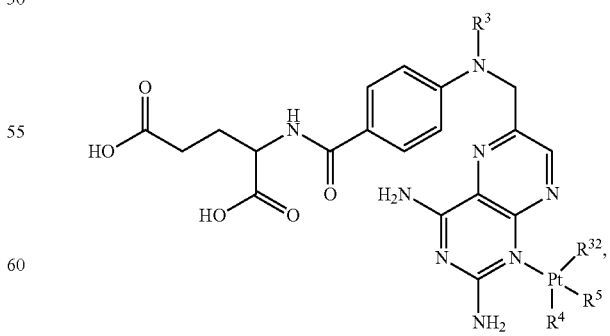

wherein $R^3$, $R^4$, $R^5$ and $R^{32}$ are as described herein, including embodiments. In embodiments, $R^3$ is H. In embodiments, $R^3$ is —CH$_3$.

In embodiments, the compound has the formula:

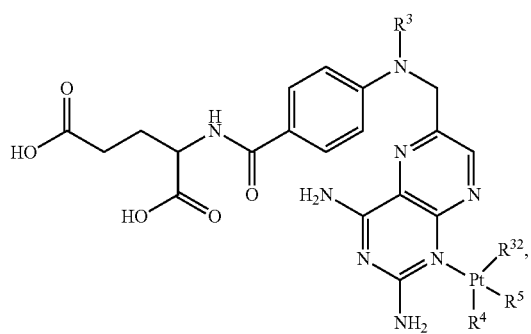

wherein $R^3$, $R^4$, $R^5$ and $R^{32}$ are as described herein, including embodiments. In embodiments, $R^3$ is H. In embodiments, $R^3$ is —$CH_3$.

In embodiments, the compound has the formula:

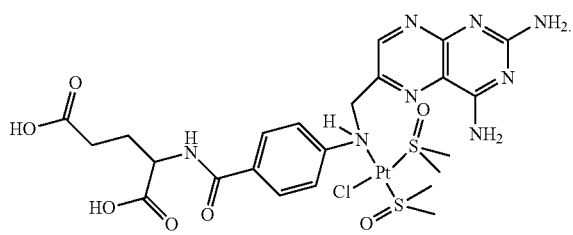

In embodiments, the compound has the formula:

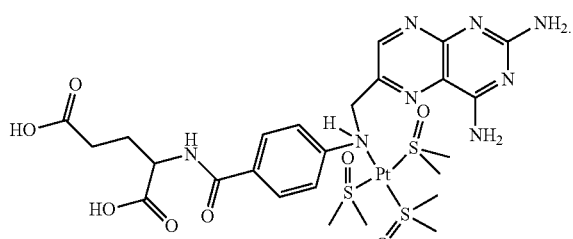

In embodiments, the compound has the formula:

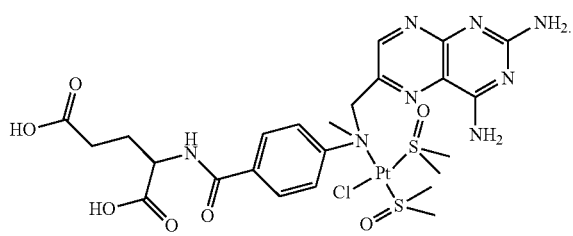

In embodiments, the compound has the formula:

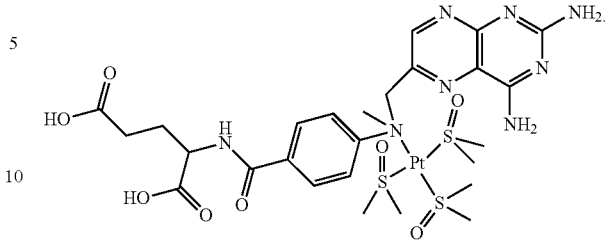

In embodiments, the compound has the formula:

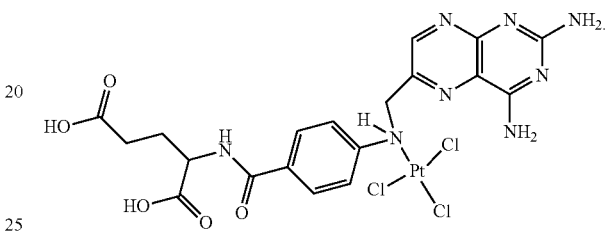

In embodiments, the compound has the formula:

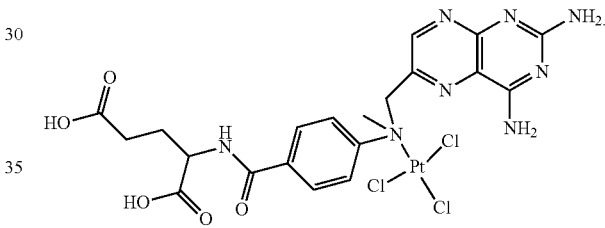

In embodiments, the compound has the formula:

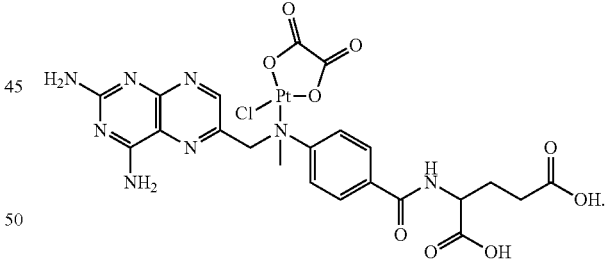

In embodiments, the compound has the formula:

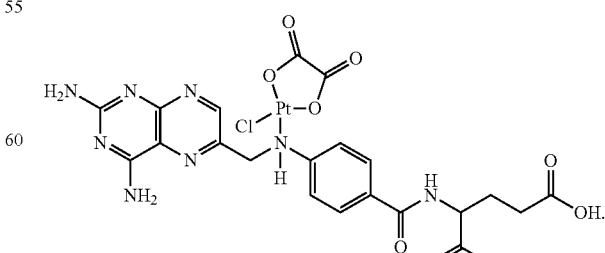

In embodiments, the compound has the formula:

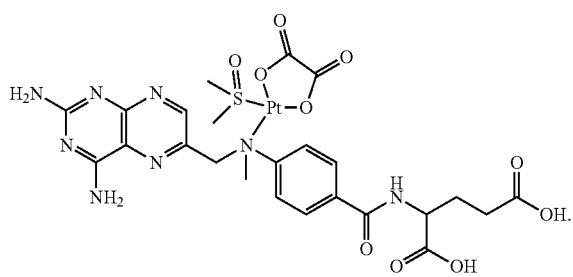

In embodiments, the compound has the formula:

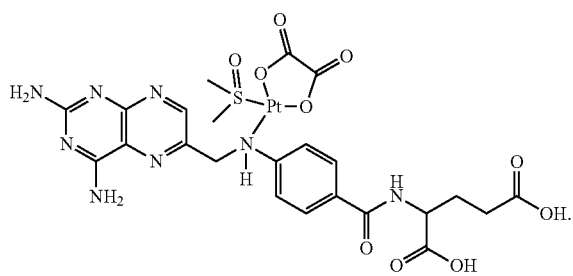

In embodiments, the compound has the formula:

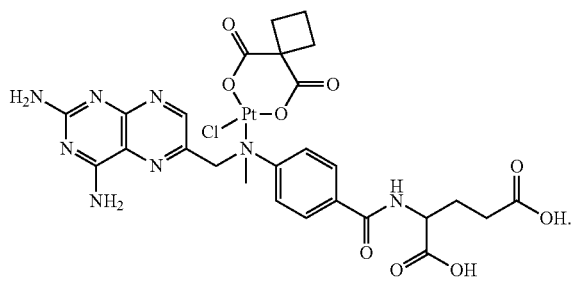

In embodiments, the compound has the formula:

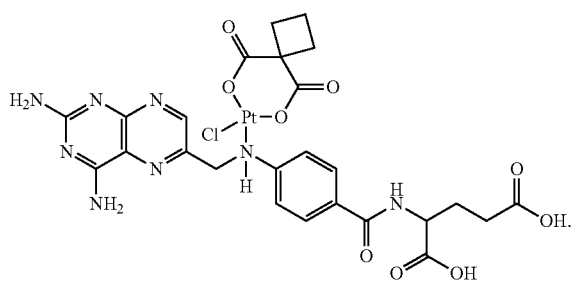

In embodiments, the compound has the formula:

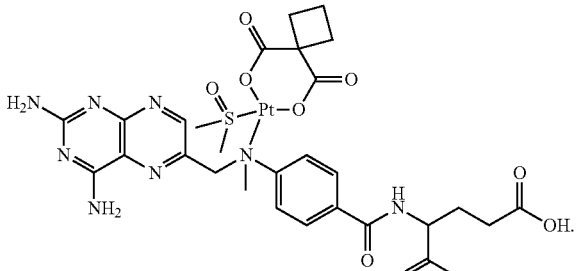

In embodiments, the compound has the formula:

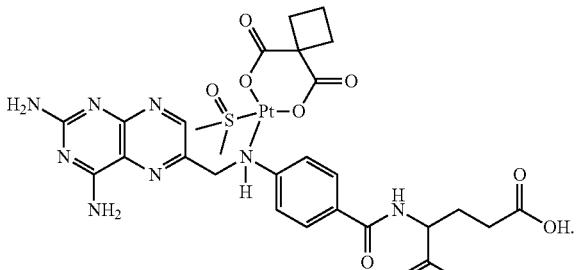

In embodiments, $R^6$, $R^7$, $R^8$, $R^9$, $R^{10}$, $R^{11}$, $R^{12}$, and $R^{13}$ are independently hydrogen, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^6$ and $R^7$ substituents bonded to the same nitrogen atom may optionally be joined to form a substituted or unsubstituted heterocycloalkyl (e.g. 3 to 8 membered heterocycloalkyl, 4 to 8 membered heterocycloalkyl, or 5 to 6 membered heterocycloalkyl) or substituted or unsubstituted heteroaryl (e.g. 5 to 10 membered heteroaryl, 5 to 9 membered heteroaryl, or 5 to 6 membered heteroaryl); $R^{11}$ and $R^{12}$ substituents bonded to the same nitrogen atom may optionally be joined to form a substituted or unsubstituted heterocycloalkyl (e.g. 3 to 8 membered heterocycloalkyl, 4 to 8 membered heterocycloalkyl, or 5 to 6 membered heterocycloalkyl) or substituted or unsubstituted heteroaryl (e.g. 5 to 10 membered heteroaryl, 5 to 9 membered heteroaryl, or 5 to 6 membered heteroaryl).

In embodiments, $R^6$ is independently hydrogen, oxo, halogen, —$CF_3$, —CN, —OH, —$NH_2$, —COOH, —$CONH_2$, —$NO_2$, —SH, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{16}$-substituted or unsubstituted alkyl (e.g. $C_1$-$C_8$ alkyl, $C_1$-$C_6$ alkyl, or $C_1$-$C_4$ alkyl), $R^{16}$-substituted or unsubstituted heteroalkyl (e.g. 2 to 8 membered heteroalkyl, 2 to 6 membered heteroalkyl, or 2 to 4 membered heteroalkyl), $R^{16}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{16}$-substituted or unsubstituted heterocycloalkyl (e.g. 3 to 8 membered heterocycloalkyl, 4 to 8 membered heterocycloalkyl, or 5 to 6 membered heterocycloalkyl), $R^{16}$-substituted or unsubstituted aryl (e.g. $C_6$-$C_{10}$ aryl or $C_6$ aryl), or $R^{16}$-substituted or unsubstituted heteroaryl (e.g. 5 to 10 membered heteroaryl, 5 to 9 membered heteroaryl, or 5 to 6 membered heteroaryl).

$R^{16}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{17}$-substituted or unsubstituted alkyl (e.g. $C_1$-$C_8$ alkyl, $C_1$-$C_6$ alkyl, or $C_1$-$C_4$ alkyl), $R^{17}$-substituted or unsubstituted heteroalkyl (e.g. 2 to 8 membered heteroalkyl, 2 to 6 membered heteroalkyl, or 2 to 4 membered heteroalkyl), $R^{17}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{17}$-substituted or unsubstituted heterocycloalkyl (e.g. 3 to 8 membered heterocycloalkyl, 4 to 8 membered heterocycloalkyl, or 5 to 6 membered heterocycloalkyl), $R^{17}$-substituted or unsubstituted aryl (e.g. $C_6$-$C_{10}$ aryl or $C_6$ aryl), or $R^{17}$-substituted or unsubstituted heteroaryl (e.g. 5 to 10 membered heteroaryl, 5 to 9 membered heteroaryl, or 5 to 6 membered heteroaryl).

In embodiments, $R^7$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{18}$-substituted or unsubstituted alkyl (e.g. $C_1$-$C_8$ alkyl, $C_1$-$C_6$ alkyl, or $C_1$-$C_4$ alkyl), $R^{18}$-substituted or unsubstituted heteroalkyl (e.g. 2 to 8 membered heteroalkyl, 2 to 6 membered heteroalkyl, or 2 to 4 membered heteroalkyl), $R^{18}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{18}$-substituted or unsubstituted heterocycloalkyl (e.g. 3 to 8 membered heterocycloalkyl, 4 to 8 membered heterocycloalkyl, or 5 to 6 membered heterocycloalkyl), $R^{18}$-substituted or unsubstituted aryl (e.g. $C_6$-$C_{10}$ aryl or $C_6$ aryl), or $R^{18}$-substituted or unsubstituted heteroaryl (e.g. 5 to 10 membered heteroaryl, 5 to 9 membered heteroaryl, or 5 to 6 membered heteroaryl). In embodiments, $R^7$ is a $R^{18}$-substituted $C_1$-$C_8$ alkyl. In embodiments, $R^7$ is a $R^{18}$-substituted $C_1$-$C_4$ alkyl. In embodiments, $R^7$ is a $R^{18}$-substituted $C_1$-$C_3$ alkyl. In embodiments, $R^7$ is a $R^{18}$-substituted $C_2$-$C_4$ alkyl. In embodiments, $R^7$ is substituted with oxo, —OH, or —COOH. In embodiments, $R^7$ is substituted with oxo. In embodiments, $R^7$ is substituted with —OH. In embodiments, $R^7$ is substituted with —COOH.

$R^{18}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{19}$-substituted or unsubstituted alkyl (e.g. $C_1$-$C_8$ alkyl, $C_1$-$C_6$ alkyl, or $C_1$-$C_4$ alkyl), $R^{19}$-substituted or unsubstituted heteroalkyl (e.g. 2 to 8 membered heteroalkyl, 2 to 6 membered heteroalkyl, or 2 to 4 membered heteroalkyl), $R^{19}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{19}$-substituted or unsubstituted heterocycloalkyl (e.g. 3 to 8 membered heterocycloalkyl, 4 to 8 membered heterocycloalkyl, or 5 to 6 membered heterocycloalkyl), $R^{19}$-substituted or unsubstituted aryl (e.g. $C_6$-$C_{10}$ aryl or $C_6$ aryl), or $R^{19}$-substituted or unsubstituted heteroaryl (e.g. 5 to 10 membered heteroaryl, 5 to 9 membered heteroaryl, or 5 to 6 membered heteroaryl).

In embodiments, $R^8$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{20}$-substituted or unsubstituted alkyl (e.g. $C_1$-$C_8$ alkyl, $C_1$-$C_6$ alkyl, or $C_1$-$C_4$ alkyl), $R^{20}$-substituted or unsubstituted heteroalkyl (e.g. 2 to 8 membered heteroalkyl, 2 to 6 membered heteroalkyl, or 2 to 4 membered heteroalkyl), $R^{20}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{20}$-substituted or unsubstituted heterocycloalkyl (e.g. 3 to 8 membered heterocycloalkyl, 4 to 8 membered heterocycloalkyl, or 5 to 6 membered heterocycloalkyl), $R^{20}$-substituted or unsubstituted aryl (e.g. $C_6$-$C_{10}$ aryl or $C_6$ aryl), or $R^{20}$-substituted or unsubstituted heteroaryl (e.g. 5 to 10 membered heteroaryl, 5 to 9 membered heteroaryl, or 5 to 6 membered heteroaryl).

$R^{20}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{21}$-substituted or unsubstituted alkyl (e.g. $C_1$-$C_8$ alkyl, $C_1$-$C_6$ alkyl, or $C_1$-$C_4$ alkyl), $R^{21}$-substituted or unsubstituted heteroalkyl (e.g. 2 to 8 membered heteroalkyl, 2 to 6 membered heteroalkyl, or 2 to 4 membered heteroalkyl), $R^{21}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{21}$-substituted or unsubstituted heterocycloalkyl (e.g. 3 to 8 membered heterocycloalkyl, 4 to 8 membered heterocycloalkyl, or 5 to 6 membered heterocycloalkyl), $R^{21}$-substituted or unsubstituted aryl (e.g. $C_6$-$C_{10}$ aryl or $C_6$ aryl), or $R^{21}$-substituted or unsubstituted heteroaryl (e.g. 5 to 10 membered heteroaryl, 5 to 9 membered heteroaryl, or 5 to 6 membered heteroaryl).

In embodiments, $R^9$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{22}$-substituted or unsubstituted alkyl (e.g. $C_1$-$C_8$ alkyl, $C_1$-$C_6$ alkyl, or $C_1$-$C_4$ alkyl), $R^{22}$-substituted or unsubstituted heteroalkyl (e.g. 2 to 8 membered heteroalkyl, 2 to 6 membered heteroalkyl, or 2 to 4 membered heteroalkyl), $R^{22}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{22}$-substituted or unsubstituted heterocycloalkyl (e.g. 3 to 8 membered heterocycloalkyl, 4 to 8 membered heterocycloalkyl, or 5 to 6 membered heterocycloalkyl), $R^{22}$-substituted or unsubstituted aryl (e.g. $C_6$-$C_{10}$ aryl or $C_6$ aryl), or $R^{22}$-substituted or unsubstituted heteroaryl (e.g. 5 to 10 membered heteroaryl, 5 to 9 membered heteroaryl, or 5 to 6 membered heteroaryl).

$R^{22}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{23}$-substituted or unsubstituted alkyl (e.g. $C_1$-$C_8$ alkyl, $C_1$-$C_6$ alkyl, or $C_1$-$C_4$ alkyl), $R^{23}$-substituted or unsubstituted heteroalkyl (e.g. 2 to 8 membered heteroalkyl, 2 to 6 membered heteroalkyl, or 2 to 4 membered heteroalkyl), $R^{23}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{23}$-substituted or unsubstituted heterocycloalkyl (e.g. 3 to 8 membered heterocyclocloalkyl, 4 to 8 membered heterocycloalkyl, or 5 to 6 membered heterocycloalkyl), $R^{23}$-substituted or unsubstituted aryl (e.g. $C_6$-$C_{10}$ aryl or $C_6$ aryl), or $R^{23}$-substituted or unsubstituted heteroaryl (e.g. 5 to 10 membered heteroaryl, 5 to 9 membered heteroaryl, or 5 to 6 membered heteroaryl).

In embodiments, $R^{10}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{24}$-substituted or unsubstituted alkyl (e.g. $C_1$-$C_8$ alkyl, $C_1$-$C_6$ alkyl, or $C_1$-$C_4$ alkyl), $R^{24}$-substituted or unsubstituted heteroalkyl (e.g. 2 to 8 membered heteroalkyl, 2 to 6 membered heteroalkyl, or 2 to 4 membered heteroalkyl), $R^{24}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{24}$-substituted or unsubstituted heterocycloalkyl (e.g. 3 to 8 membered heterocycloalkyl, 4 to 8 membered heterocycloalkyl, or 5 to 6 membered heterocycloalkyl), $R^{24}$-substituted or unsubstituted aryl (e.g. $C_6$-$C_{10}$ aryl or $C_6$ aryl), or $R^{24}$-substituted or unsubstituted heteroaryl (e.g. 5 to 10 membered heteroaryl, 5 to 9 membered heteroaryl, or 5 to 6 membered heteroaryl).

$R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{25}$-substituted or unsubstituted alkyl (e.g. $C_1$-$C_8$ alkyl, $C_1$-$C_6$ alkyl, or $C_1$-$C_4$ alkyl), $R^{25}$-substituted or unsubstituted heteroalkyl (e.g. 2 to 8 membered heteroalkyl, 2 to 6 membered heteroalkyl, or 2 to 4 membered heteroalkyl), $R^{25}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{25}$-substituted or unsubstituted heterocycloalkyl (e.g. 3 to 8 membered heterocycloalkyl, 4 to 8 membered heterocycloalkyl, or 5 to 6 membered heterocycloalkyl), $R^{25}$-substituted or unsubstituted aryl (e.g. $C_6$-$C_{10}$ aryl or $C_6$ aryl), or $R^{25}$-substituted or unsubstituted heteroaryl (e.g. 5 to 10 membered heteroaryl, 5 to 9 membered heteroaryl, or 5 to 6 membered heteroaryl).

In embodiments, R" is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{26}$-substituted or unsubstituted alkyl (e.g. $C_1$-$C_8$ alkyl, $C_1$-$C_6$ alkyl, or $C_1$-$C_4$ alkyl), $R^{26}$-substituted or unsubstituted heteroalkyl (e.g. 2 to 8 membered heteroalkyl, 2 to 6 membered heteroalkyl, or 2 to 4 membered heteroalkyl), $R^{26}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{26}$-substituted or unsubstituted heterocycloalkyl (e.g. 3 to 8 membered heterocycloalkyl, 4 to 8 membered heterocycloalkyl, or 5 to 6 membered heterocycloalkyl), $R^{26}$-substituted or unsubstituted aryl (e.g. $C_6$-$C_{10}$ aryl or $C_6$ aryl), or $R^{26}$-substituted or unsubstituted heteroaryl (e.g. 5 to 10 membered heteroaryl, 5 to 9 membered heteroaryl, or 5 to 6 membered heteroaryl).

$R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{27}$-substituted or unsubstituted alkyl (e.g. $C_1$-$C_8$ alkyl, $C_1$-$C_6$ alkyl, or $C_1$-$C_4$ alkyl), $R^{27}$-substituted or unsubstituted heteroalkyl (e.g. 2 to 8 membered heteroalkyl, 2 to 6 membered heteroalkyl, or 2 to 4 membered heteroalkyl), $R^{27}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{27}$-substituted or unsubstituted heterocycloalkyl (e.g. 3 to 8 membered heterocycloalkyl, 4 to 8 membered heterocycloalkyl, or 5 to 6 membered heterocycloalkyl), $R^{27}$-substituted or unsubstituted aryl (e.g. $C_6$-$C_{10}$ aryl or $C_6$ aryl), or $R^{27}$-substituted or unsubstituted heteroaryl (e.g. 5 to 10 membered heteroaryl, 5 to 9 membered heteroaryl, or 5 to 6 membered heteroaryl).

In embodiments, $R^{12}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{28}$-substituted or unsubstituted alkyl (e.g. $C_1$-$C_8$ alkyl, $C_1$-$C_6$ alkyl, or $C_1$-$C_4$ alkyl), $R^{28}$-substituted or unsubstituted heteroalkyl (e.g. 2 to 8 membered heteroalkyl, 2 to 6 membered heteroalkyl, or 2 to 4 membered heteroalkyl), $R^{28}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{28}$-substituted or unsubstituted heterocycloalkyl (e.g. 3 to 8 membered heterocycloalkyl, 4 to 8 membered heterocycloalkyl, or 5 to 6 membered heterocycloalkyl), $R^{28}$-substituted or unsubstituted aryl (e.g. $C_6$-$C_{10}$ aryl or $C_6$ aryl), or $R^{28}$-substituted or unsubstituted heteroaryl (e.g. 5 to 10 membered heteroaryl, 5 to 9 membered heteroaryl, or 5 to 6 membered heteroaryl).

$R^{28}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{29}$-substituted or unsubstituted alkyl (e.g. $C_1$-$C_8$ alkyl, $C_1$-$C_6$ alkyl, or $C_1$-$C_4$ alkyl), $R^{29}$-substituted or unsubstituted heteroalkyl (e.g. 2 to 8 membered heteroalkyl, 2 to 6 membered heteroalkyl, or 2 to 4 membered heteroalkyl), $R^{29}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{29}$-substituted or unsubstituted heterocycloalkyl (e.g. 3 to 8 membered heterocycloalkyl, 4 to 8 membered heterocycloalkyl, or 5 to 6 membered heterocycloalkyl), $R^{29}$-substituted or unsubstituted aryl (e.g. $C_6$-$C_{10}$ aryl or $C_6$ aryl), or $R^{29}$-substituted or unsubstituted heteroaryl (e.g. 5 to 10 membered heteroaryl, 5 to 9 membered heteroaryl, or 5 to 6 membered heteroaryl).

In embodiments, $R^{13}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl or $C_6$ aryl), or $R^{30}$-substituted or unsubstituted heteroaryl (e.g. 5 to 10 membered heteroaryl, 5 to 9 membered heteroaryl, or 5 to 6 membered heteroaryl).

$R^{30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{31}$-substituted or unsubstituted alkyl (e.g. $C_1$-$C_8$ alkyl, $C_1$-$C_6$ alkyl, or $C_1$-$C_4$ alkyl), $R^{31}$-substituted or unsubstituted heteroalkyl (e.g. 2 to 8 membered heteroalkyl, 2 to 6 membered heteroalkyl, or 2 to 4 membered heteroalkyl), $R^{31}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{31}$-substituted or unsubstituted heterocycloalkyl (e.g. 3 to 8 membered heterocycloalkyl, 4 to 8 membered heterocycloalkyl, or 5 to 6 membered heterocycloalkyl), $R^{31}$-substituted or unsubstituted aryl (e.g. $C_6$-$C_{10}$ aryl or $C_6$ aryl), or $R^{31}$-substituted or unsubstituted heteroaryl (e.g. 5 to 10 membered heteroaryl, 5 to 9 membered heteroaryl, or 5 to 6 membered heteroaryl).

$R^{15}$, $R^{17}$, $R^{19}$, $R^{21}$, $R^{23}$, $R^{25}$, $R^{27}$, $R^{29}$, and $R^{31}$, are independently oxo, halogen, —F, —Cl, —Br, —I, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, the symbol z is an integer from 0 to 4. In embodiments z is 1. In embodiments z is 2. In embodiments z is 3. In embodiments z is 4. In embodiments when z is 0, it is understood that $R^2$ is hydrogen. In embodiments, the symbol u is 1. In embodiments, the symbol u is 2. In embodiments, the symbol m is 1. In embodiments, the symbol m is 2. In embodiments, the symbol q is an integer from 0 to 4. In embodiments q is 1. In embodiments q is 2. In embodiments q is 3. In embodiments q is 4. In embodiments, $Y^1$ is —Cl. In embodiments, $Y^1$ is —Br. In embodiments, $Y^1$ is —I. In embodiments, $Y^1$ is —F. In embodiments, $Y^2$ is —Cl. In embodiments, $Y^2$ is —Br. In embodiments, $Y^2$ is —I. In embodiments, $Y^2$ is —F. In embodiments, $Y^3$ is —Cl. In embodiments, $Y^3$ is —Br. In embodiments, $Y^3$ is —I. In embodiments, $Y^3$ is —F. In embodiments, n1 is 1. In embodiments, n1 is 2. In embodiments, n1 is 3. In embodiments, n1 is 4. In embodiments, n1 is 5. In embodiments, n1 is 6. In embodiments, n1 is 7. In embodiments, n1 is 8.

For the compounds described herein, a person of ordinary skill in the art will immediately recognize that the nitrogen bound to the platinum may be positively charged. The nitrogen bound to the platinum refers to the nitrogen indicated by the asterisk in the structure below:

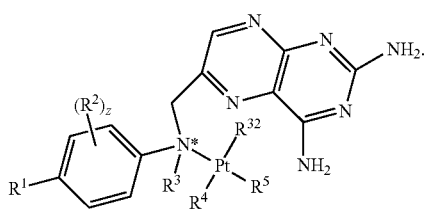

In embodiments, the nitrogen is attached to the platinum as a coordinate ligand. In other embodiments, the nitrogen is attached to the platinum as a counter ion. Where the nitrogen is attached to the platinum as a counter ion, a person of skill in the art will immediately understand that the nitrogen is formally positively charged.

In embodiments, the compound has the formula:

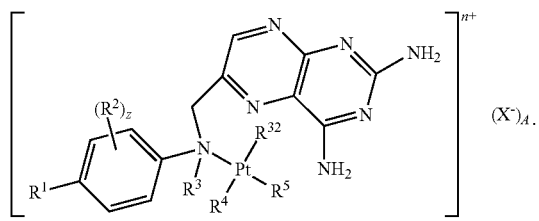

$R^1$, $R^2$, $R^3$, $R^4$, and $R^5$, are as described herein. X is a counterion and the symbols A and n are independently an integer from 0 to 2. In embodiments, the counterion is a halogen, acetate, camsylate, formate, fumarate, maleate, mesylate, oxalate, phosphate, tartrate, thiocyanate, nitrate, sulfate, PF$_6$, BF$_4$, BPh$_4$, triflate, tosylate, methanesulfonate, perchlorate, or fluorinated tetraarylborate.

In embodiments, the compound has the formula:

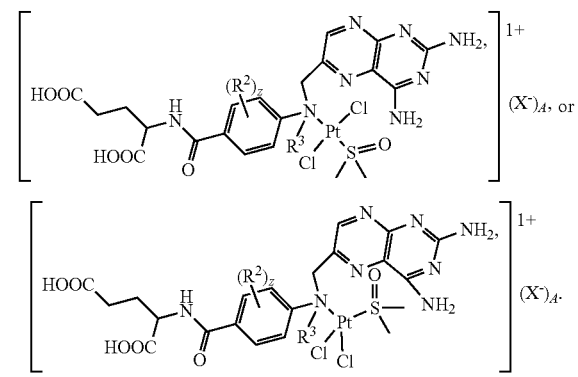

In an aspect is provided a compound, or a pharmaceutically acceptable salt thereof, having the formula:

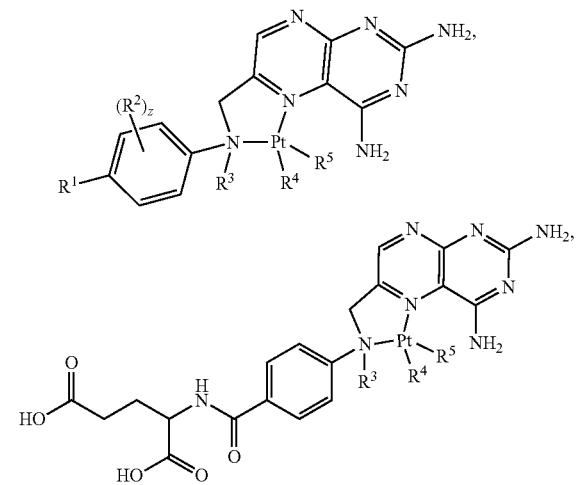

-continued
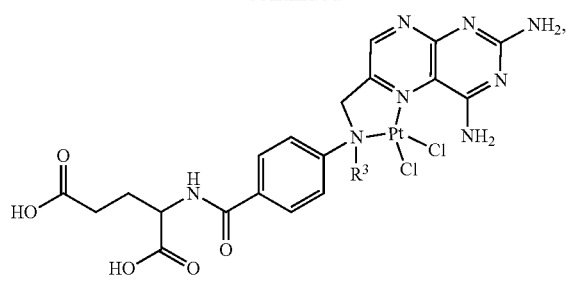
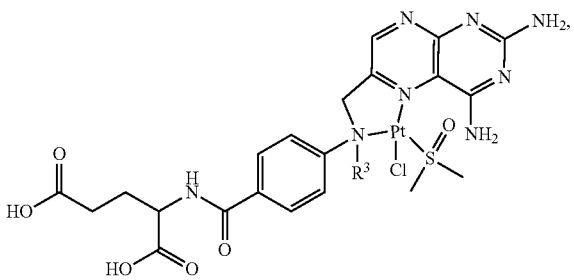
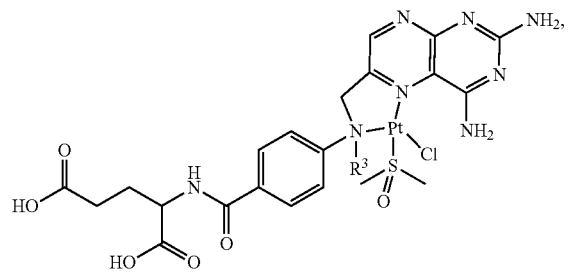
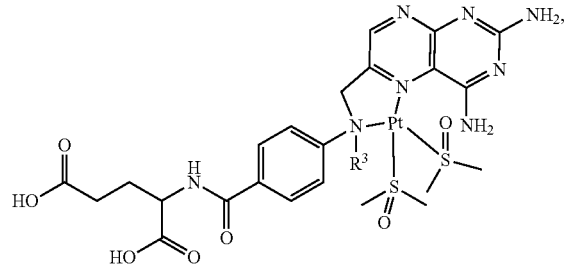
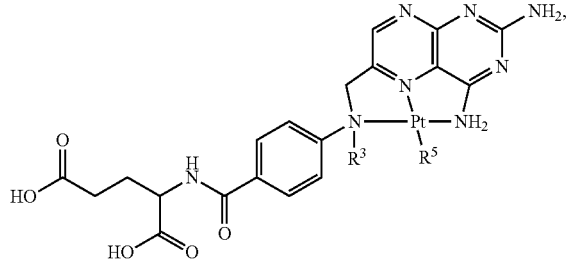
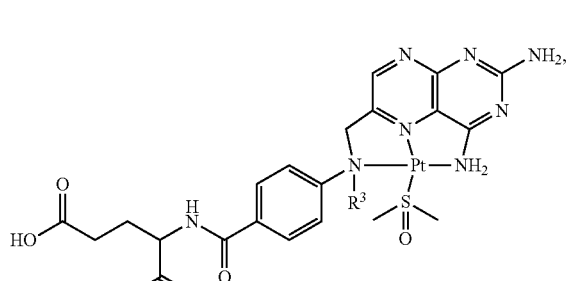
-continued
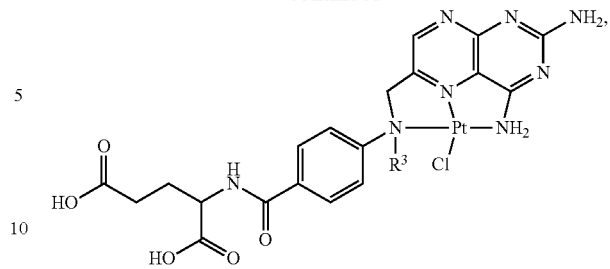
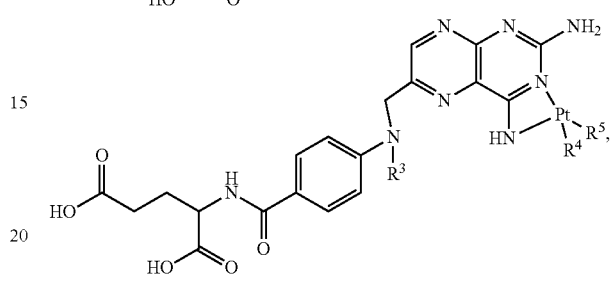
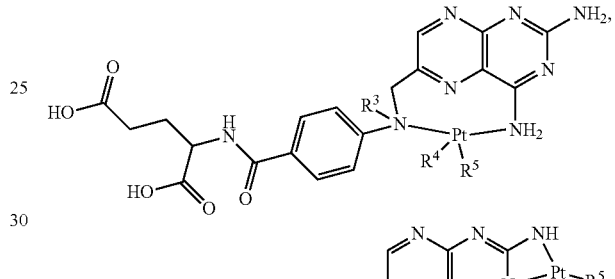
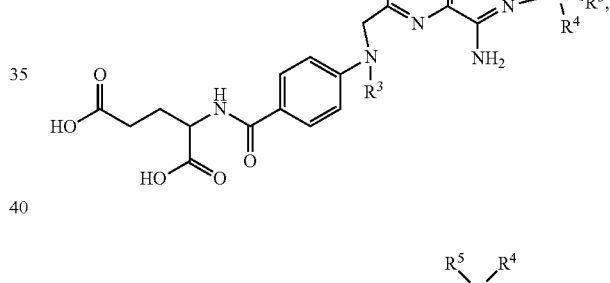
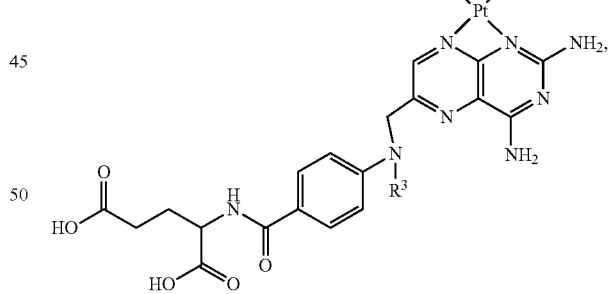
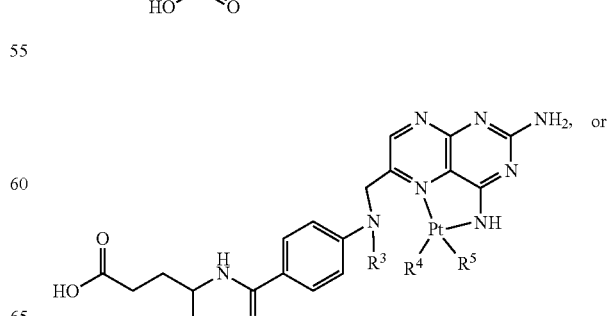

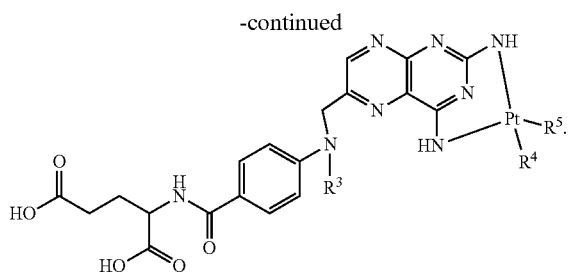

In embodiments, $R^1$ is independently halogen, $-CY^1_3$, $-CN$, $-OH$, $-NH_2$, $-COOH$, $-CONH_2$, $-NO_2$, $-SH$, $-SO_3H$, $-SO_4H$, $-SO_2NH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCY^1_3$, $-OCHY^1_2$, $-OCF_3$, $-SR^9$, $-OSO_2R^8$, $-OSO_3H$, $-NH_2NH_2$, $-ONR^6R^7$, $-NH_2C=(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently halogen, $-CN$, $-OH$, $-COOH$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCY^2_3$, $-OCHY^2_2$, $-OCF_3$, $-CY^2_3$, $-SO_qR^{10}$, $-SO-NR^{11}R^{12}$, $-ONR^{11}R^{12}$, $-NHC=(O)NR^{11}R^{12}$, $-N(O)_m$, $-NR^{11}R^{12}$, $-C(O)-OR^{13}$, $-C(O)-OR^{13}$, $-C(O)NR^{11}R^{12}$, $-OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^3$ is an unsubstituted $C_1$-$C_4$ alkyl or hydrogen. In embodiments, $R^4$ and $R^5$ are independently halogen, dimethyl sulfoxide, $-H_2O$, $-N_3$, $-NH_3$, $-SCN$, $-CN$, $-OH$, thiosulfate, or unsubstituted alkyl (e.g. $C_1$-$C_4$ alkyl). $R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl. In embodiments, $R^6$, $R^7$, $R^8$, $R^9$, $R^{10}$, $R^{11}$, $R^{12}$, and $R^{13}$ are independently hydrogen, halogen, $-CY^3_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCY^3_3$, $-OCHY^3_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ and $R^7$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. The symbol z is an integer from 0 to 4. The symbol u is independently an integer from 1 to 2, the symbol m is independently an integer from 1 to 2, and the symbol q is independently an integer from 0 to 4. The symbol $Y^1$ is independently $-Cl$, $-Br$, $-I$, or $-F$. The symbol $Y^2$ is independently $-Cl$, $-Br$, $-I$, or $-F$. The symbol $Y^3$ is independently $-Cl$, $-Br$, $-I$, or $-F$.

For the compounds described herein, a person of ordinary skill in the art will immediately recognize that the two nitrogens bound to the platinum may be positively charged. The two nitrogens bound to the platinum refers to the nitrogens indicated by asterisks in the structure below:

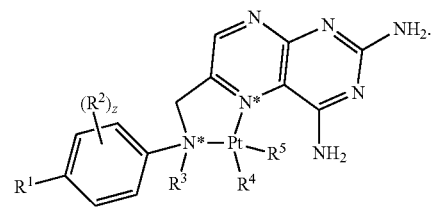

In embodiments, the nitrogens are attached to the platinum as coordinate ligands. In other embodiments, the nitrogens are attached to the platinum as counter ions. Where the nitrogen is attached to the platinum as a counter ion, a person of skill in the art will immediately understand that the nitrogens are formally positively charged.

In embodiments, the compound has the formula:

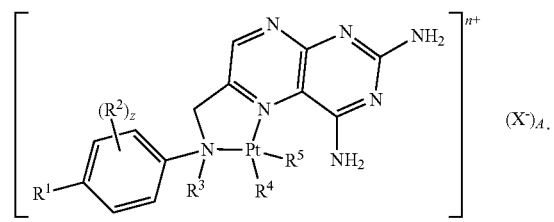

$R^1$, $R^2$, $R^3$, $R^4$, and $R^5$, are as described herein. X is a counterion and the symbols A and n are independently an integer from 0 to 2. In embodiments, the counterion is a halogen, acetate, camsylate, formate, fumarate, maleate, mesylate, oxalate, phosphate, tartrate, thiocyanate, nitrate, sulfate, $PF_6$, $BF_4$, $BPh_4$, triflate, tosylate, methanesulfonate, perchlorate, or fluorinated tetraarylborates.

In embodiments, the compound has the formula:

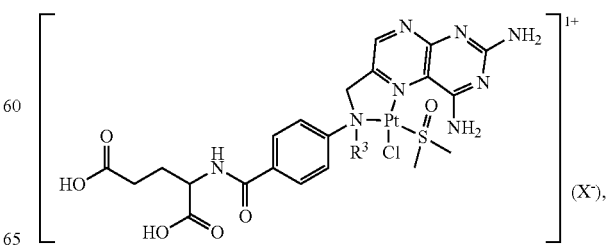

-continued

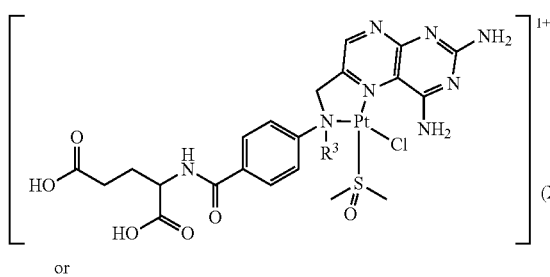
(S3)

or

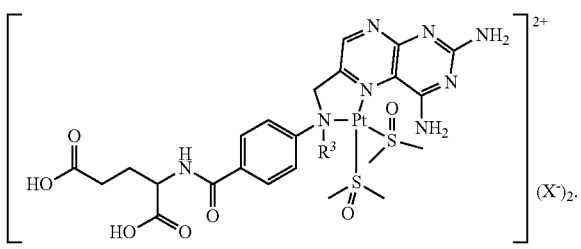
(S4)

$R^3$ and X are as described herein.

In embodiments, the compound has the formula:

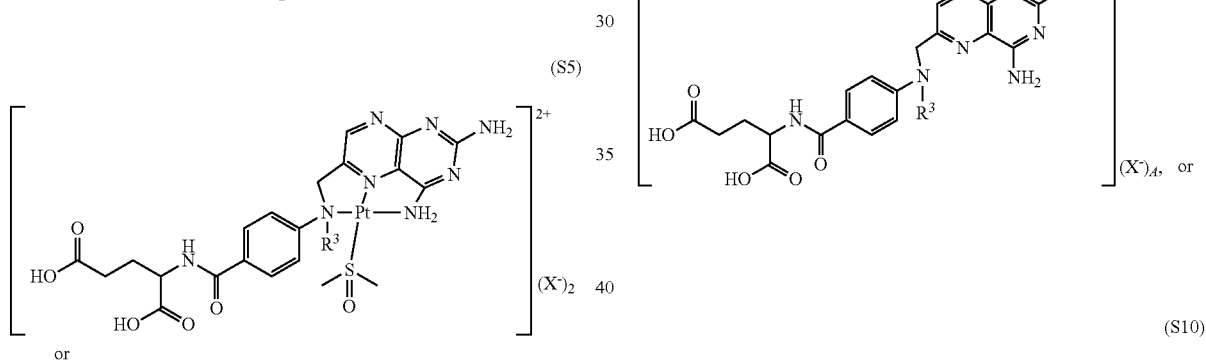
(S5)

or (S6)

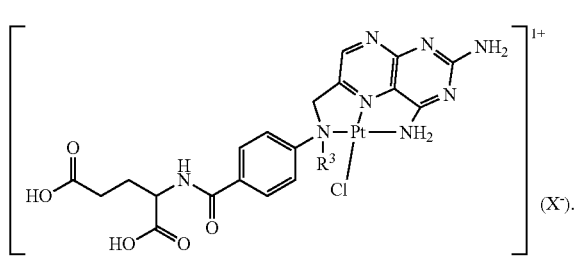

$R^3$ and X are as described herein.

In embodiments, the compound has the formula:

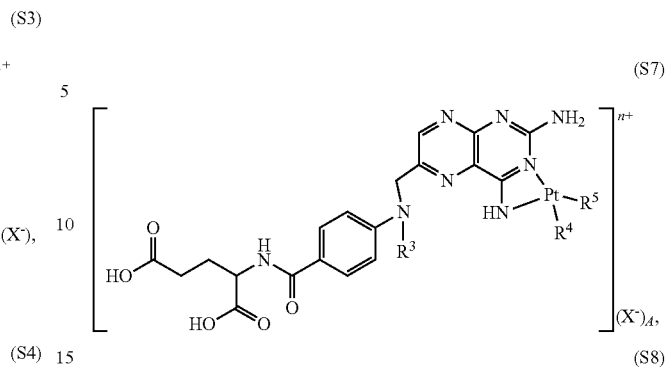
(S7)

(S8)

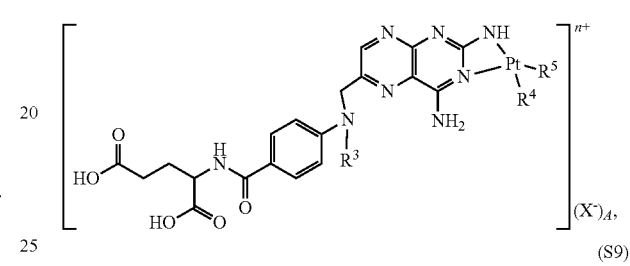
(S9)

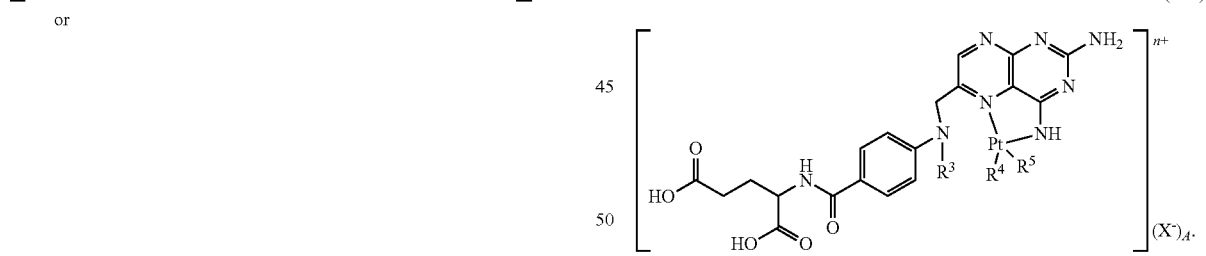
(S10)

$R^3$, $R^4$, $R^5$, X, A, and n are as described herein.

In embodiments, the platinum-based compound (e.g. a compound described herein) includes one platinum ion in either the +2 or the +4 oxidation state. The nature of ligand attachment to the Pt ion may be an ionic bond or a dative/covalent-coordinate bond. In embodiments, ionic bonds may be present bridging ligands or the Pt containing compound and a counterion without the involvement of the platinum ion in the said bridging unit.

In embodiments, $R^4$ is not —$NH_3$. In embodiments, $R^5$ is not —$NH_3$. In embodiments, $R^4$ is not —$H_2O$. In embodiments, $R^5$ is not —$H_2O$. In embodiments, $R^4$ and $R^5$ are not —$NH_3$.

In embodiments, the compound is not

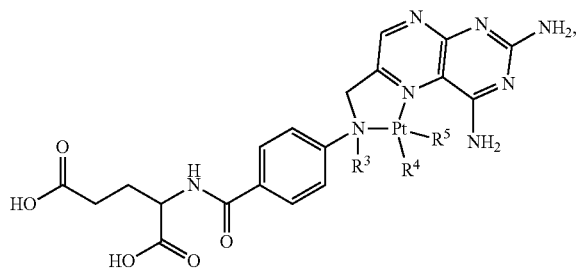

wherein R³ is as described herein, R⁴ and R⁵ are NH₃.

In embodiments, the compound is not

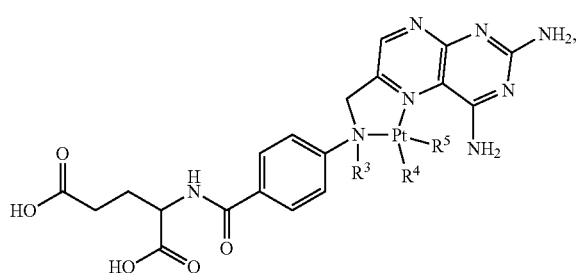

wherein R³ is as described herein, R⁴ and R⁵ are NH₂.

In an aspect is provided a compound having the formula:

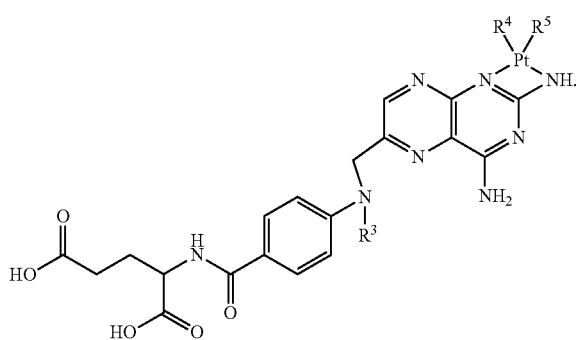

R³, R⁴, and R⁵ are as described herein.

In embodiments, the compound has the formula:

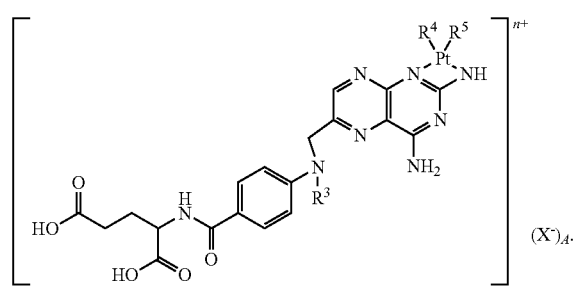

R³, R⁴, R⁵, X, A, and n are as described herein.

In embodiments, the compound is complexed (through bonds other than those to R⁴, R⁵, and R³²) to the platinum at non-leaving positions. In embodiments, the platinum and remainder of the compound not including R⁴, R⁵, and R³² do not dissociate in the cell. In embodiments, the platinum and remainder of the compound not including R⁴, R⁵, and R³² dissociate very slowly in the cell. In embodiments, the compound inhibits uptake of methotrexate by a cell (e.g., through a folate transporter) with an IC50 of 100 μM or better (e.g., 1, 2, 3, 4, 5, 6, 7, 8, 9, 10, 20, 30, 40, 50, 60, 70, 80, 90, or 100 or better (lower IC50)). In embodiments, the compound binds DHFR with a dissociation constant (Kd) of 10 μM or weaker (e.g., 10, 20, 30, 40, 50, 60, 70, 80, 90, 100, 200, 300, 400, 500, 600, 700, 800, 900, or 1000 or weaker). In embodiments, the compound has a Km for DHFR of 10 μM or weaker (e.g., 10, 20, 30, 40, 50, 60, 70, 80, 90, 100, 200, 300, 400, 500, 600, 700, 800, 900, or 1000 or weaker).

In embodiments, the toxicity of a compound described herein is reduced by folinate. In embodiments, the compound described herein is capable of forming a platinum-DNA adduct. In embodiments, a compound described herein is a modulator of a folic acid transporter. In embodiments, a compound described herein is not a modulator of a folic acid transporter. In embodiments, a compound described herein is an inhibitor of a folic acid transporter. In embodiments, a compound described herein is not an inhibitor of a folic acid transporter. In embodiments, a compound described herein is a modulator of DHFR. In embodiments, a compound described herein is not a modulator of DHFR. In embodiments, a compound described herein is an inhibitor of DHFR. In embodiments, a compound described herein is not an inhibitor of DHFR. In embodiments, a compound described herein is a modulator of a component of a cellular pathway that utilizes or modifies folic acid. In embodiments, a compound described herein is not a modulator of a component of a cellular pathway that utilizes or modifies folic acid. In embodiments, a compound described herein is an inhibitor of a component of a cellular pathway that utilizes or modifies folic acid. In embodiments, a compound described herein is not an inhibitor of a component of a cellular pathway that utilizes or modifies folic acid. The compounds, pharmaceutical compositions, and methods described herein are not bound by a particular mechanism and may function through a different or unknown mechanism while still being described herein.

In embodiments, the compound is

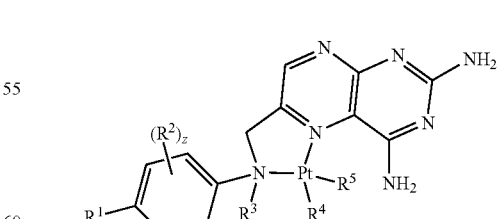

wherein R¹, R², z, R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide.

In embodiments, the compound is

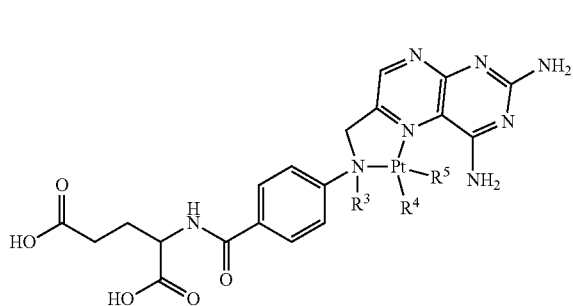

wherein $R^3$, $R^4$, and $R^5$ are as described herein, including embodiments. In embodiments, $R^3$ is H. In embodiments, $R^3$ is —CH$_3$. In embodiments, $R^4$ is Cl. In embodiments, $R^4$ and $R^5$ are Cl. In embodiments $R^4$ is Cl and $R^5$ is dimethyl sulfoxide. In embodiments, $R^4$ or $R^5$ is dimethyl sulfoxide (DMSO). In embodiments, the compound is

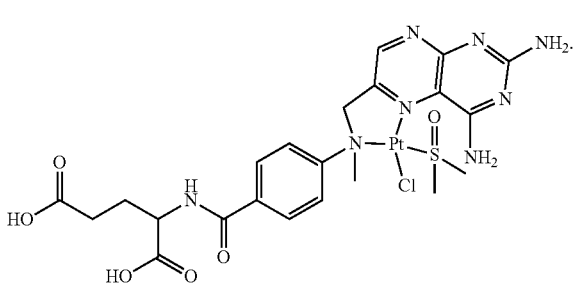

In embodiments, the compound is

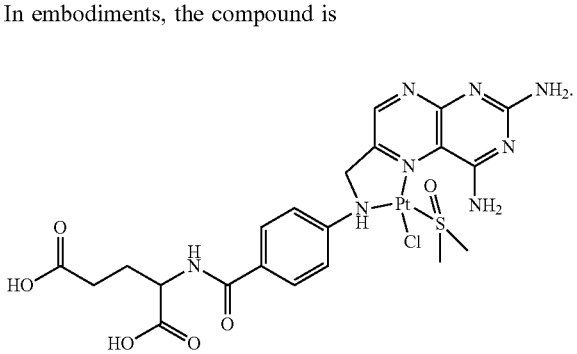

In embodiments, the compound is

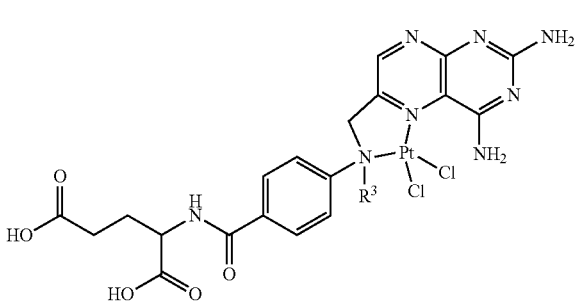

wherein $R^3$ is as described herein, including embodiments. In embodiments, $R^3$ is H. In embodiments, $R^3$ is —CH$_3$. In embodiments, the compound is

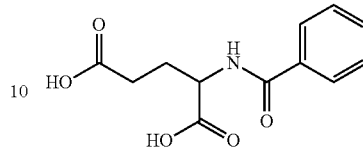

In embodiments, the compound is

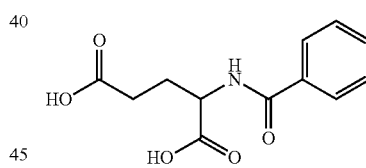

In embodiments, the compound is

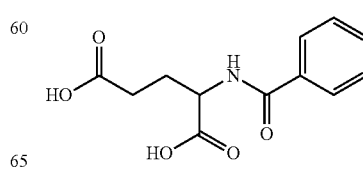

wherein $R^3$ is as described herein, including embodiments. In embodiments, $R^3$ is H. In embodiments, $R^3$ is —CH$_3$. In embodiments, the compound is In embodiments, the compound is

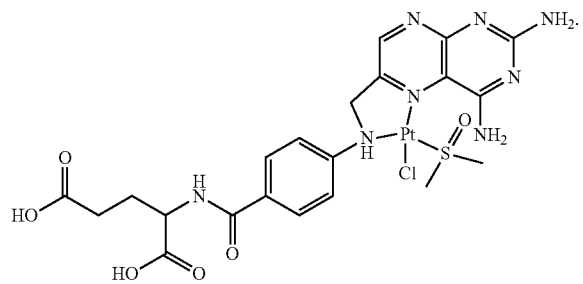

In embodiments, the compound is

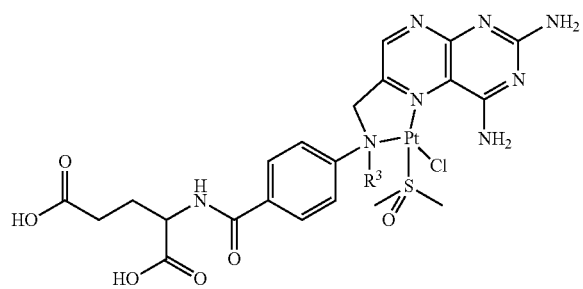

wherein R³ is as described herein, including embodiments. In embodiments, R³ is H. In embodiments, R³ is —CH₃. In embodiments, the compound is

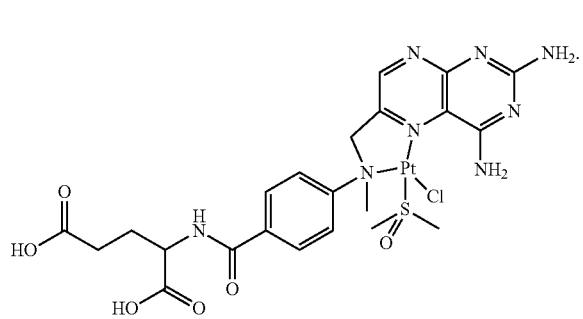

In embodiments, the compound is

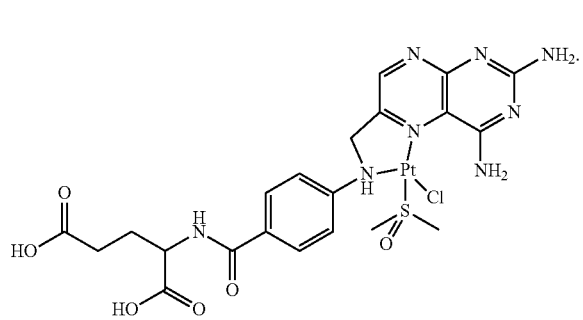

In embodiments, the compound is

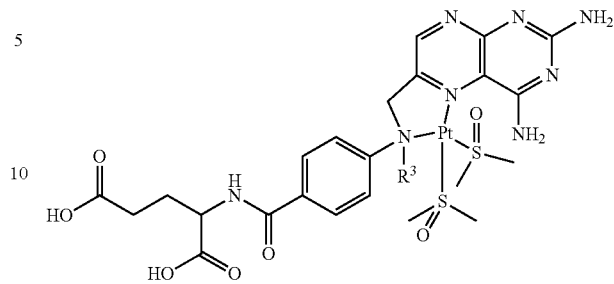

wherein R³ is as described herein, including embodiments. In embodiments, R³ is H. In embodiments, R³ is —CH₃. In embodiments, the compound is

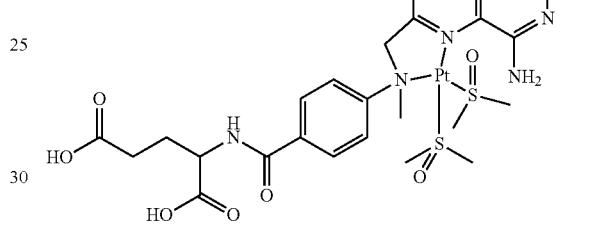

In embodiments, the compound is

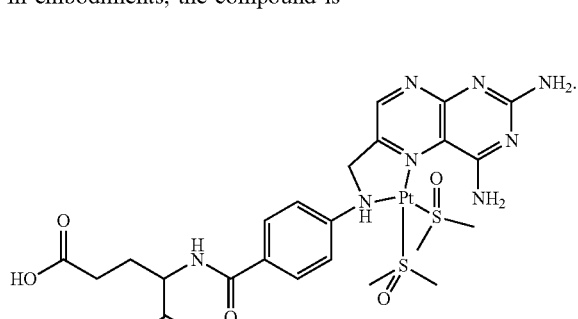

In embodiments, the compound is

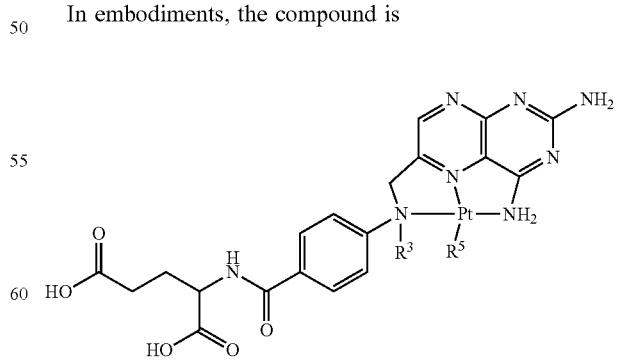

wherein R³ and R⁵ are is as described herein, including embodiments. In embodiments, R³ is H. In embodiments, R³ is —CH₃. In embodiments, the compound is

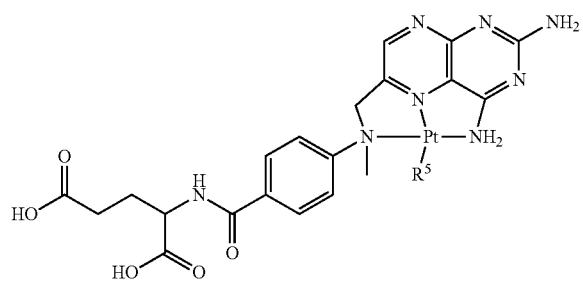

wherein $R^5$ is as described herein. In embodiments, the compound is

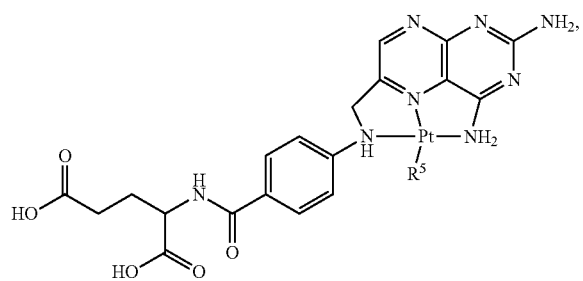

wherein $R^5$ is as described herein.
In embodiments, the compound is

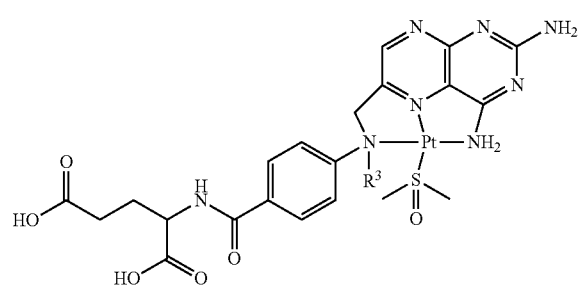

wherein $R^3$ is as described herein, including embodiments. In embodiments, $R^3$ is H. In embodiments, $R^3$ is —CH$_3$. In embodiments, the compound is

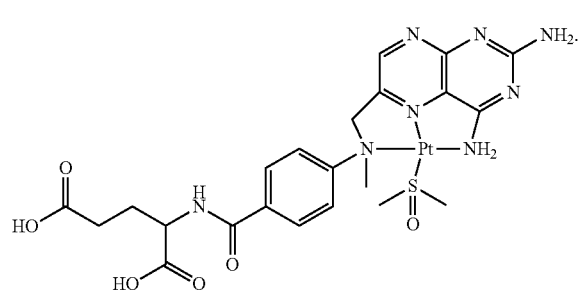

In embodiments, the compound is

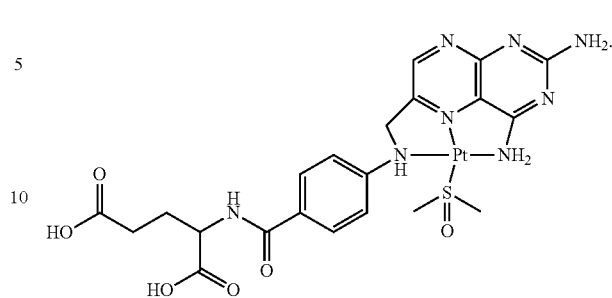

In embodiments, the compound is

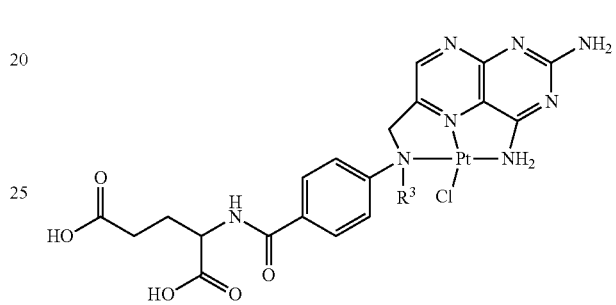

wherein $R^3$ is as described herein, including embodiments. In embodiments, $R^3$ is H. In embodiments, $R^3$ is —CH$_3$. In embodiments, the compound is

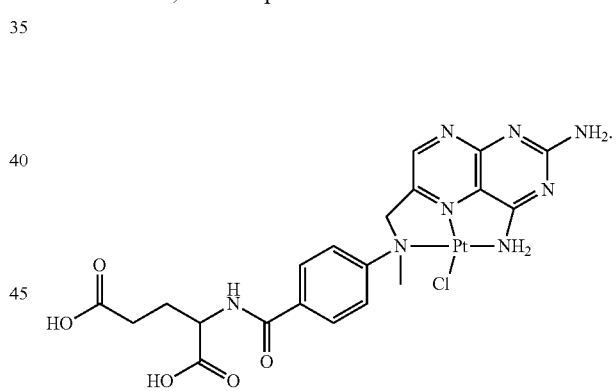

In embodiments, the compound is

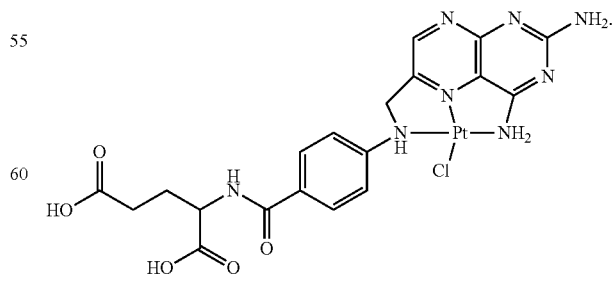

In embodiments, the compound is

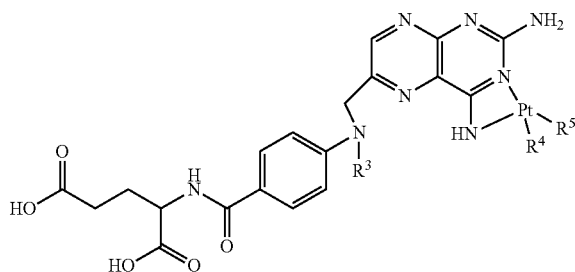

wherein R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide. In embodiments, the compound is

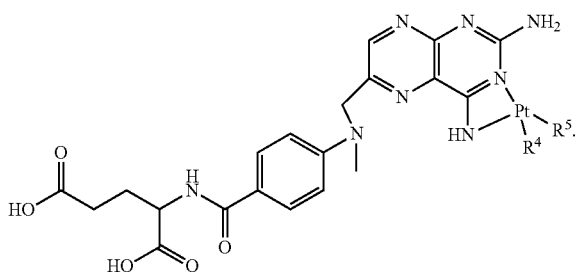

In embodiments, the compound is

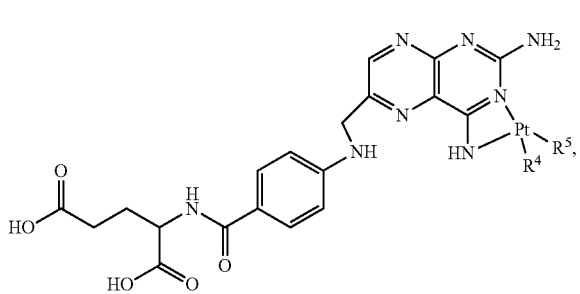

wherein R⁴, and R⁵ are as described herein, including embodiments. In embodiments, R⁴ is Cl. In embodiments, R⁴ and R⁵ are Cl. In embodiments R⁴ is Cl and R⁵ is dimethyl sulfoxide.
In embodiments, the compound is

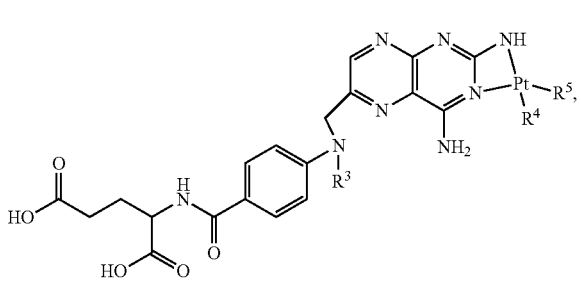

wherein R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide.

In embodiments, the compound is

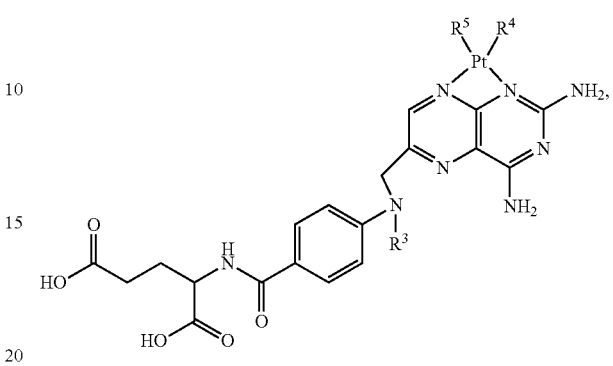

wherein R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide.

In embodiments, the compound is

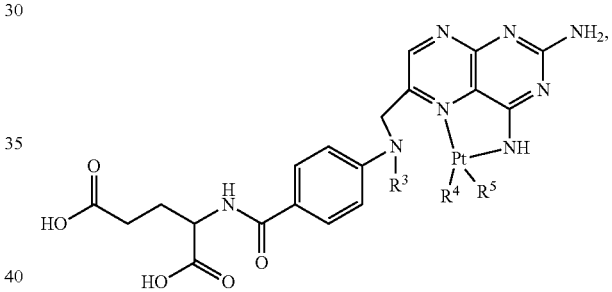

wherein R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide.

In embodiments, the compound is

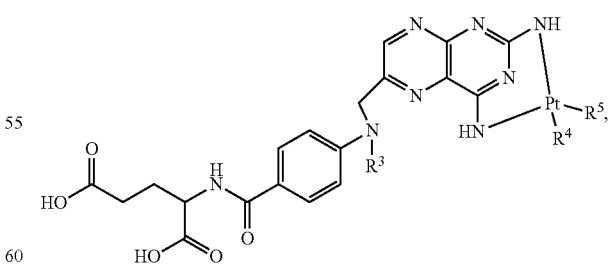

wherein R³, R⁴, and R⁵ are as described herein, including embodiments. In embodiments, R³ is H. In embodiments, R³ is —CH₃. In embodiments, R⁴ is Cl. In embodiments, R⁴ and R⁵ are Cl. In embodiments R⁴ is Cl and R⁵ is dimethyl sulfoxide.

III. Pharmaceutical Compositions

In another aspect, is provided a pharmaceutical composition including a pharmaceutically acceptable excipient and a compound as described herein or a pharmaceutically acceptable salt thereof.

The pharmaceutical compositions may include optical isomers, diastereomers, or pharmaceutically acceptable salts of the compounds disclosed herein. The compound included in the pharmaceutical composition may be covalently attached to a carrier moiety. Alternatively, the compound included in the pharmaceutical composition is not covalently linked to a carrier moiety.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of cancer symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., cancer, neuroblastoma, osteosarcoma, rhabdomyosarcoma, ovarian cancer, prostate cancer or pancreatic cancer, or other cancers that express folate transporters or organic anion transporters), kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

As described herein, molecules, compositions, and compounds such as platinum-based compounds or drugs that have been identified as substrates for one or more folate transporter proteins are useful in treating cancers that express folate transport proteins or nucleic acid. For therapeutic applications, the platinum-based compounds or drugs of the present invention can be administered alone or co-administered in combination with conventional chemotherapy, radiotherapy, hormonal therapy, and/or immunotherapy.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compositions described herein of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly include a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating a disease associated with cells expressing folate transporters (e.g. glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer), or with adjunctive agents that may not be effective alone, but may contribute to the efficacy of the active agent.

In embodiments, the platinum-based compositions and compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), other platinum-based compounds (e.g. cisplatin, oxaloplatin, carboplatin, a second platinum-based compound described herein), and the like.

The platinum-based compounds or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In a further embodiment, the platinum-based compounds or drugs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{90}$Y, $^{105}$Rh, $^{111}$Ag, $^{117m}$Sn, $^{149}$Pm, $^{153}$Sm, $^{166}$Ho, $^{177}$Lu, $^{186}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based compound or drug suspended in diluents, e.g., water, saline, or PEG 400; (b) capsules, sachets, or tablets, each containing a predetermined amount of a platinum-based compound or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a platinum-based compound or drug in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The platinum-based compound or drug of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged platinum-based compound or drug with a suppository base. Suitable suppository bases include natural or synthetic triglycerides or paraffin hydrocarbons. In addition, it is also possible to use gelatin rectal capsules which contain a combination of the platinum-based compound or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a platinum-based compound or drug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

IV. Methods of Use

In an aspect is provided a method of treating cancer in a patient in need of such treatment, wherein the method includes administering a therapeutically effective amount of a compound as described herein or a pharmaceutically acceptable salt thereof.

In embodiments, the cancer is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer. In embodiments, the cancer is glioblastoma, kidney cancer, cervical cancer, ovarian cancer, neuroblastoma, rhabdomyosarcoma, or osteosarcoma.

In embodiments, the cancer is osteosarcoma, neuroblastoma, or rhabdomyosarcoma. In embodiments, the cancer is breast cancer, central nervous system cancer, colon cancer, leukemia, melanoma, lung cancer (e.g., non-small cell lung cancer), ovarian cancer, prostate cancer, or renal cancer.

In embodiments, the cancer expresses folate transporters. In embodiments, the cancer is glioblastoma, kidney cancer, neuroblastoma, osteosarcoma, rhabdomyosarcoma, cervical cancer, ovarian cancer, prostate cancer or pancreatic cancer. In embodiments the disease is neuroblastoma. In embodiments the disease is osteosarcoma. In embodiments the disease is rhabdomyosarcoma. In embodiments the disease is ovarian cancer. In embodiments the disease is prostate cancer. In embodiments the disease is pancreatic cancer.

In embodiments, the method of treatment includes a method of measuring the levels of a transporter in a sample from a patient. In embodiments, the transporter is a folate transporter. In embodiments, the transporter is an organic anion transporter. In embodiments, the method of treatment includes a method of measuring the levels of folate transporters in a sample from a patient. In some embodiments, the sample from a patient includes cancer cells. In embodiments, the cancer cells express a transporter. In embodiments, the transporter is a folate transporter. In some embodiments, the method of treatment includes a method of measuring the levels of folate transporters in cancer cells in a sample from a patient. In some embodiments, the method of treatment includes administering a compound as described herein.

In embodiments, the compound or a pharmaceutically acceptable salt thereof as described herein binds to DNA. In embodiments, the compound or a pharmaceutically acceptable salt thereof as described herein inhibits DNA synthesis in cells. In embodiments, the compound or a pharmaceutically acceptable salt thereof as described herein forms both inter- and intra-strand cross links in DNA. In embodiments, the compound or a pharmaceutically acceptable salt thereof as described herein induces or forms cross links in DNA. In embodiments, the compound or a pharmaceutically acceptable salt thereof as described herein prevents DNA replication and/or transcription in cells. In embodiments, the compound or a pharmaceutically acceptable salt thereof as described herein inhibits DNA replication and/or transcription in cells. In embodiments, the compound or a pharmaceutically acceptable salt thereof as described herein disrupts productive DNA replication and/or transcription in cells. In embodiments, the compound or a pharmaceutically acceptable salt thereof as described herein reduces accurate DNA replication and/or transcription in cells. In embodiments, the cancer cells express genes involved in the folate pathway. In embodiments, the compound or a pharmaceutically acceptable salt thereof as described herein modulates components (e.g. dihydrofolate reductase, thymidylate synthetase, and/or folylpolyglutamate synthase) of the folate pathway. In embodiments, the compound or a pharmaceutically acceptable salt thereof as described herein inhibits components (e.g. dihydrofolate reductase, thymidylate synthetase, and/or folylpolyglutamate synthase) of the folate pathway. In embodiments, the compound or a pharmaceutically acceptable salt thereof as described herein activates components (e.g. dihydrofolate reductase, thymidylate synthetase, and/or folylpolyglutamate synthase) of the folate pathway. In embodiments, the compound or a pharmaceutically acceptable salt thereof as described herein forms an adduct with a component (e.g. dihydrofolate reductase, thymidylate synthetase, or folylpolyglutamate synthase) of the folate pathway. In embodiments, the compound or a pharmaceutically acceptable salt thereof as described herein complexes with a component (e.g. dihydrofolate reductase, thymidylate synthetase, or folylpolyglutamate synthase) of the folate pathway. In embodiments, the compound or a pharmaceutically acceptable salt thereof as described herein interacts weakly with DHFR. In embodiments, co-administration of folinate reduces cell toxicity (e.g., cancer cell toxicity) of a compound described herein. In embodiments, the compounds described herein does not inhibit DHFR. In embodiments, the compounds described herein weakly inhibit the enzyme (e.g., IC50>50 µM).

In a further aspect, is provided a method of inducing cell death in a cell, the method including contacting the cell with an effective amount of a compound as described herein or a pharmaceutically acceptable salt thereof.

In embodiments, the method includes use of a compound described herein. In embodiments, cell death is through apoptosis. In embodiments, the cell expresses a transporter. In embodiments, the transporter is a folate transporter. In embodiments the transporter is SLC19A1, SLC46A1, OAT1, OATS, OATP1A2, or OATP2B1. In embodiments, the cell expresses folate transporters. In embodiments, the transporter is an organic anion transporter. In some embodiments, the cell expresses organic anion transporters. In some embodiments, the cell is a cancer cell. In some embodiments, the cell is a metastatic cancer cell. In embodiments the transporter is SLC19A1. In embodiments the transporter is SLC46A1. In embodiments the transporter is OAT1. In embodiments the transporter is OAT3. In embodiments the transporter is OATP1A2. In embodiments the transporter is OATP2B1.

In an aspect is provided a method of treating cancer in a patient in need of such treatment, wherein the patient has cancer cells expressing a folate transporter protein or mRNA, the method including administering a therapeutically effective amount of a compound as described herein or a pharmaceutically acceptable salt thereof.

In embodiments, the method of treating includes administering a compound described herein including embodiments) or a pharmaceutically acceptable salt thereof. In embodiments, the cancer is glioblastoma, neuroblastoma, osteosarcoma, rhabdomyosarcoma, cervical cancer, ovarian cancer, prostate cancer or pancreatic cancer. In embodiments, the method includes a method of measuring the amount of a folate transporter protein or mRNA in a sample from the patient. In embodiments, the sample includes cancer cells. In embodiments, the cancer cells express a folate transporter protein or mRNA. In embodiments, the cancer cells express an organic anion transporter. In embodiments, the cancer cells express a folate transporter.

In an aspect is provided a method of treating cancer in a patient in need of such treatment, wherein the patient has cancer cells expressing an organic anion transporter protein or mRNA, the method including administering a therapeutically effective amount of a compound as described herein or a pharmaceutically acceptable salt thereof.

In embodiments, the method of treating includes administering a compound described herein. In embodiments, the cancer is glioblastoma, neuroblastoma, osteosarcoma, rhabdomyosarcoma, cervical cancer, ovarian cancer, prostate cancer or pancreatic cancer. In embodiments, the method includes a method of measuring the amount of an organic anion transporter protein or mRNA in a sample from the patient. In embodiments, the sample includes cancer cells. In embodiments, the cancer cells express a folate transporter protein or mRNA.

In an aspect is provided a method of inhibiting replication of DNA in a cell, the method including contacting the cell with an effective amount of a compound as described herein or a pharmaceutically acceptable salt thereof.

In an aspect is provided a method of crosslinking DNA in a cell, the method including contacting the cell with an effective amount of a compound as described herein or a pharmaceutically acceptable salt thereof.

In an aspect is provided a method of inhibiting replication of DNA in a cell, wherein the cell expresses a folate transporter protein or mRNA, the method including contacting the cell with an effective amount of a compound as described herein or a pharmaceutically acceptable salt thereof.

In an aspect is provided a method of inhibiting replication of DNA in a cell, wherein the cell expresses an organic anion transporter protein or mRNA, the method including contacting the cell with an effective amount of a compound as described herein or a pharmaceutically acceptable salt thereof.

In embodiments, the method includes inhibiting dihydrofolate reductase with the compound as described herein or a pharmaceutically acceptable salt thereof. In embodiments, the method does not include inhibiting dihydrofolate reductase with the compound as described herein or a pharmaceutically acceptable salt thereof.

In embodiments, the method includes contacting the cell with the compound as described herein or a pharmaceutically acceptable salt thereof. In embodiments, the method includes the use of a compound as described herein or a pharmaceutically acceptable salt thereof. In embodiments, the cell is a cancer cell. In embodiments, the cell is a neuroblastoma cancer cell. In embodiments, the cell is a glioblastoma cancer cell. In embodiments, the cell is a cervical cancer cell. In embodiments, the cell is a ovarian cancer cell. In embodiments, the cell is a kidney cancer cell. In embodiments, the cell is a rhabdomyosarcoma cancer cell. In embodiments, the cell is a osteosarcoma cancer cell. In embodiments, the cell is a brain cancer cell. In embodiments, the cell is a metastatic cancer cell.

In an aspect is provided a method of inducing cell death in a cell, wherein the cell expresses a folate transporter protein or mRNA, the method including contacting the cell with an effective amount of a compound as described herein or a pharmaceutically acceptable salt thereof.

In a further aspect is provided a method of inducing cell death in a cell, wherein the cell expresses proteins in the folic acid pathway (e.g., synthesis pathway or metabolic pathway or pathway using folic acid/folate as a reactant or precursor molecule), the method including contacting the cell with an effective amount of a compound as described herein. In embodiments, the compound described herein inhibits a component of the folic acid pathway (e.g., synthesis pathway or metabolic pathway or pathway using folic acid/folate as a reactant or precursor molecule). In embodiments, the compound described herein reduces the level of a component of the folic acid pathway (e.g., synthesis pathway or metabolic pathway or pathway using folic acid/folate as a reactant or precursor molecule). In embodiments, the compound described herein reduces the level of activity of a component of the folic acid pathway (e.g., synthesis pathway or metabolic pathway or pathway using folic acid/folate as a reactant or precursor molecule). In embodiments, the component is DHFR. In embodiments, the component is not DHFR. In embodiments, the compound modulates more than one component of the folic acid pathway (e.g., synthesis pathway or metabolic pathway or pathway using folic acid/folate as a reactant or precursor molecule).

In an aspect is provided a method of inducing cell death in a cell, wherein the cell expresses an organic anion transporter protein or mRNA, the method including contacting the cell with an effective amount of a compound as described herein or a pharmaceutically acceptable salt thereof.

In embodiments, the method includes contacting the cell with an effective amount of a compound as described herein or a pharmaceutically acceptable salt thereof. In embodiments, the cell is a cancer cell. In embodiments, cell death is through apoptosis. In embodiments, the cell is a metastatic cancer cell.

In embodiments, the patient has cancer cells expressing a gene involved in the folate pathway (e.g. dihydrofolate reductase (DHFR), thymidylate synthase (TYMS) or folylpolyglutamate synthase (FPGS)). In embodiments, the patient has cancer cells which express dihydrofolate reductase (DHFR). In embodiments, the patient has cancer cells which express thymidylate synthase (TYMS). In embodiments, the patient has cancer cells which express folylpolyglutamate synthase (FPGS). In embodiments, the cancer cells express DHFR at greater levels than a control (e.g., non-cancer cells). In embodiments, the cancer cells express TYMS at greater levels than a control (e.g., non-cancer cells). In embodiments, the cancer cells express FPGS at greater levels than a control (e.g., non-cancer cells).

V. Embodiments
Embodiment P1
A compound, or a pharmaceutically acceptable salt thereof, having the formula:
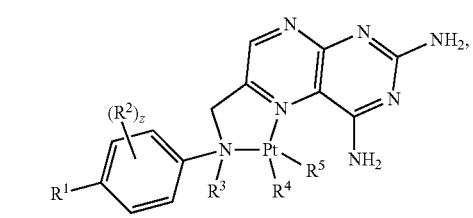
(I)
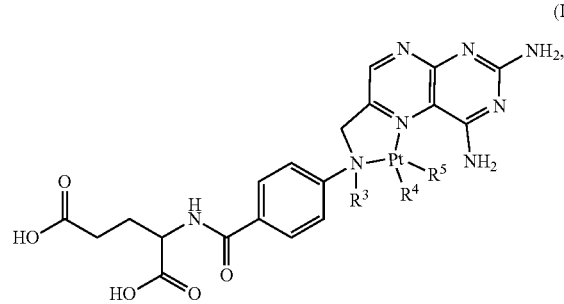
(II)
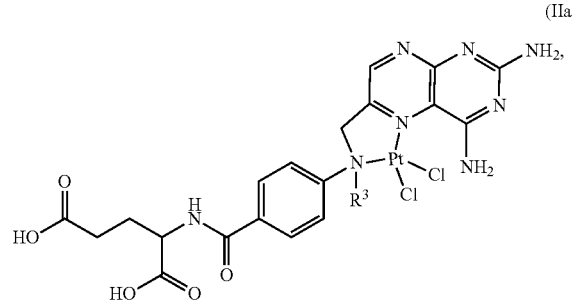
(IIa)
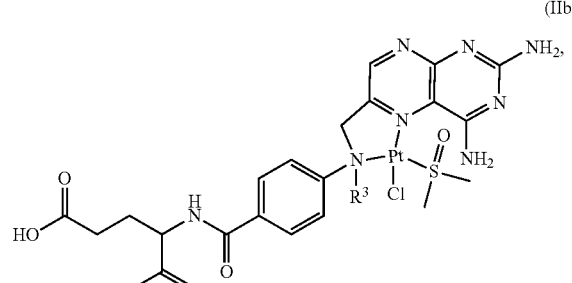
(IIb)
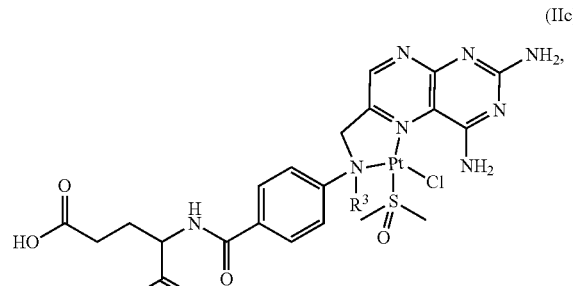
(IIc)
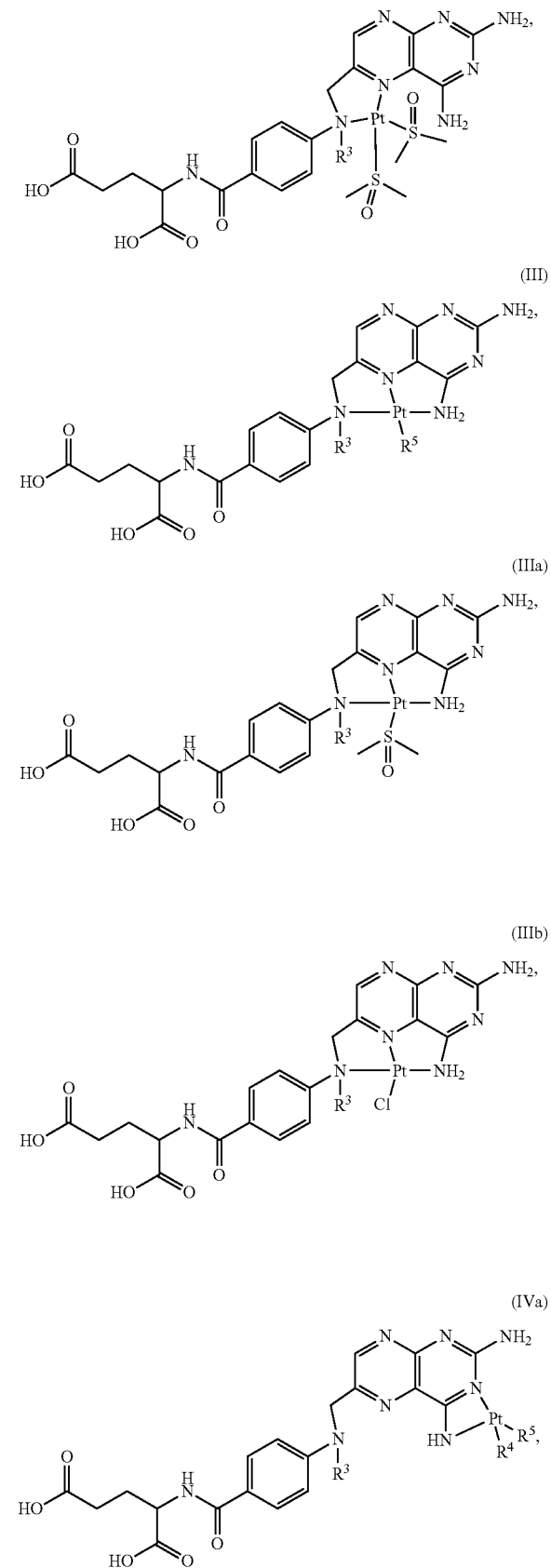

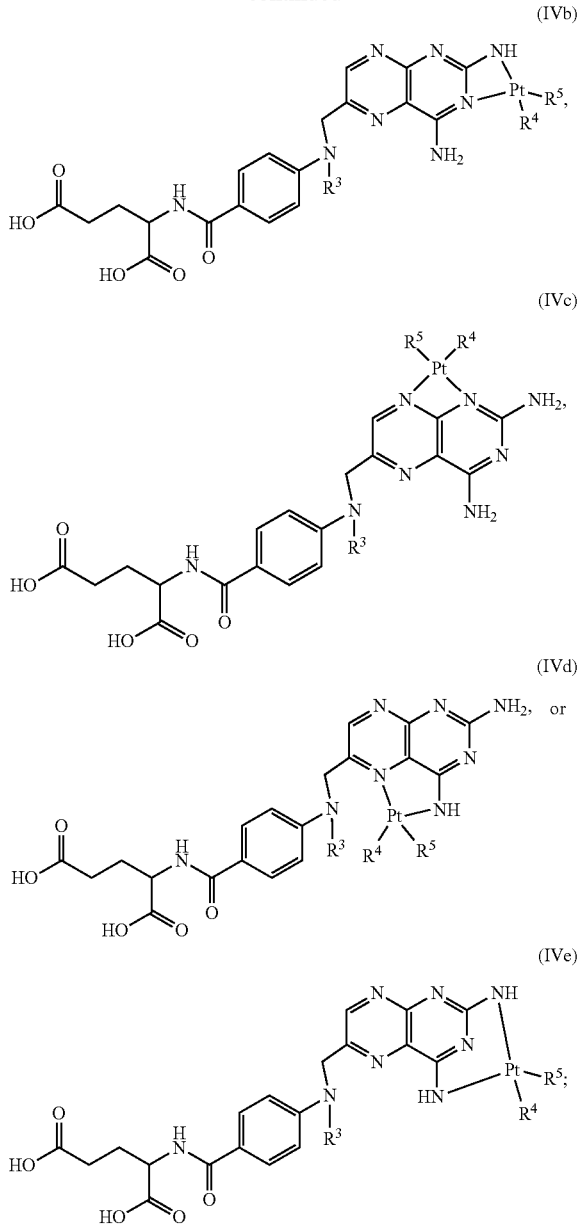

wherein R¹ is independently halogen, —SR⁹, —OSO₂R⁸, —OSO₃H, —NH₂NH₂, —ONR⁶R⁷, —NH₂C═(O)NHNH₂, —NH₂C═(O)NR⁶R⁷, —NHR⁶R⁷, —OC(O)R⁸, —OC(O)NR⁶R⁷, —OR⁹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² is independently halogen, —CY²₃, —CN, —SO_qR¹⁰, —SO_uNR¹¹R¹², —NHNH₂, —ONR¹¹R¹², —NHC═(O)NHNH₂, —NHC═(O)NR¹¹R¹², —N(O)_m, —NR¹¹R¹², —C(O)R¹³, —C(O)OR¹³, —C(O)NR¹¹R¹², —OR¹⁰, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R² substituents may optionally be joined to form a substituted or unsubstituted cycloalkyl, substituted or unsubstituted heterocycloalkyl, substituted or unsubstituted aryl, or substituted or unsubstituted heteroaryl; R³ is an unsubstituted C₁-C₄ alkyl or H; R⁴ and R⁵ are independently halogen, dimethyl sulfoxide, N₃, SCN, or CN; R⁶, R⁷, R⁸, R⁹, R¹⁰, R¹¹, R¹², and R¹³ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z is an integer from 0 to 4; u is independently an integer from 1 to 2; m is independently an integer from 1 to 2; q is independently an integer from 0 to 4; Y² is independently —Cl, —Br, —I, or —F.

Embodiment P2

The compound of embodiment P1, wherein R¹ is substituted or unsubstituted heteroalkyl.

Embodiment P3

The compound of embodiment P1, wherein R¹ is substituted or unsubstituted 2 to 10 membered heteroalkyl.

Embodiment P4

The compound of embodiment P1, wherein R¹ is substituted or unsubstituted 4 to 8 membered heteroalkyl.

Embodiment P5

The compound of any one of the embodiments P1 to P4, wherein R¹ is substituted with oxo, —OH, —NH₂, —SH, —COOH, —CN, —CF₃, —NO₂, halogen, unsubstituted alkyl, unsubstituted heteroalkyl, unsubstituted cycloalkyl, unsubstituted heterocycloalkyl, unsubstituted aryl, or unsubstituted heteroaryl.

Embodiment P6

The compound of any of embodiments P1 to P5 wherein R⁴ and R⁵ are independently halogen or dimethyl sulfoxide.

Embodiment P7

The compound of any of embodiments P1 to P5 wherein R⁴ and R⁵ are independently —Cl.

Embodiment P8

The compound of any of embodiments P1 to P5 wherein R⁴ and R⁵ are independently dimethyl sulfoxide.

Embodiment P9

The compound of any one of embodiments P1 to P8, wherein z is 0.

Embodiment P10

A pharmaceutical composition comprising a pharmaceutically acceptable excipient and a compound of any one of embodiments P1 to P9 or a pharmaceutically acceptable salt thereof.

Embodiment P11

A method of treating cancer in a patient in need of such treatment, said method comprising administering a therapeutically effective amount of a compound of any one of embodiments P1 to P9 or a pharmaceutically acceptable salt thereof.

Embodiment P12

The method of embodiment P11, wherein said cancer is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer.

Embodiment P13

The method of any one of the embodiments P11 to P12, wherein the patient has cancer cells expressing a folate transporter protein a folate transporter or an organic anion transporter.

Embodiment P14

The method of any one of embodiments P11 to P13 further comprising a method of measuring the level of a folate transporter in a sample from the patient.

Embodiment P15

The method of embodiment P14, wherein said sample comprises cancer cells.

Embodiment P16

The method of any one of embodiments P11 to P15, wherein the compound or a pharmaceutically acceptable salt thereof binds to DNA.

Embodiment P17

The method of any one of embodiments P11 to P16, wherein the patient has cancer cells expressing a gene (e.g. dihydrofolate reductase (DHFR), thymidylate synthase (TYMS) or folylpolyglutamate synthase (FPGS)) involved in the folate pathway.

VI. ADDITIONAL EMBODIMENTS

Embodiment 1

A compound, or a pharmaceutically acceptable salt thereof, having the formula:

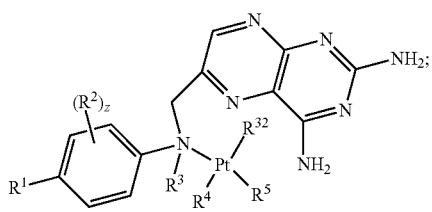

wherein $R^1$ is independently halogen, $-CY^1_3$, $-CN$, $-SR^9$, $-OSO_2R^8$, $-OSO_3H$, $-NH_2NH_2$, $-ONR^6R^7$, $-NH_2C(O)NHNH_2$, $-C(O)R^8$, $-C(O)NR^6R^7$, $-NH_2C(O)NR^6R^7$, $-NR^6R^7$, $-OC(O)R^8$, $-OC(O)NR^6R^7$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently halogen, $-CY^2_3$, $-CN$, $-SO_qR^{10}$, $-SO-NR^{11}R^{12}$, $-NHNH_2$, $-ONR^{11}R^{12}$, $-NHC=(O)NHNH_2$, $-NHC=(O)NR^{11}R^{12}$, $-N(O)_m$, $-NR^{11}R^{12}$, $-C(O)R^{13}$, $-C(O)-OR^{13}$, $-C(O)NR^{11}R^{12}$, $-OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ is an unsubstituted $C_1$-$C_4$ alkyl or H;

$R^4$, $R^5$ and $R^{32}$ are independently halogen,

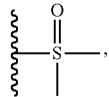

$-N_3$, $-SCN$, or $-CN$;

$R^6$, $R^7$, $R^8$, $R^9$, $R^{10}$, $R^{11}$, $R^{12}$, and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z is an integer from 0 to 4;

u is independently an integer from 1 to 2;

m is independently an integer from 1 to 2;

q is independently an integer from 0 to 4;

$Y^1$ and $Y^2$ are independently $-Cl$, $-Br$, $-I$, or $-F$.

Embodiment 2

The compound of claim 1, wherein $R^1$ is substituted or unsubstituted heteroalkyl.

Embodiment 3

The compound of claim 1, wherein $R^1$ is substituted or unsubstituted 2 to 10 membered heteroalkyl.

Embodiment 4

The compound of claim 1, wherein $R^1$ is substituted or unsubstituted 4 to 8 membered heteroalkyl.

Embodiment 5

The compound of any one of the claims 1 to 4, wherein $R^1$ is substituted with oxo, $-OH$, $-NH_2$, $-SH$, $-COOH$, $-CN$, $-CF_3$, $-NO_2$, halogen, unsubstituted alkyl, unsub-

Embodiment 6

The compound of claim 1, having the formula:

[Chemical structure showing a compound with glutamic acid moiety connected via amide to a benzene ring with (R²)z substituents, linked to a pteridine-2,4-diamine group through a CH₂-N(R³)-Pt(R⁴)(R⁵)(R³²)-NH₂ center]

Embodiment 7

The compound of any one of claims 1 to 6, wherein R³ is —CH₃ or H.

Embodiment 8

The compound of any of claims 1 to 7, wherein R⁴, R⁵ and R³² are independently halogen or

[Structure: -S(=O)(CH₃)- group]

Embodiment 9

The compound of any of claims 1 to 7, wherein R⁴, R⁵, and R³² are independently Cl.

Embodiment 10

The compound of any of claims 1 to 7, wherein R⁴, R⁵, and R³² are independently

[Structure: -S(=O)(CH₃)- group]

Embodiment 11

The compound of any of claims 1 to 7, wherein R⁴ and R⁵ are halogen and R³² is

[Structure: -S(=O)(CH₃)- group]

Embodiment 12

The compound of any one of claims 1 to 11, wherein z is 0.

Embodiment 13

The compound of claim 1, having the formula:

[Chemical structure showing compound with glutamic acid-amide-benzene-N(R³)-Pt(Cl)(Cl)(DMSO)-NH₂ linked to pteridine-2,4-diamine]

Embodiment 14

The compound of claim 1, having the formula:

[Chemical structure similar to Embodiment 13 with N-CH₃]

Embodiment 15

A pharmaceutical composition comprising a pharmaceutically acceptable excipient and a compound of any one of claims 1 to 14, or a pharmaceutically acceptable salt thereof.

Embodiment 16

A method of treating cancer in a patient in need of such treatment, said method comprising administering a therapeutically effective amount of a compound of any one of claims 1 to 14, or a pharmaceutically acceptable salt thereof.

Embodiment 17

The method of claim 16, wherein said cancer is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer.

Embodiment 18

The method of claim 16, wherein said cancer is osteosarcoma, neuroblastoma, or rhabdomyosarcoma.

Embodiment 19

The method of claim 16, wherein said cancer is breast cancer, central nervous system cancer, colon cancer, leukemia, melanoma, non-small cell lung cancer, ovarian cancer, prostate cancer, or renal cancer.

Embodiment 20

The method of claim 16, wherein said cancer is glioblastoma.

Embodiment 21

The method of any one of the claims 16 to 19, wherein the patient has cancer cells expressing a folate transporter protein a folate transporter or an organic anion transporter.

Embodiment 22

The method of any one of claims 16 to 21 further comprising a method of measuring the level of a folate transporter in a sample from the patient.

Embodiment 23

The method of claim 22, wherein said sample comprises cancer cells.

Embodiment 24

The method of any one of claims 16 to 23, wherein the compound or a pharmaceutically acceptable salt thereof binds to DNA.

Embodiment 25

The method of any one of claims 16 to 24, wherein the patient has cancer cells expressing a gene involved in the folate pathway.

EXAMPLES

In Vitro Growth Inhibition

Platinum-complexes are some of the most widely-used drugs for the treatment of cancers, especially solid tumors. Unfortunately, their tissue distribution is either nonspecific or of a specificity that is insufficient to cause adequate selective accumulation so as to deliver an adequate cytotoxic effect. The distribution of platinum complexes into various body tissues including tumors or neoplasms can be influenced through design of ligands that confer upon the platinum complex increased affinity for a particular influx transport mechanism. This enhanced affinity translates into higher sequestration of the platinum into tissues that express the particular influx transport mechanism. Higher tissue accumulation translates into (i) higher anticancer potency and (ii) lower potential of adverse effects because the platinum is channeled away from the tissue where adverse effects occur.

Synthesis of SM-69 and SM-70.

Platinum compounds were designed and synthesized to target selected influx transporters that have higher expression levels in tumors compared to normal tissues based on microarray expression data.

Figure 1B:
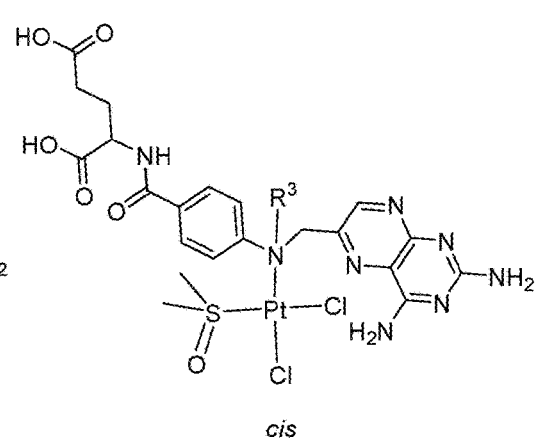

Solutions of methotrexate in a 4:1:1 mixture of water, ethanol and DMSO, respectively, were treated with one equivalent of potassium tetrachloroplatinate ($K_2PtCl_4$). The mixture was stirred at room temperature for up to 24 hours, after which time, the precipitate formed was filtered. The filter-cake was washed successively with methanol (10 mL/mmol, 4 times) and ice-cold water (10 mL/mmol, 4 times). The solids were dried overnight under 0.5 mmHg of pressure at room temperature to afford SM-69 (AT-69) (from methotrexate). $R^3=CH_3$ in FIG. 1A. The proposed chemical structure of SM-69 ($R^3=CH_3$), a platinum-methotrexate complex, [Pt(DMSO)methotrexate(Cl)], and is assumed to encompass all stereoisomers. This structure includes one DMSO ligand and one chloride ligand on the leaving group of the platinum complex. The methotrexate is the ligand of the non-leaving group. The synthesis of SM-70 (AT-70) is identical, however aminopterin was used instead of methotrexate thus, $R^3=H$ in FIGS. 1A-1B. The synthesis above without including DMSO to the solutions of methotrexate was also performed. As a result of this synthesis, the structure of the product does not have DMSO as ligand and instead will have two chloride ligands on the leaving group of the platinum complex. This product is called SM-69B (wherein $R^3$ of FIG. 1B is $CH_3$) or SM-70B (wherein $R^3$ of FIG. 1B is H).

Elemental analysis (CHN), proton NMR and mass spectrometer were performed to confirm the structures. The 1H-NMR data reveal SM69 to be comprised of a single, pure compound. The $^1$H-NMR conclusively establishes the presence of methotrexate as a ligand on the platinum. In particular, $^1H,^{195}Pt$ coupling is observed for the N—$CH_3$ and methylene protons. This coupling suggests the coordination sites shown in FIGS. 1A-1B. Large shifts in the aromatic $NH_2$ peaks also suggest that these hydrogen atoms are close in proximity to the platinum center. The compound SM-69 (AT-69) is shown in FIGS. 1A-1B. The $^{195}Pt$ NMR spectrum shows a peak at −2964 ppm. This peaks supports the conclusion that DMSO is bound to SM-69 based on reported studies with platinum compounds bound to DMSO (Transition Metal Chemistry, December 1992, Volume 17, Issue 6, pp 579-582; Inorganica Chimica Acta 319 (2001) 95-108). The ESI-MS (positive mode) displays a major peak at m/z 763.3. A trans isomer of SM-69 is a more favorable compound compared to cis isomer of SM-69. The reason is because the cis isomer is less stable by 16 kcal/mol. Furthermore, a cis isomer should display more NOE crosspeaks between DMSO and methotrexate, and this was not observed Based on the molecular weight and the structured isotope pattern of the spectrum, the molecular ion matches for the cationic species [Pt(methotrexate)(DMSO)Cl]$^+$ ($C_{22}H_{29}O_6N_8SClPt$). The ESI-MS (negative mode) displays a major peak at m/z 797.2, which suggests an additional Cl atom compared to the structure from ESI positive mode. Based on the molecular weight and the structured isotope pattern of the spectrum, the molecular ion matches to the anion species [Pt(methotrexate)(DMSO)Cl]$^-$ ($C_{22}H_{29}O_6N_8SClPt$). The IR spectrum shows a peak at 1128 cm$^{-1}$. This vibrational mode most likely arises from the S=O stretch on a platinum-coordinate DMSO ligand, as depicted in FIG. 1A. Free DMSO has a S=O stretching mode at 1055 cm$^{-1}$, which was not observed in the IR spectrum. The result from elemental analysis confirms that S and Pt atoms are present in SM69, approximately in a 1:1 atomic ratio. The $^1$H-NMR data reveal SM-69B to be comprised of a single, pure compound. The ESI-MS (positive mode) displays a major peak at m/z 721.69. Based on the molecular weight and the structured isotope pattern of the $^1$H NMR spectrum, the molecular ion matches for the cationic species [Pt(methotrexate)Cl$_2$]$^+$ (C$_{20}$H$_{22}$O$_5$N$_8$Cl$_2$Pt). Unlike SM-69, the IR spectrum did not show a peak at 1128 cm$^{-1}$. This is as expected since SM-69B does not have platinum coordinated DMSO ligand.

The Heteronuclear Multiple Bond Correlation (HMBC) 2-D NMR experiment gives correlations between carbons and protons that are separated by two, three or more bonds. The direct one-bond correlations are suppressed. The result from this spectrum shows that the platinum nucleus couples to CH$_3$ (a methyl group) therefore platinum must be bound to the nitrogen atom adjacent to the phenylene group. Evidence from a NOESY NMR experiment of SM-69 shows that H$_a$ and CH$_3$ correlate through space (<4 Å apart). Without being bound by any theory, the data indicates bidentate binding to platinum is unlikely for certain compounds disclosed herein. The trans isomer of SM-69 (FIG. 1A) is a more stable compound compared to cis isomer of SM-69 (FIG. 1B). The reason is because the cis isomer is less stable by 16 kcal/mol according to theoretical calculations. Furthermore, a cis isomer should display more NOE crosspeaks between DMSO and methotrexate, and this was not observed.

NCI-60 Human Tumor Cell Lines Screen.

SM69 was one of the compounds synthesized that was subsequently sent to the National Cancer Institute (NCI) Developmental Therapeutics Program (DTP) for screening against a panel of NCI-60 cell lines. The methods that were used by the DTP were described on the DTP website: (https://dtp.nci.nih.gov/discovery_development/nci-60/methodology.htm).

Cell Cultures.

Human cancer cell lines were purchased from UCSF Cell Culture Facility (CCF) or obtained through Material Transfer. Table 1 below shows a list of cell lines, their tumor types and their culture conditions. These cell lines were used to determine the cytotoxicity of SM-69 (and SM-70).

TABLE 1

Cell lines used for in vitro cytotoxicity studies.

| Cell Lines | Tumor type |
| --- | --- |
| SNF539 | Brain |
| SNB75 | Brain |
| U87MG | Brain |
| U251 | Brain |
| T98G | Brain |
| MG-63 | Osteosarcoma |
| SAOS-2 | Osteosarcoma |
| U-2 OS | Osteosarcoma |
| A204 | Rhabdomyosarcoma |
| A673 | Ewing's Sarcoma |
| RMS13 | Rhabdomyosarcoma |
| Kelly | Neuroblastoma |
| SHEP | Neuroblastoma |
| SH-SY5Y | Neuroblastoma |
| A549 | Non-small cell lung |
| H226 | Non-small cell squamous |
| DU145 | Prostate |
| PC3 | Prostate |
| HT29 | Colon |
| HCT116 | Colon |
| AsPC1 | Pancreas |
| A2780 | Ovary |
| A2780-CP | Ovary |
| PE01 | Ovary |
| PE04 | Ovary |
| OVCAR2 | Ovary |
| HEK293 | Kidney |

Determination of Platinum-DNA Adducts by ICP-MS.

Method to quantify platinum-DNA adducts by ICP-MS has been previously described (5,6). In brief, HEK293 cells were seeded in 6-well poly-D-lysine plate (cell density=0.5× 106 cells/well). The next day, the cells were washed twice with warmed Hanks Buffer (HBSS), and treated with 10 μM SM69, 10 cisplatin (positive control), saline and 10 μM methotrexate (negative control) for 2 hours at 37° C. After 2 hours, the cells were washed twice with cold HBBS. The platinum content associated with genomic DNA was determined as described elsewhere. Genomic DNA was isolated from the cell pellets using Genomic DNA purification kit (Promega) and the DNA-bound platinum was determined by ICP-MS, which was normalized to total DNA content (determined by absorption spectrometry at 260 nm).

Cytotoxicity Studies.

The cytotoxicity of SM-69 and SM-70 were measured by standard luminescent cell viability assay (CellTiter-Glo®) in 96-well plates using different cell lines as described in Table 1. After seeding the cells (~3000 cells/well) and incubating overnight, media only, cisplatin, SM-69 or SM-70 was added to the culture medium. The range of platinum concentrations used in the studies are 5 μM-100 μM. After 72 hours of treatment, the medium were removed and replaced with 50 μL of the media plus 50 μL of the CellTiterGlo reagent. The number of viable cells in culture will be determined based on quantitation of the ATP present, which is an indicator of the number of active cells. Concentration response graphs were generated for each compound using GraphPad Prism software. The graphs were analyzed using a curve fit for sigmoid dose-response, and IC$_{50}$ values were derived. The results were expressed as mean IC$_{50}$ values with the standard error of the mean.

In Vivo Pharmacokinetic and Maximum Tolerated Dose Toxicity of SM-69 and SM-70.

The pharmacokinetic and toxicity studies were performed using 2.5 mg/kg and 5 mg/kg of SM-69 and SM-70. Cisplatin at 2 mg/kg is equimolar with SM-69 (AT-69), and was used in the pharmacokinetic and toxicity studies. Table 2 described the pharmacokinetic study design for SM-69 (AT-69) and SM-70 (AT-70).

The maximum tolerated dose (MTD) studies of SM-69 and SM-70 were performed using the dosing regimen shown in Table 3. The mice used in MTD were given standard chow devoid of added folic acid (low folate diet) (See, Leamon C P et al., *J. Pharmacol. Exp. Ther.* 327: 918-925). Leamon et al. (2008) reported that the mice serum folate levels were much higher compared to human serum folate levels (>5-fold higher). Leamon et al showed that after 6 weeks of low folate diets, the serum and red blood cells folate concentrations reach steady-state, similar to human levels. SM-69 and SM-70 have folate-like structure attached to cisplatin, thus we designed the in vivo efficacy study using mice after 6 weeks treatment with low folate diet and continue on this diet throughout the treatment. Therefore we also designed a MTD study in mice treated with low folate diet. A total of thirty-six (36) CR nu/nu mice were used and assigned to the treatment groups shown in Table 3. Food consumption on the day before injection (Day −1) was recorded and then it was monitored every other day. Mice exhibiting severe signs of toxicity and/or were found in a moribund condition were euthanized prior to scheduled sacrifice. Blood for clinical chemistry was collected if possible. Liver, kidney and bone marrow were collected. One side of each tissue (except bone marrow) will be fixed in 4-10% formalin for future histology analysis, and the rest of tissue will be cut into pieces, snap frozen, and stored at −80° C. until analysis. Blood samples for clinical chemistry were centrifuged at 8000 rpm for 10 min at 4° C. within 1 hour of collection. Plasma was collected into 1.5 mL eppendorf tubes and stored at −80° C. until analysis. The measured parameters were alanine transaminase (ALT), aspartate transaminase (AST), alkaline phosphatase (ALP), total bilirubin, glucose, blood urea nitrogen (BUN), creatinine, and electrolytes. All experiments were housed in a virus-free, temperature controlled facility on a 12-h light-dark cycle.

TABLE 2

Pharmacokinetic study design in thirty (30) C57BL/6 mice approximately 7-8 weeks of age and weighted approximately 20 grams.

| Treatment Group No. | No. of Mice | Treatment | Blood Sampling Time |
|---|---|---|---|
| 1 | 3 | 2.5 mg/5 ml AT-69 | 15 min, 1 hr, 4 hr, 8 hr, and 24 hr |
| 2 | 3 | 2.5 mg/5 ml AT-69 | 30 min, 2 hr, 6 hr, and 12 hr |
| 3 | 3 | 5 mg/5 ml AT-69 | 15 min, 1 hr, 4 hr, 8 hr, and 24 hr |
| 4 | 3 | 5 mg/5 ml AT-69 | 30 min, 2 hr, 6 hr, and 12 hr |
| 5 | 3 | 2.5 mg/5 ml/kg AT-70 | 15 min, 1 hr, 4 hr, 8 hr, and 24 hr |
| 6 | 3 | 2.5 mg/5 ml/kg AT-70 | 30 min, 2 hr, 6 hr, and 12 hr |
| 7 | 3 | 5 mg/5 ml/kg AT-70 | 15 min, 1 hr, 4 hr, 8 hr, and 24 hr |
| 8 | 3 | 5 mg/5 ml/kg AT-70 | 30 min, 2 hr, 6 hr, and 12 hr |
| 9 | 3 | 2 mg/5 ml/kg Cisplatin | 15 min, 1 hr, 4 hr, 8 hr, and 24 hr |
| 10 | 3 | 2 mg/5 ml/kg Cisplatin | 30 min, 2 hr, 6 hr, and 12 hr |

Note:
Blood (>20 μl) was collected at 15 min, 30 min, 1 h, 2 h, 4 h, 6 h, 8 h, 12 h, and 24 h. Each group (3 mice/group) was assigned to 4-5 time points. The vehicle control for cisplatin will be saline. The vehicle control for AT-69 and AT-70 will be $KH_2PO_4$ (10 mM, pH = 7).

TABLE 3

Maximum Tolerated Dose studies for SM-69 (AT-69) and SM-70 (AT-70).

| Treatment Group No. | No. of Mice | Treatment | Dosing Day[note 1] |
|---|---|---|---|
| 1 | 4 | Saline | 0, 7, 14, 21, and 28 |
| 2 | 4 | 10 mM $KH_2PO_4$ (pH = 7) | 0, 7, 14, 21, and 28 |
| 3 | 4 | 2.5 mg/5 ml/kg AT-69 | 0, 7, 14, 21, and 28 |
| 4 | 4 | 5 mg/5 ml/kg AT-69 | 0, 7, 14, 21, and 28 |
| 5 | 4 | 7.5 mg/5 ml/kg AT-69 | 0, 7, 14, 21, and 28 |
| 6 | 4 | 2.5 mg/5 ml/kg AT-70 | 0, 7, 14, 21, and 28 |
| 7 | 4 | 5 mg/5 ml/kg AT-70 | 0, 7, 14, 21, and 28 |
| 8 | 4 | 7.5 mg/5 ml/kg SM-70 | 0, 7, 14, 21, and 28 |
| 9 | 4 | 5 mg/5 ml/kg Cisplatin | 0, 7, 14, 21, and 28 |

[note 1]Mice were housed 2 per cage, and subjected to various treatments above (i.v. dosing once a week, total 5 doses). The vehicle control for cisplatin will be saline. The vehicle control for AT-69 and AT-70 will be $KH_2PO_4$ (10 mM, pH = 7).

In Vivo Anti-Tumor Effect.

To assess the in vivo efficacy of SM-69 and SM-70, we performed the study in nude mice harboring xenografts of neuroblastoma and rhabdomyosarcoma (Table 4). The xenograft studies were performed by subcutaneous injection of SK-N-DZ (neuroblastoma, $30 \times 10^6$ cells/animal) and RMS13 (rhabdomyosarcoma, $20 \times 10^6$ cells/animal) in right flank of the male Charles River Laboratories nu/nu mice (7-8 weeks old, weight ~20 g). Once the tumor size reached 50-100 $mm^3$, mice were randomly assigned to various groups shown in Table 4. Mice were treated by intravenous tail vein injection once a week for 4 weeks. The tumor sizes and body weights were monitored twice a week. Tumor volumes were calculated according to the following formula: volume=height×weight×length×0.5236.

TABLE 4

Xenograft mouse model and dosing treatment for each groups.

| Treatment Group No. | No. of Mice | Xenografts | Treatment (i.v. injection) |
|---|---|---|---|
| 1 | 10 | SK-N-DZ | Vehicle |
| 2 | 10 | SK-N-DZ | 5 mg/kg cisplatin |
| 3 | 10 | SK-N-DZ | 5 mg/kg SM-69 |
| 4 | 10 | SK-N-DZ | 5 mg/kg SM-70 |
| 5 | 10 | RMS13 | Vehicle |
| 6 | 10 | RMS13 | 5 mg/kg cisplatin |
| 7 | 10 | RMS13 | 5 mg/kg SM-69 |
| 8 | 10 | RMS13 | 5 mg/kg SM-70 |

In Vitro Growth Inhibition Studies.

Figure 2A:
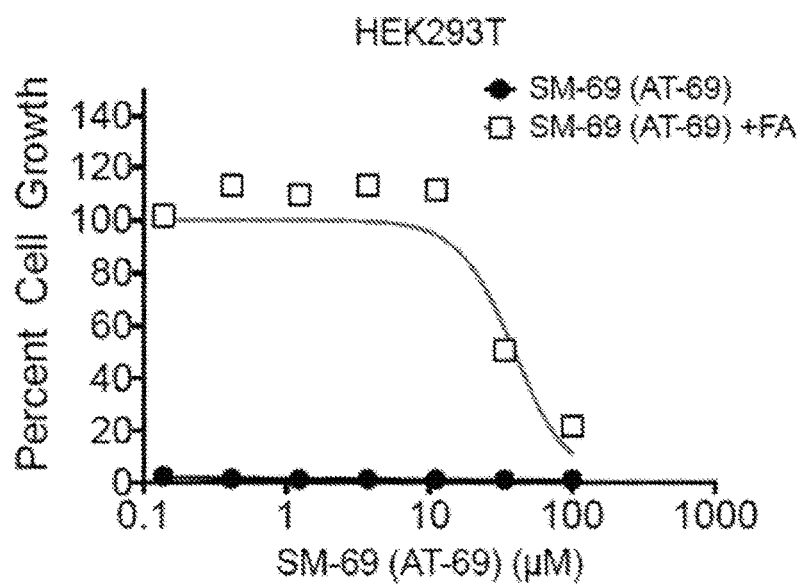
FIGS. 2A-2B.
Figure 2B:
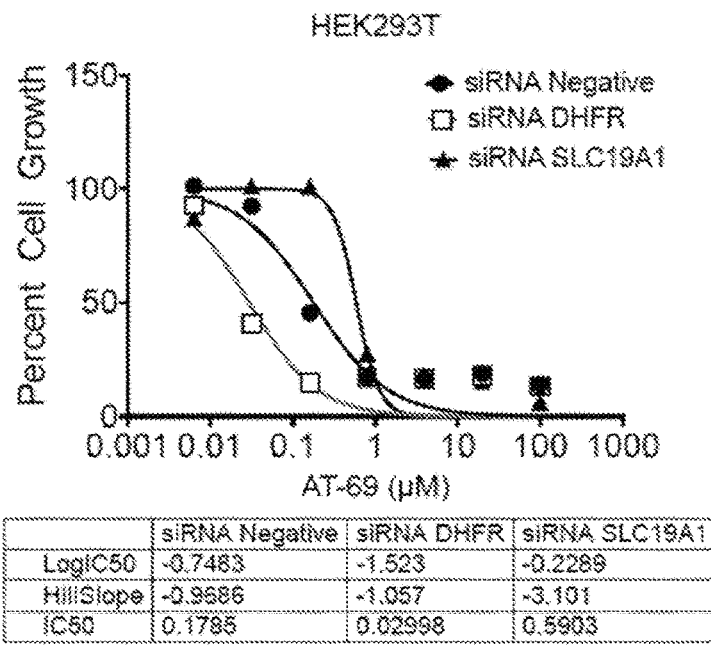

Various cell lines were incubated for 72 hours with SM-69 and SM-70. We also set up the experiment with cisplatin as our positive control. Table 5 shows the $IC_{50}$ of SM-69 (AT-69) against various cancer cell lines compared with cisplatin. SM-70 (AT-70) was also tested. To determine whether SM-69 interacts with genes in the folate pathway to exert its toxicity, we determined whether SM-69 cytotoxicity is attenuated in the presence of folinic acid as well as siRNA that knockdown SLC19A1 and DHFR (dihydrofolate reductase) (see FIGS. 2A-2B). Folinic acid significantly reduced cytotoxicity of SM-69 in HEK293-T (FIG. 2A) and other cell lines (T98G and U251). The potency of SM69, but not its total intracellular levels is dependent on folinic acid which suggests that this compound plays a role in the folic acid pathway and can be rescued by folinic acid when overdose. Reducing expression levels of SLC19A1 with siRNA, reduced cytotoxicity of SM-69 (AT-69) (FIG. 2B, triangle). Furthermore, reducing expression levels of DHFR (FIG. 2B, square) with siRNA enhanced cytotoxicity of SM-69. This result is similar to methotrexate, although the potency of SM-69 to inhibit DHFR is much weaker compared to methotrexate.

TABLE 5

The 50% growth inhibition ($IC_{50}$) of SM-69 and SM-70 in 27 cell lines from rare tumors and in some common cancer. The results showed that the cytotoxicity of SM-69 and SM-70 are comparable with cisplatin and some cell lines are more sensitive to SM-69 and SM-70 compared with cisplatin. SM-70 was tested in some cell lines.

| | | $IC_{50}$ (µM) | | |
|---|---|---|---|---|
| Cell Lines | Tumor | SM-69 (AT-69) | SM-70 (AT-70) | Cisplatin |
| SNF539 | Brain | 1.2 ± 1.1 | N.D. | 6.5 ± 7.2 |
| SNB75 | Brain | 6.1 ± 4.6 | N.D. | 15.4 ± 12.6 |
| U87MG | Brain | 2.2 ± 2.0 | N.D. | 16.2 ± 12.6 |
| U251 | Brain | 4.0 ± 4.5 | N.D. | 11.2 ± 10.8 |
| T98G | Brain | 40.8 ± 42.6 | N.D. | 27.5 |
| MG-63 | Osteosarcoma | 2.4 ± 1.4 | 1.4 ± 0.2 | 5.1 ± 2.3 |
| SAOS-2 | Osteosarcoma | 10.4 ± 9.4 | 12.0 ± 13.5 | 20.5 ± 9.9 |
| U-2 OS | Osteosarcoma | 18 ± 15 | 25.3 ± 19.9 | 59.3 ± 9.0 |
| A204 | Rhabdomyosarcoma | 3.9 ± 3.0 | 2.7 ± 2.1 | 4.6 ± 4.4 |
| A673 | Ewing's Sarcoma | 0.3 ± 0.3 | 0.2 ± 0.2 | 0.4 ± 0.3 |
| RMS13 | Rhabdomyosarcoma | 4.1 ± 2.3 | 4.6 ± 0.4 | 2.5 ± 0.5 |
| Kelly | Neuroblastoma | 3.7 ± 2.7 | 2.4 ± 1.9 | 7.0 ± 5.0 |
| SHEP | Neuroblastoma | 2.7 ± 2.3 | 1.5 ± 0.8 | 4.4 ± 2.4 |
| SH-SY5Y | Neuroblastoma | 0.6 ± 0.5 | 0.5 ± 0.4 | 1.0 ± 0.6 |
| A549 | Non-small cell lung | 1.2 ± 0.7 | N.D. | 1.8 ± 0.4 |
| H226 | Non-small cell squamous | 16.4 ± 13.1 | N.D. | 13.8 ± 2.8 |
| DU145 | Prostate | 1.5 ± 0.2 | N.D. | 0.5 ± 0.01 |
| PC3 | Prostate | 6.3 ± 1.5 | N.D. | 2.5 ± 0.3 |
| HT29 | Colon | 5.9 ± 1.6 | N.D. | 2.3 ± 0.4 |
| HCT116 | Colon | 4.8 ± 0.6 | N.D. | 2.1 ± 0.3 |
| AsPC1 | Pancreas | 7.0 ± 0.4 | N.D. | 2.9 ± 0.03 |
| A2780 | Ovary | 1.2 ± 0.2 | 4.2 ± 0.7 | 1.2 ± 0.2 |
| A2780-CP | Ovary | 8.6 ± 2.1 | 20.6 ± 3.6 | 8.6 ± 2.1 |
| PE01 | Ovary | 0.6 ± 0.4 | 2.9 ± 2.3 | 0.6 ± 0.4 |
| PE04 | Ovary | 4.9 ± 2.0 | 12.7 ± 2.7 | 4.9 ± 2.0 |
| OVCAR2 | Ovary | 3.3 ± 1.6 | 11.6 ± 4.3 | 3.3 ± 1.6 |

N.D. = Not determined.

Determination of Platinum-DNA Adducts by ICP-MS.

Figure 3A:
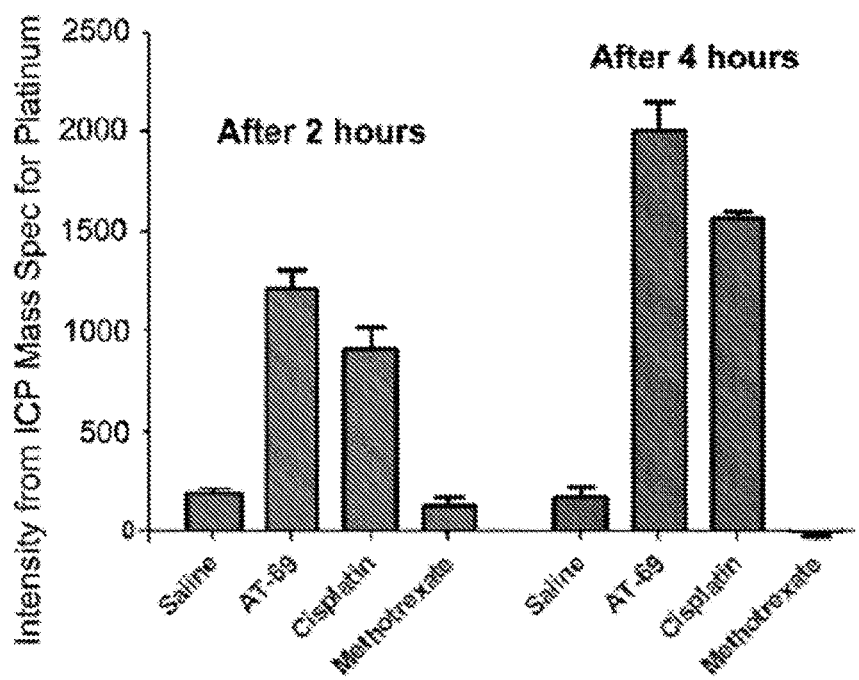
FIGS. 3A-3B.
Figure 3B:
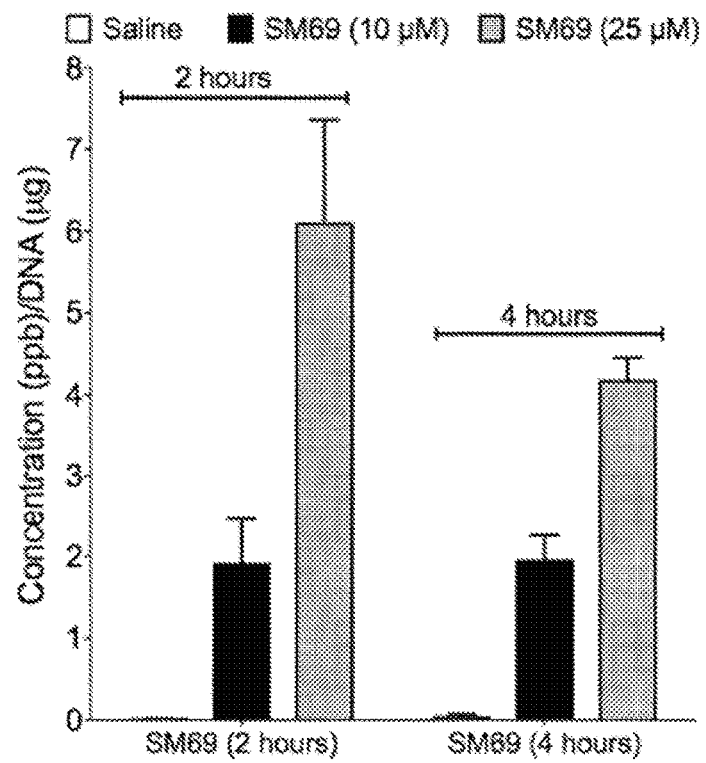

Platinum compounds, such as cisplatin and oxaliplatin, are known to covalently bound to DNA to form DNA-adduct and it is through this mechanism that the platinum compounds cause cytotoxicity by inhibiting DNA replication and cause cell death. We determined the platinum-DNA adduct content by ICP-MS to show that SM-69 could bind to DNA as effectively as cisplatin. FIG. 3A shows that SM-69 form platinum-DNA adducts similarly to cisplatin.

In Vivo Pharmacokinetic and Maximum Tolerated Dose Toxicity of SM-69 and SM-70.

Figure 4A:
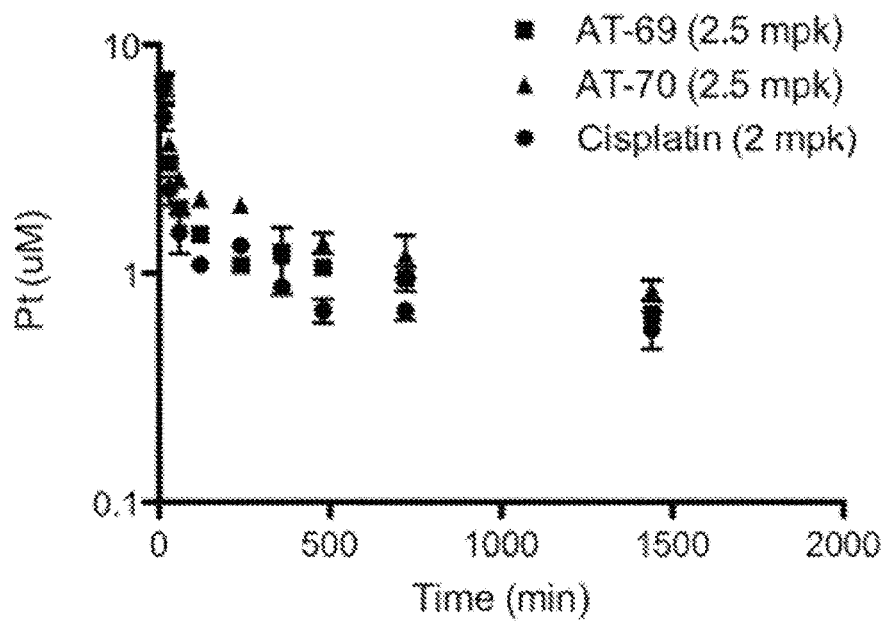
FIGS. 4A-4B. The total platinum levels in plasma after intravenous tail vein injection of SM-69 (AT-69), SM-70 (AT-70) and cisplatin. SM-69 5 mg/kg (5 mpk) and cisplatin 2 mg/kg (2 mpk) have equivalent dose of total platinum. At equimolar doses of SM-69 (5 mpk) and cisplatin (2 mpk), SM-69 has higher plasma levels of total platinum.
Figure 4B:
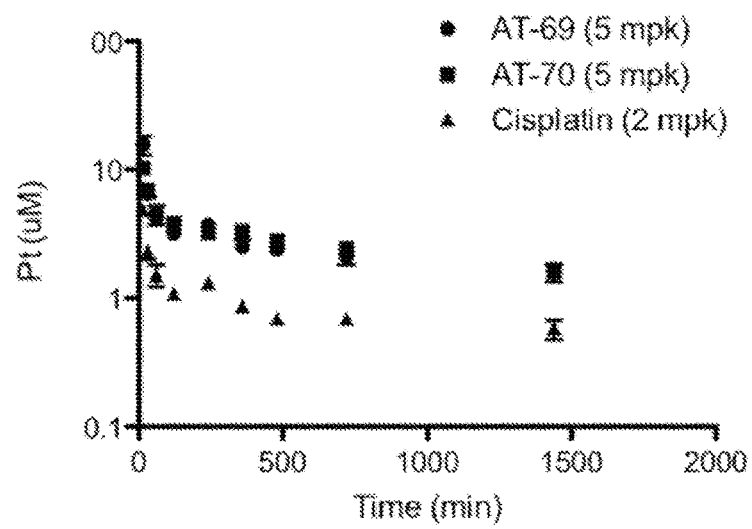
Figure 5A:
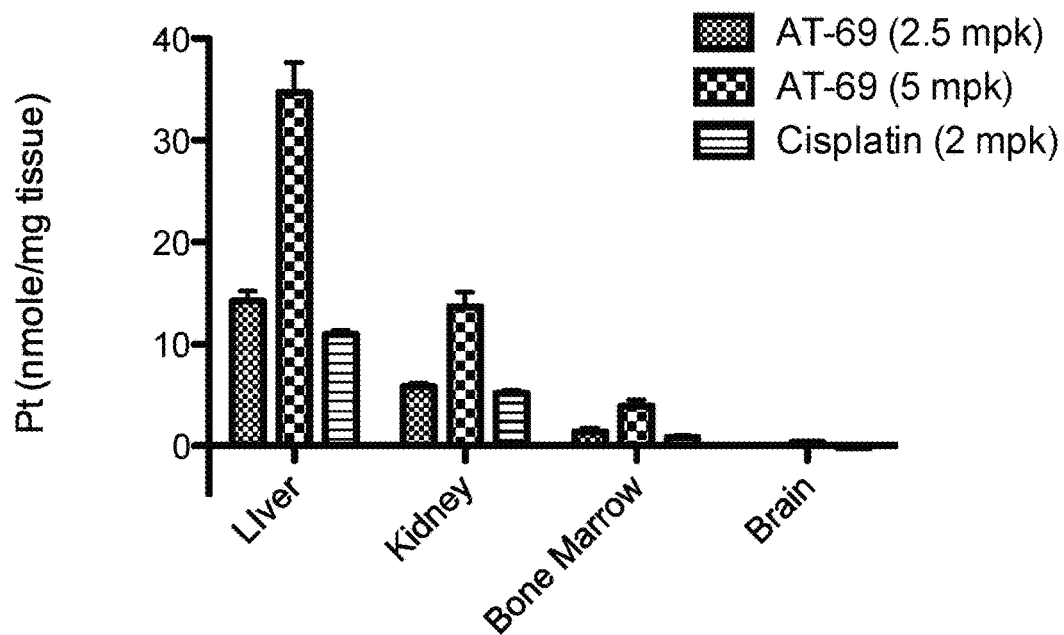
FIG. 5A-5D. Histograms of single dose tissue accumulation at 24-hrs.
Figure 5B:
Figure 5C:
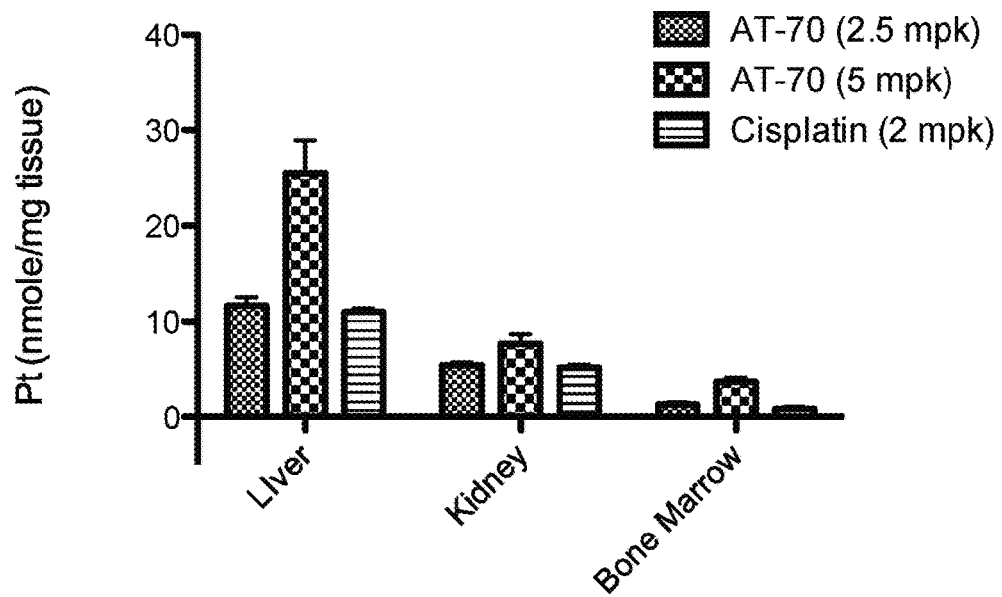
Figure 5D:
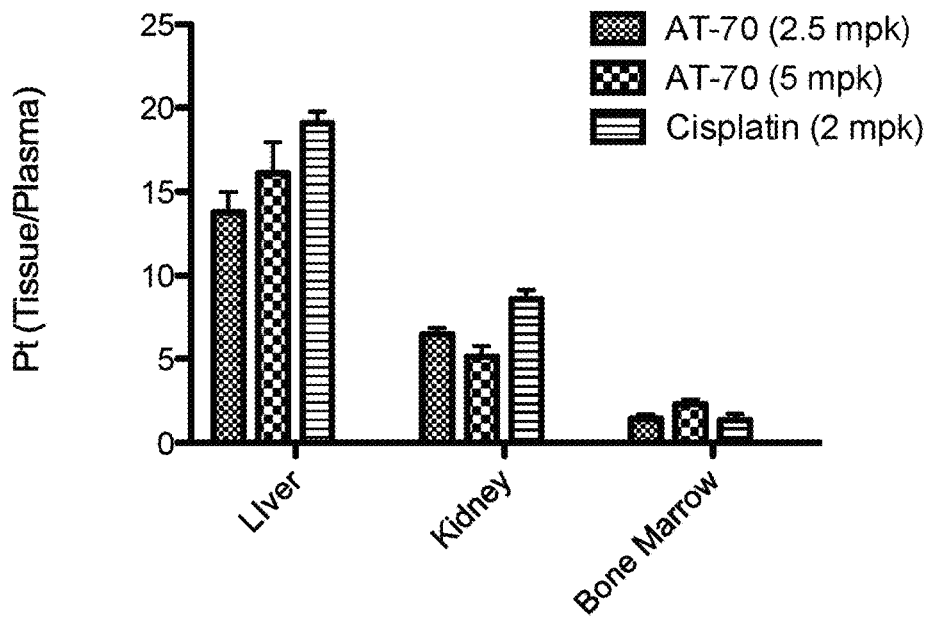
Figure 6:
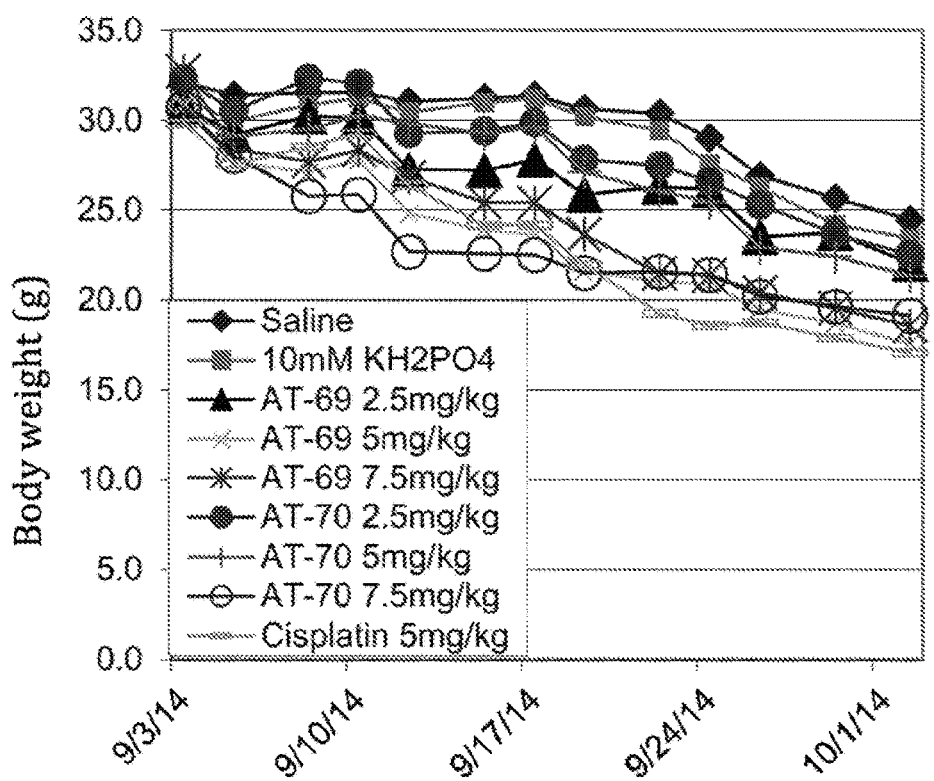
FIG. 6. Body weight change relative to day 0 after treatment with platinum compounds once a week for 4 weeks. There were significant body weight reductions (~30% reduction) after treatment with cisplatin (5 mpk), SM-69 (5 and 7.5 mpk) and AT-70 (7.5 mpk).
Figure 7A:
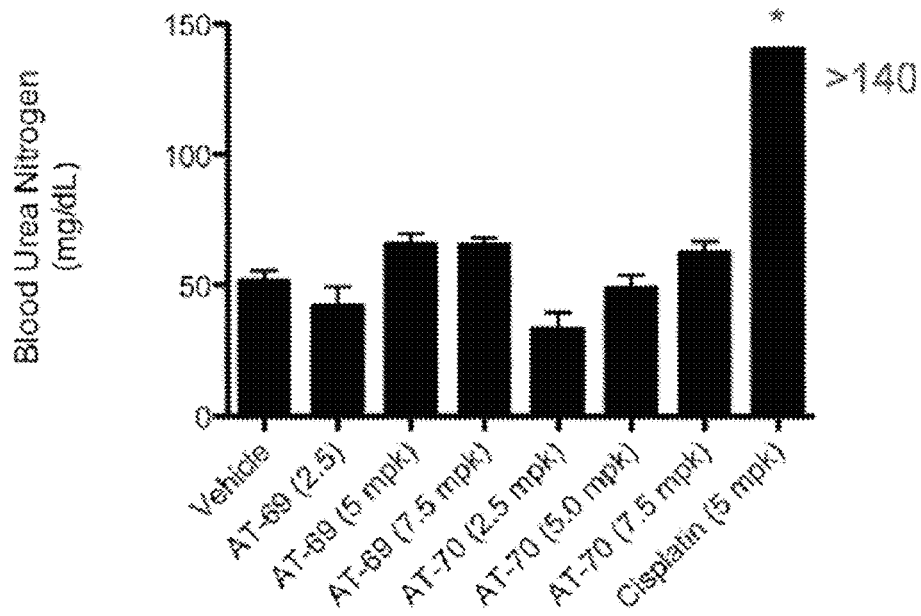
FIGS. 7A-7B.
Figure 7B:
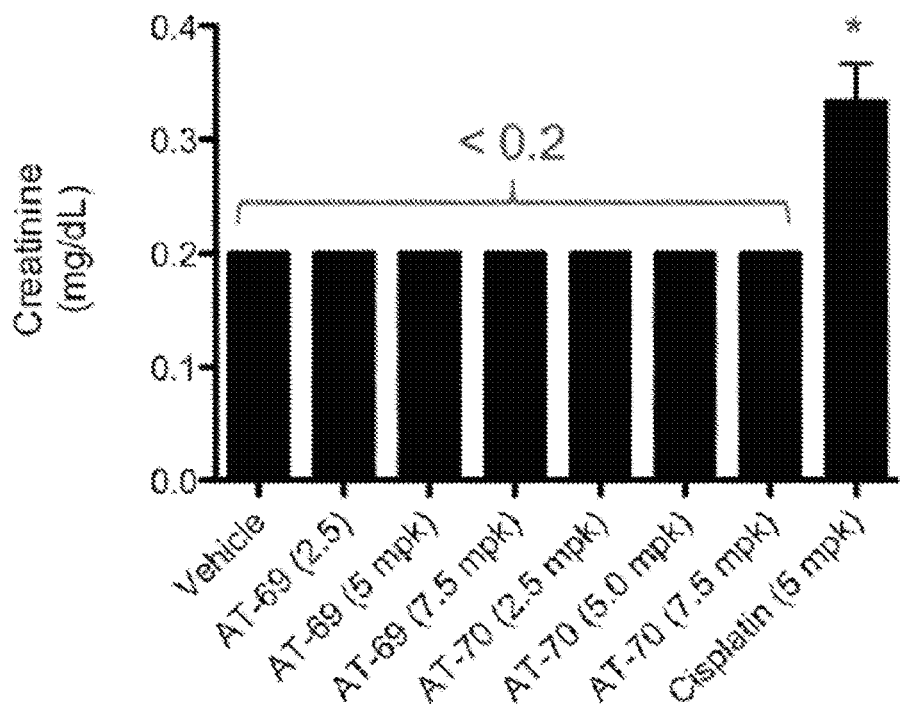

The time-course of total platinum (SM-69, SM-70 and cisplatin) in plasma following a single i.v. dose to mice is shown in FIGS. 4A-4B. The concentration versus time course of total platinum followed a two-compartment model in the mice. The mean plasma concentrations of SM-69 were significantly higher than cisplatin at equal molar dose of the two compounds (FIG. 4B). The total platinum levels in the tissues (liver, kidney and bone marrow) were similar between SM-69 and SM-70 after normalized to the plasma level at 24-hour time point. The cisplatin levels in the liver and kidney were slightly increased compared with equimolar dose of SM-69 (after normalized with plasma platinum levels) (FIG. 5). Based on the studies that administering 10 mg/kg of SM-69 (i.v. once a week) was lethal to C57BL/6 mice, but not 5 mg/kg dose, we selected the dose-range at 2.5, 5 and 7.5 mg/kg to determine the maximum dose of SM-69 without causing notable toxicity. In the maximum tolerated dose studies, we observed body weight reduction in all mice due to the low folate diet (FIG. 6). However, this body weight reduction was similar between saline treated, vehicle treated and low dose of SM-69 and SM-70 (2.5 mg/kg) (FIG. 6). Mice treated with SM-69 (5 mg/kg, 7.5 mg/kg) and SM-70 (7.5 mg/kg) has similar weight reduction profile compared with cisplatin (5 mg/kg) (approximately 30% weight reduction). We did not observe a significant difference in blood urea nitrogen (BUN) levels and serum creatine levels with SM-69 and SM-70 even at the highest dose, 7.5 mg/kg. However, cisplatin at 5 mg/kg showed significantly higher BUN and serum creatinine levels that suggests renal toxicity (FIGS. 7A-7B). The clinical chemistry test values in Table 6 and 7 were within normal range except in those mice treated with high dose of SM-69 (7.5 mpk), SM-70 (7.5 mpk) and cisplatin (5 mpk). In addition, the hematological toxicity of the compounds were not pronounced, except some values in the mice treated with 5 mpk cisplatin. Overall, the results show that the maximum tolerated dose for SM-69 and SM-70 is approximately 5 mg/kg in the animal studies.

TABLE 6

Clinical chemistry evaluation in mice after treatment with different doses of platinum or vehicle. The values shown were average levels in four mice except with SM-69 (AT-69) (7.5 mpk), SM-70 (AT-70) (7.5 mpk) and cisplatin (5 mpk), where one mouse was moribund in each group. The measured parameters were red blood cell count (RBC), mean corpuscular volume (MCV), hematocrit (HCT), mean corpuscular hemoglobin (MCH), mean corpuscular hemoglobin concentration (MCHC), red cell distribution width (RDW %), (RDWa), platelet count (PLT), mean platelet volume (MPV), hemoglobin (HGB), white blood cell count (WBC), lymphocytes (LYM and LYM %), monocytes (MONO and MONO %), granulocytes (GRAN and GRAN %).

|   | $KH_2PO_4$ | Saline | AT-69 (2.5 mpk) | AT-69 (5 mpk) | AT-69 (7.5 mpk) | AT-70 (2.5 mpk) | AT-70 (5.0 mpk) | AT-70 (7.5 mpk) | Cisplatin (5 mpk) |
|---|---|---|---|---|---|---|---|---|---|
| RBC | 11.21 | 10.62 | 10.34 | 10.86 | 10.38 | 10.82 | 10.95 | 9.96 | 9.66 |
| MCV | 44.30 | 44.38 | 44.68 | 43.95 | 43.80 | 44.40 | 43.68 | 43.43 | 44.03 |
| HCT | 49.65 | 47.13 | 46.20 | 47.65 | 45.47 | 48.08 | 47.85 | 43.20 | 42.63* |
| MCH | 15.48 | 15.68 | 15.65 | 15.73 | 15.63 | 15.68 | 15.48 | 15.47 | 15.80 |
| MCHC | 35.00 | 35.35 | 35.08 | 35.83 | 35.73 | 35.28 | 35.48 | 35.67 | 35.90 |
| RDW % | 21.58 | 21.23 | 21.53 | 21.93 | 21.87 | 21.40 | 21.95 | 21.63 | 21.63 |
| RDWa | 30.20 | 29.83 | 30.35 | 30.10 | 29.67 | 30.08 | 29.93 | 29.20 | 29.57 |
| PLT | 187.25 | 194.50 | 193.00 | 182.25 | 171.33 | 152.00 | 165.75 | 194.00 | 201.67 |
| MPV | 6.40 | 6.83 | 6.68 | 6.83 | 6.40 | 6.58 | 6.48 | 6.60 | 6.33 |
| HGB | 17.35 | 16.65 | 16.20 | 17.08 | 16.23 | 16.95 | 16.95 | 15.40 | 15.30 |
| WBC | 9.25 | 9.60 | 11.03 | 10.80 | 12.40 | 11.40 | 11.98 | 10.87 | 7.17 |
| LYM | 5.45 | 5.68 | 6.65 | 6.38 | 7.07 | 6.75 | 7.38 | 6.30 | 4.07 |
| MONO | 0.73 | 0.83 | 0.83 | 0.88 | 0.93 | 0.93 | 0.88 | 0.83 | 0.87 |
| GRAN | 3.08 | 3.10 | 3.55 | 3.55 | 4.40 | 3.73 | 3.73 | 3.73 | 2.23 |
| LYM % | 59.28 | 58.95 | 60.70 | 58.70 | 56.53 | 59.28 | 61.35 | 58.63 | 54.60 |
| MONO % | 7.30 | 8.08 | 7.43 | 8.03 | 7.43 | 7.83 | 7.30 | 7.50 | 11.07* |
| GRAN % | 33.43 | 32.98 | 31.88 | 33.28 | 36.03 | 32.90 | 31.35 | 33.87 | 34.33 |

*Significant change (P < 0.05) relative to Vehicle (Saline for CP; KH2PO4 for AT-69/70) Group

TABLE 7

Blood chemistry test. The values shown were the average levels in four mice except with SM-69 (AT-69) (7.5 mpk), SM-70 (AT-70) (7.5 mpk) and cisplatin (5 mpk), where one mouse was moribund in each group. The measured parameters were alanine transaminase (ALT), aspartate transaminase (AST), alkaline phosphatase (ALP), total bilirubin (TBIL), glucose, blood urea nitrogen (BUN), creatinine, and electrolytes.

|   | $KH_2PO_4$ | Saline | AT-69 (2.5 mpk) | AT-69 (5 mpk) | AT-69 (7.5 mpk) | AT-70 (2.5 mpk) | AT-70 (5 mpk) | AT-70 (7.5 mpk) | Cisplatin (5 mpk) |
|---|---|---|---|---|---|---|---|---|---|
| Glucose | 107.25 | 89.25 | 80.25 | 73.00 | 40.67* | 90.75 | 94.75 | 80.33 | 67.67 |
| BUN | 51.63 | 47.48 | 41.73 | 65.63 | 65.40 | 33.15 | 48.83 | 62.47 | >140* |
| CRE | <0.2 | <0.2 | <0.2 | <0.2 | <0.2 | <0.2 | <0.2 | <0.2 | 0.33* |
| ALT (GPT) | 51.25 | 50.50 | 52.75 | 83.75 | 258.33* | 96.75 | 76.00 | 62.00 | 41.67 |
| AST (GOT) | 326.25 | 204.75 | 252.25 | 447.25 | 573.67 | 273.50 | 264.75 | 479.67 | 515.00 |
| ALP | 85.25 | 90.75 | 99.00 | 117.25 | 140.33* | 92.25 | 110.50 | 146.50* | 152.67* |
| TBIL | 0.40 | 0.10 | 0.15 | 0.53 | 0.40 | 0.10 | 0.13 | 0.27 | 0.77* |
| Na | 155.00 | 156.00 | 163.25 | 157.50 | 162.33 | 156.75 | 155.75 | 158.33 | 130.67* |
| K | 5.18 | 4.35 | 4.93 | 4.95 | 5.13 | 6.18 | 5.85 | 6.57* | 5.67 |
| Cl | 122.00 | 125.25 | 129.50 | 122.50 | 124.33 | 125.25 | 122.00 | 128.33 | 102.33* |
| Na:K | 30.50 | 36.25 | 33.50 | 33.25 | 31.67 | 25.25 | 26.75 | 24.00 | 23.00 |

*Significant change (P < 0.05) relative to Vehicle (Saline for CP; KH2PO4 for AT-69/70) Group In Vivo Anti-Tumor Effect.

The in vivo efficacy of SM-69 and SM-70 were studied and compared to cisplatin. Treatment was performed according to the schedule presented in Table 4. The results were presented in FIGS. 8A-8B. Overall, the tumor volumes of the xenograft mice treated with SM-69 (5 mg/kg) were significantly lower compared with SM-70 (5 mg/kg).

TABLE 8

Transporter, substrate/inhibitor concentration, $IC_{50}$ (μM), and $IC_{50}$ (μM) with substrate or inhibitor for Compounds SM69 andf SM70.

| Compound | Transporter | Substrate/ Inhibitor (concentration) | $IC_{50}$ (μM) | $IC_{50}$ (μM) with substrate or inhibitor |
|---|---|---|---|---|
| SM69 | SLC19A1 | Folic acid (1 mM) | 13.50 ± 1.620 | 42.68 ± 4.105 |
| SM70 | SLC19A1 | Folic acid (1 mM) | 5.149 ± 0.8605 | 11.11 ± 0.4650 |

Efficacy of Platinum Compounds

TABLE 9

The $GI_{50}$ of SM-69 in NCI-60 cell lines. The results show that SM-69 is active in central nervous system, colon, leukemia, prostate and renal cancer cell lines.

| Panel | Cell Lines | SM-69 ($Log_{10}GI_{50}$, M) |
|---|---|---|
| Breast | BT-549 | −4.00 |
| | HS 578T | −4.00 |
| | MDA-MB-231/ATCC | −4.00 |
| | T-47D | −4.08 |
| | MDA-MB-468 | −5.08 |
| | MCF7 | −−5.39 |
| Central Nervous System | SNB-19 | −4.00 |
| | SNB-75 | −4.39 |
| | SF-268 | −5.04 |
| | SF-539 | −5.19 |
| | U251 | −5.43 |
| | SF-295 | −5.46 |
| Colon | COLO 205 | −4.34 |
| | HCC-2998 | −4.95 |
| | HCT-15 | −5.04 |
| | KM12 | −5.17 |
| | HT29 | −5.25 |
| | SW-620 | −5.48 |
| | HCT-116 | −5.50 |
| Leukemia | RPMI-8226 | −4.94 |
| | MOLT-4 | −5.30 |
| | CCRF-CEM | −5.39 |
| | HL-60(TB) | −5.46 |
| | SR | −5.52 |
| | K-562 | −5.79 |
| Melanoma | SK-MEL-2 | −4.00 |
| | SK-MEL-28 | −4.00 |
| | UACC-257 | −4.01 |
| | SK-MEL-5 | −4.12 |
| | MALME-3M | −4.71 |
| | UACC-62 | −4.90 |
| | MDA-MB-435 | −5.36 |
| | M14 | −5.41 |
| | LOX IMVI | −5.77 |
| Non-Small Cell Lung | HOP-92 | −4.00 |
| | EKVX | −4.16 |
| | HOP-62 | −4.26 |
| | NCI-H23 | −4.45 |
| | NCI-H226 | −4.61 |
| | NCI-H522 | −4.74 |
| | A549/ATCC | −5.30 |
| | NCI-H460 | −5.34 |
| Ovarian | OVCAR-4 | −4.00 |
| | SK-OV-3 | −4.00 |

TABLE 9-continued

The $GI_{50}$ of SM-69 in NCI-60 cell lines. The results show that SM-69 is active in central nervous system, colon, leukemia, prostate and renal cancer cell lines.

| Panel | Cell Lines | SM-69 ($Log_{10}GI_{50}$, M) |
|---|---|---|
| | IGROV1 | −4.11 |
| | OVCAR-3 | −4.15 |
| | OVCAR-5 | −4.61 |
| | NCI-ADR-RES | −5.20 |
| | OVCAR-8 | −5.36 |
| Prostate | DU-145 | −5.18 |
| | PC-3 | −5.35 |
| Renal | RXF 393 | −4.63 |
| | UO-31 | −4.92 |
| | ACHN | −5.12 |
| | CAKL-1 | −5.23 |
| | SN12C | −5.29 |
| | 786-0 | −5.46 |

Figure 9:
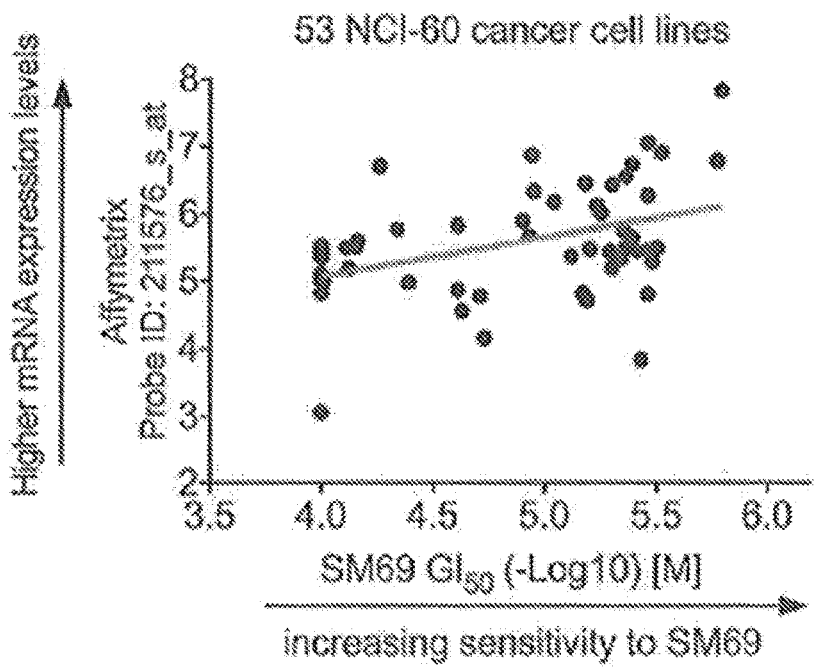
FIG. 9.
Figure 10:
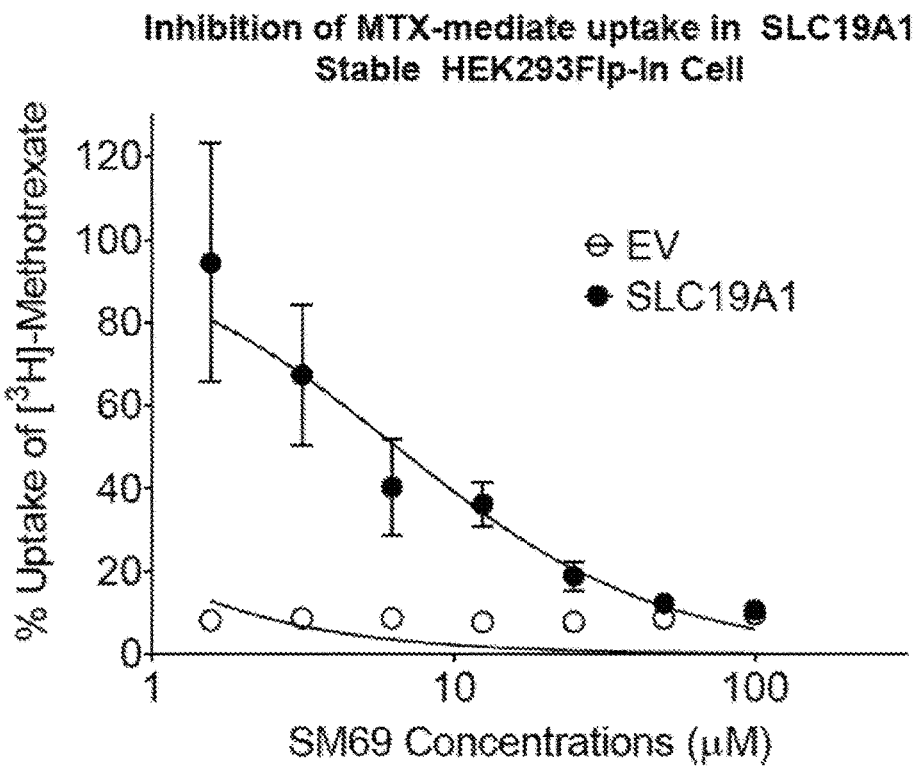
FIG. 10.
Figure 11A:
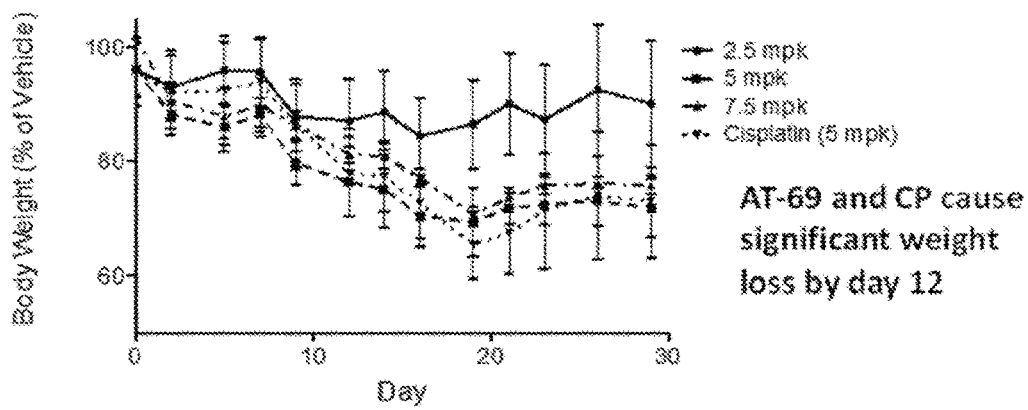
FIGS. 11A-11B. AT-69 and AT-70 induce significant body weight loss.
Figure 11B:
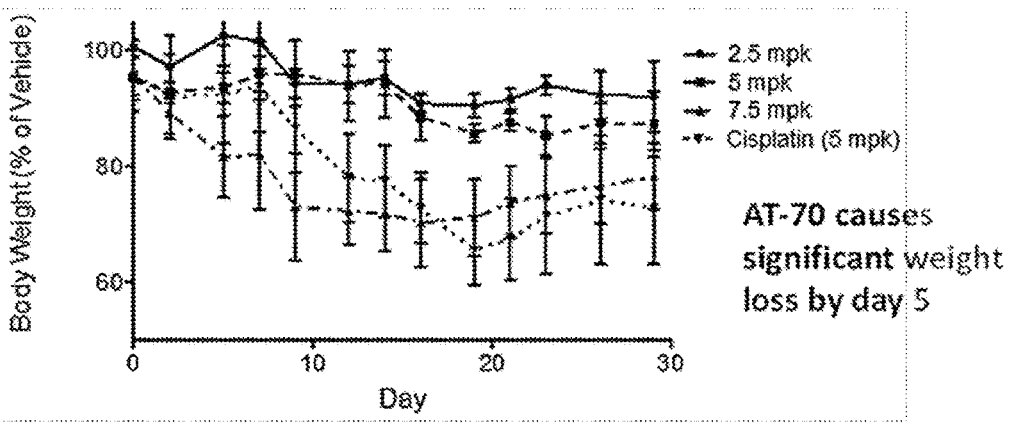
Figure 12A:
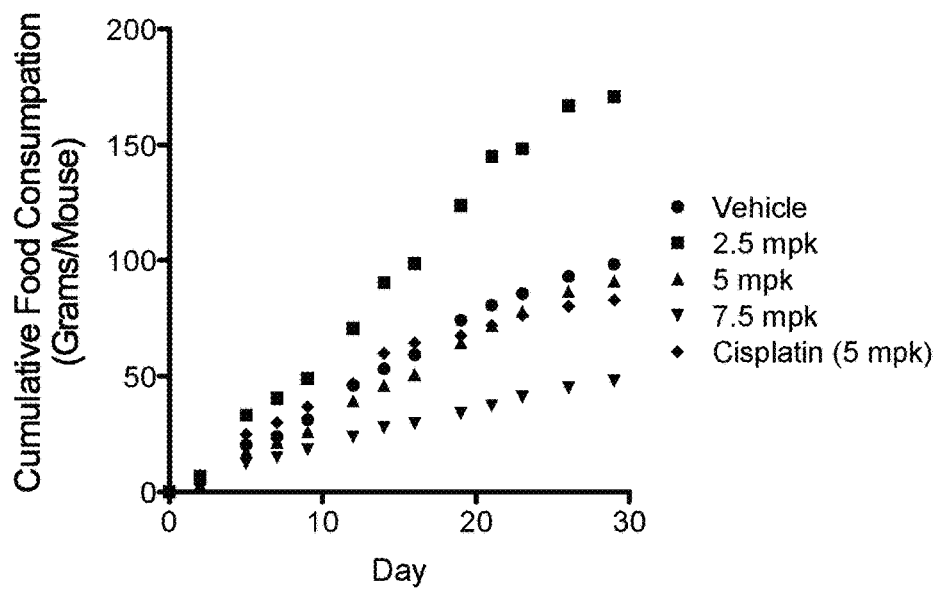
FIGS. 12A-12B. AT-69 and AT-70 dose-dependently alter food consumption. Food consumption was monitored over 30-days in a mouse model.
Figure 12B:
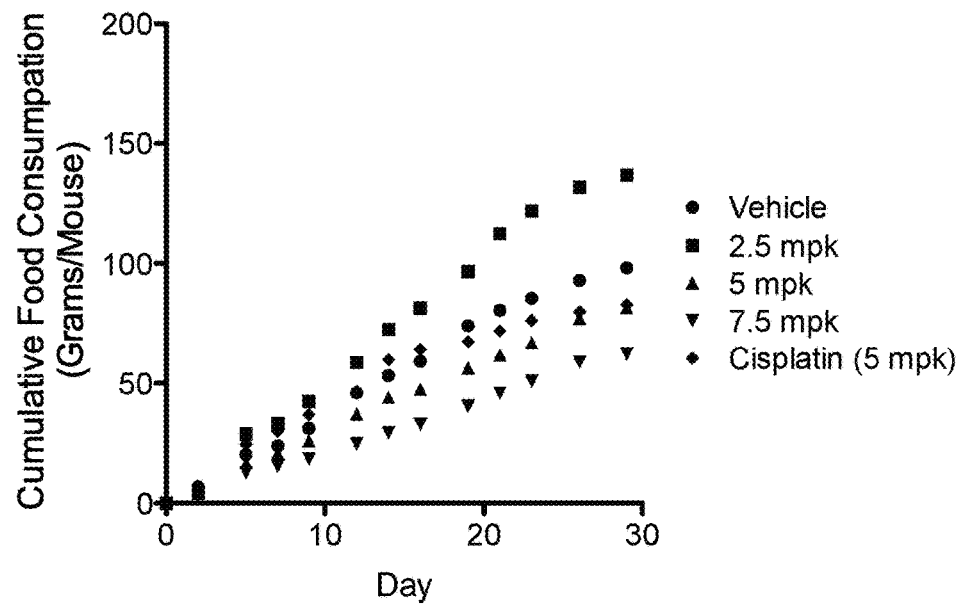

It is evident from Table 9 that SM-69 retains efficacy against NCI60 cell lines and its $GI_{50}$ is significantly correlated with SLC19A1 expression level (FIG. 9). The expression level of SLC19A1 is obtained from available microarray data, CELLMINER™ Build 1.0 (website at discover.nci.nih.govicellminer/). To validate that the influx transporter SLC19A1 was a determinant of SM-69 cytotoxicity, we demonstrated that the potency of SM-69 was significantly reduced in HEK-293T cells transfected with the siRNA for SLC19A1 ($IC_{50}$=0.2. μM compared to control cells, $IC_{50}$=0.6 μM) (FIG. 2B). In this study, we were able to achieve >90% knockdown of the SLC19A1 mRNA levels using the siRNA (Dharmacon ON_TARGETplus SMARTpool for human SLC19A1). Although SM-69 has a methotrexate molecule attached to it, SM-69 showed weaker inhibition of dihydrofolate reductase (DHFR) using the method described (website: www.sigmaaldrich.com, document cs0340bul.pdf) compared to methotrexate which exerts its pharmacological action primarily through DHFR inhibition. At 25 μM of SM-69, the DHFR activity was only reduced by 10-20%, whereas 10 μM of methotrexate, DHFR activity was reduced by >80%. This result suggests that SM-69 has a platinum-like mechanism of cytotoxicity (e.g. binding to DNA).

Efficacy in Xenograft Models of Osteosarcoma, Rhabdomyosarcoma and Neuroblastoma The effects of the disclosed compounds on tumor growth and survival in the mouse compared with saline treatment were investigated. As tabulated in Table 10 following, 50% growth inhibition ($GI_{50}$) was determined for AT-69 and AT-70 in nine cells lines from three different childhood tumors. Relative mRNA levels for SLC19A1 were also determined.

TABLE 10

GI$_{50}$ (µM) values for indicated cell lines and tumor types upon treatment with cisplatin, AT-69 and AT-70. SK-N-DZ was selected for Neuroblastoma xenograft; Cell lines selected based on literature evidence of ability to engraft in nude mice and sensitivity to platinum

| | | GI$_{50}$ (µM) | | | SLC19A1 |
|---|---|---|---|---|---|
| Cell Lines | Tumor | Cisplatin | AT-69 | AT-70 | mRNA levels |
| MG-63 | Osteosarcoma | 5.1 ± 2.3 | 2.4 ± 1.4 | 1.4 ± 0.2 | +++ |
| SAOS-2 | Osteosarcoma | 20.5 ± 9.9 | 10.4 ± 9.4 | 12.0 ± 13.5 | +++ |
| U-2 OS | Osteosarcoma | 59.3 ± 9.0 | 18 ± 15 | 25.3 ± 19.9 | ++ |
| A204 | Rhabdomyosarcoma | 4.6 ± 4.4 | 3.9 ± 3.0 | 2.7 ± 2.1 | ++ |
| A673 | Ewing's sarcoma | 0.4 ± 0.3 | 0.3 ± 0.3 | 0.2 ± 0.2 | ++++ |
| RMS13 | Rhabdomyosarcoma | 2.5 ± 0.5 | 4.1 ± 2.3 | 4.6 ± 0.4 | +++ |
| Kelly | Neuroblastoma | 7.0 ± 5.0 | 3.7 ± 2.7 | 2.4 ± 1.9 | +++ |
| SHEP | Neuroblastoma | 4.4 ± 2.4 | 2.7 ± 2.3 | 1.5 ± 0.8 | ++ |
| SH-SY5Y | Neuroblastoma | 1.0 ± 0.6 | 0.6 ± 0.5 | 0.5 ± 0.4 | ++ |

Figure 8A:
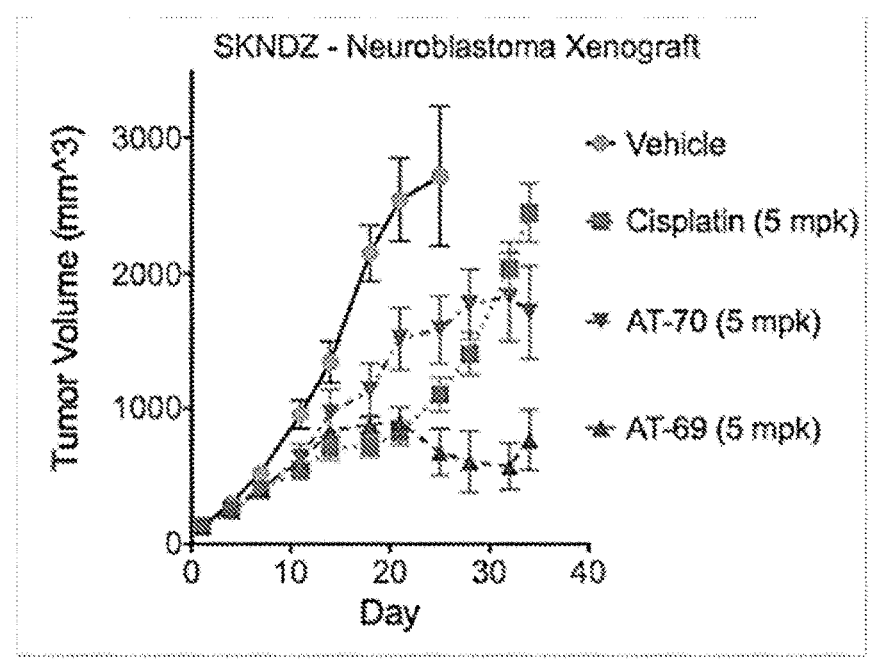
FIGS. 8A-8B. Tumor volume in mice with xenografts of (FIG. 8A) SKNDZ neuroblastoma and (FIG. 8B) RMS13 rhabdomyosarcoma treated with saline, cisplatin, SM-69 (AT-69) and SM-70 (AT-70) (N=10 per treatment group). Mice were dosed 5 mg/kg by tail-vein injection once a week for 4 weeks, starting from day 0. Tumor volume in mice treated with SM-69 was significantly different compared with other groups, approximately from day 20. Drugs were discontinued on Day 21 and mice were scarified on Day 28.
Figure 8B:
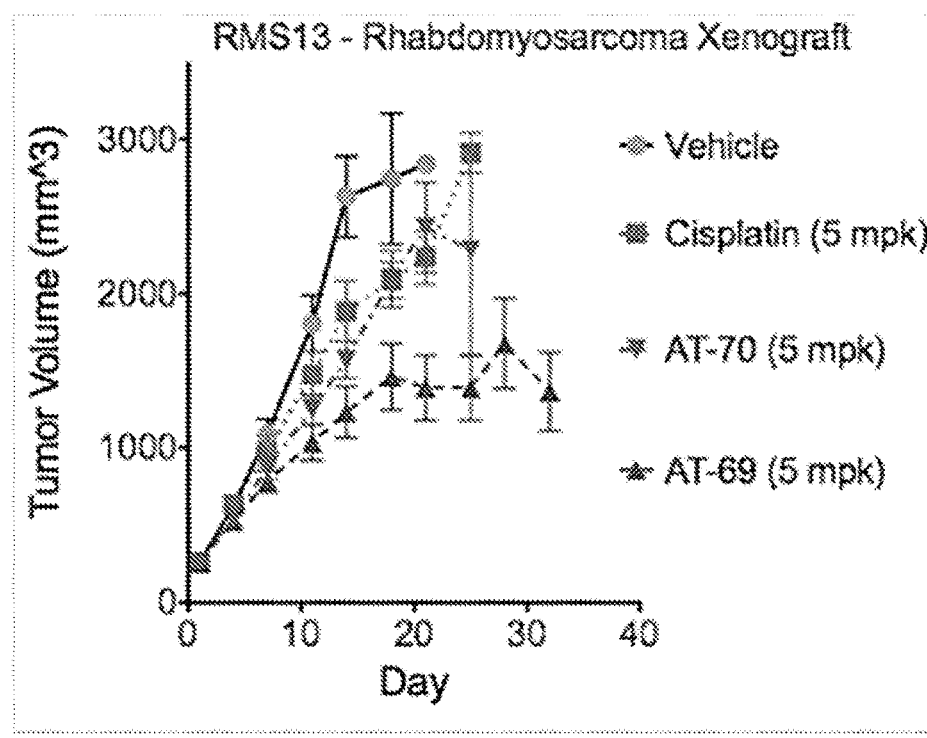
Figure 13:
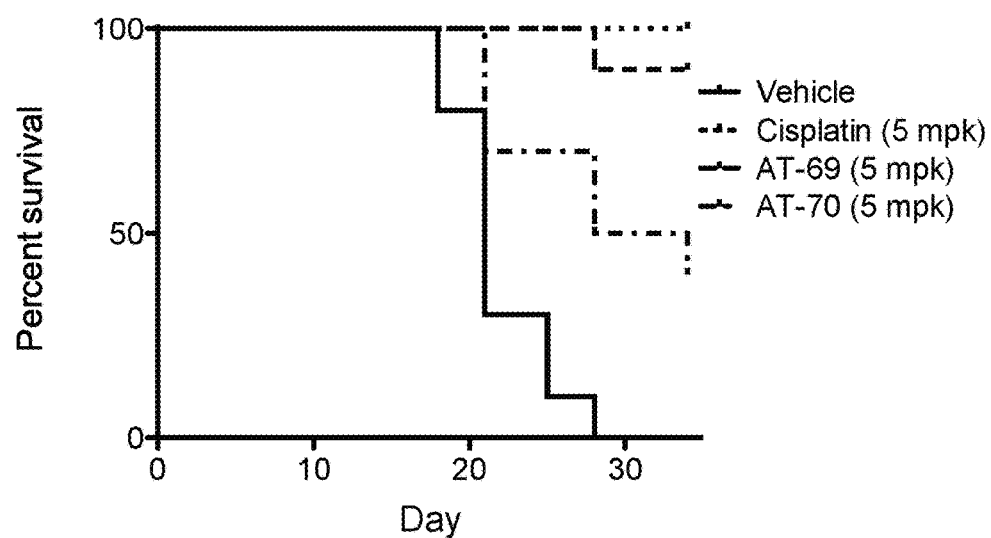
FIG. 13.
Figure 14:
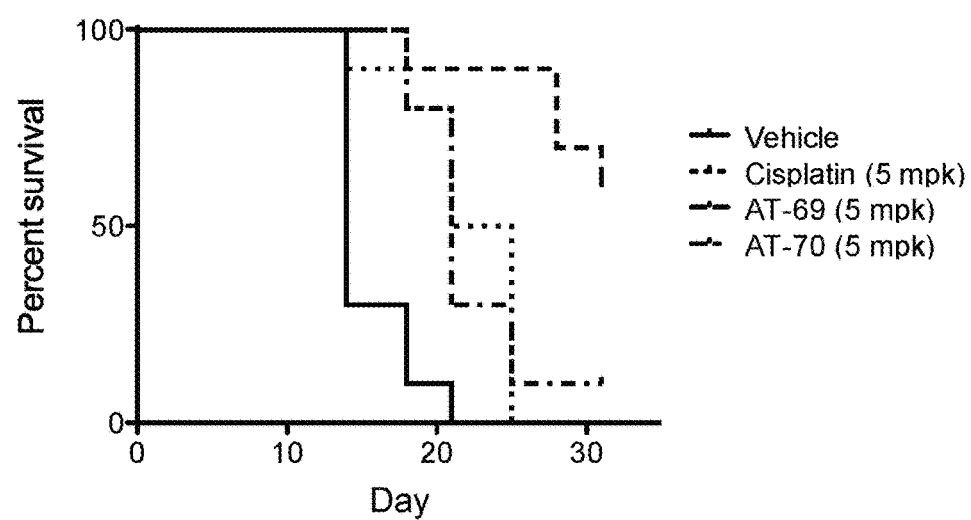
FIG. 14.
Figure 15A:
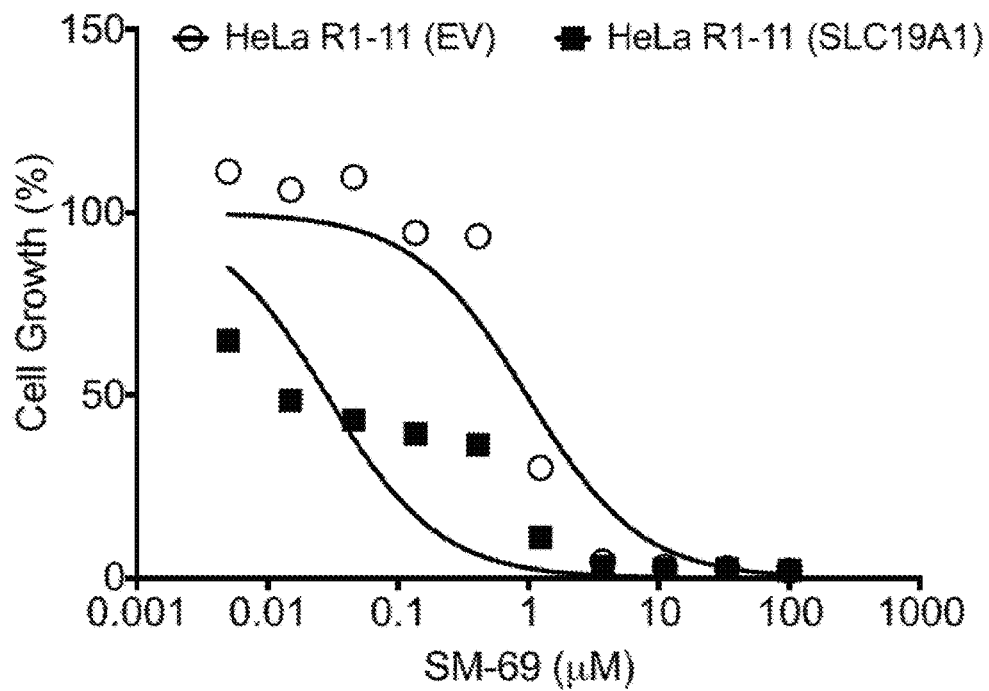
FIGS. 15A-15D.
Figure 15B:
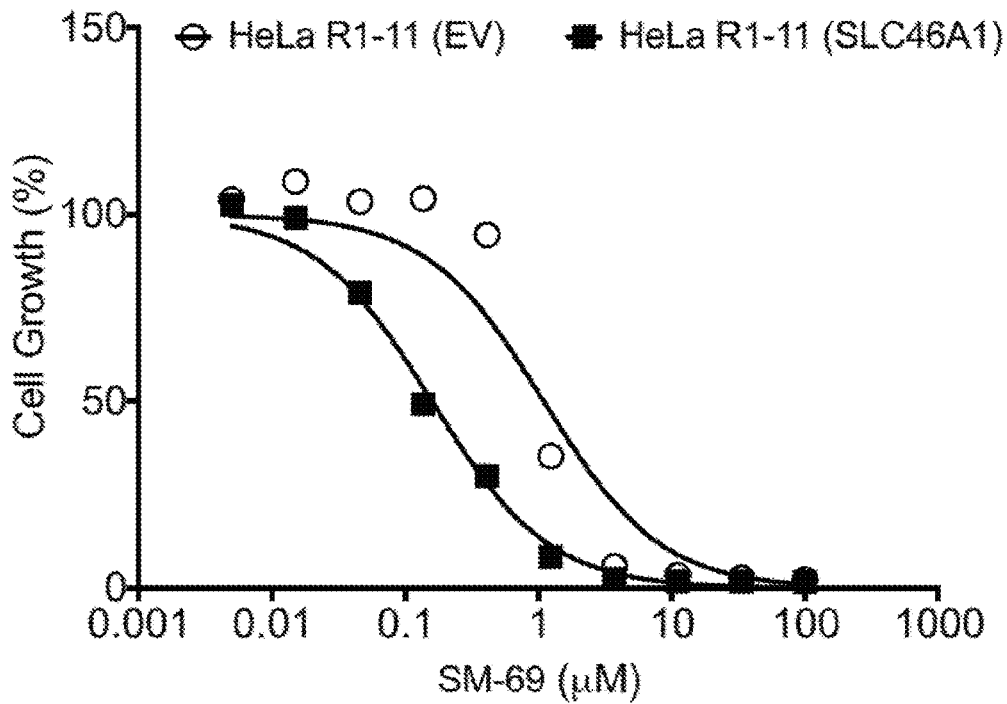
Figure 15C:
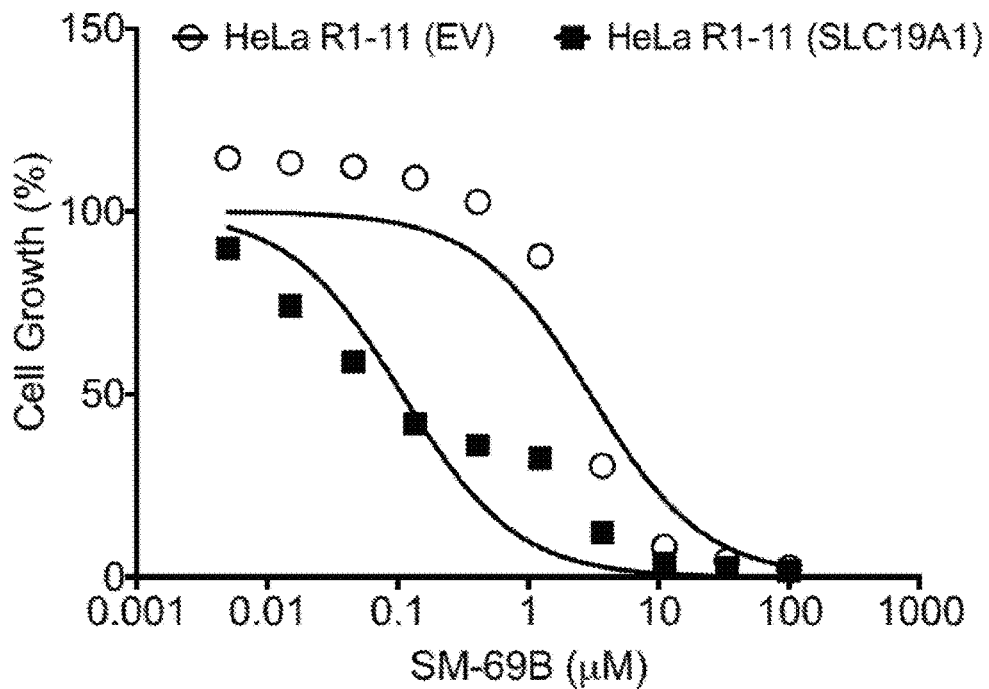
Figure 15D:
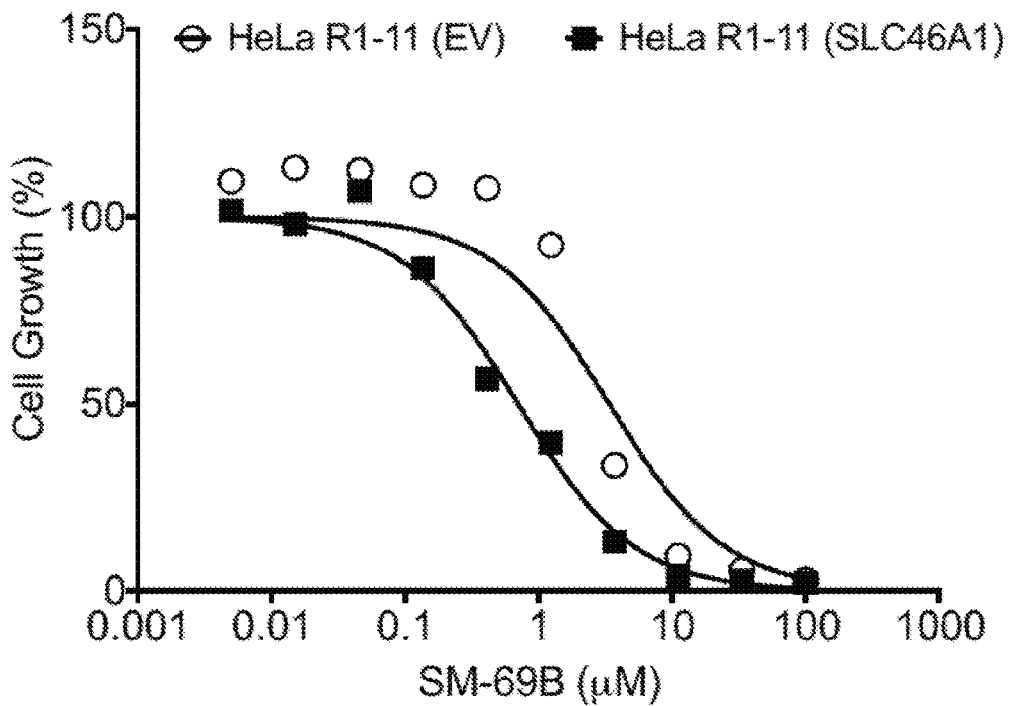

As depicted in FIGS. 8A-8B, AT-69 significantly reduces NB tumor growth relative to cisplatin and vehicle. As depicted in FIG. 13, AT-69 and AT-70 significantly increase survival in the SKNDZ xenograft model. A significant difference in survival between was observed between AT-69, AT-70 and cisplatin treated mice versus vehicle. As depicted in FIG. 8B, AT-69 significantly reduces RMS tumor growth relative to cisplatin and vehicle. As depicted in FIG. 14, AT-69 and AT-70 significantly increase survival in the RMS13 xenograft model.

The observations in this example demonstrate that AT-69 and AT-70 and cisplatin increase survival rate relative to vehicle treated mice in rhabdomyosarcoma and neuroblastoma xenograft models. AT-69 significantly increased rate of survival in RMS13 tumor bearing mice relative to cisplatin. AT-69 and AT-70 and cisplatin inhibited tumor growth in rhabdomyosarcoma and neuroblastoma xenograft models. AT-69 was observed to be more potent than cisplatin at inhibiting RMS13 and SKNDZ tumor growth.

This study provides a pharmacogenomic basis for the selection of patients based on the expression level of a particular transporter and/or enzymes involved in folate metabolism for treatment with these novel anticancer agents and moving towards individualized therapy. A net increase in the therapeutic efficacy and decrease of systemic toxicity is a desired characteristic of these anticancer compounds.

TABLE 11

The 50% growth inhibition (IC$_{50}$, in µM) of SM-69 and SM-69B in five cell lines from glioblastoma. Folic acid (1 mM) inhibits folic acid transporters, such as SLC19A1 (RFC), and reduces the potencies (increase IC$_{50}$) of SM-69 and SM-69B. The IC$_{50}$ values for SM-69 and SM-69B are comparable and are the average values from two independent experiments.

| | | IC$_{50}$ (µm) ± S.D. | | | |
|---|---|---|---|---|---|
| Cell Lines | Tumor | SM-69 | SM-69 + 1 mM Folic Acid | SM-69B | SM-69B + 1 mM Folic Acid |
| SF539 | Brain - High grade | 0.2 ± 0.007 | 13.4 ± 4.8 | 0.46 ± 0.04 | 43.2 ± 12.9 |
| SNB75 | Brain - High grade | 8.7 ± 6.4 | 46.3 ± 20.2 | 11.1 ± 2.1 | 63.3 ± 3.3 |
| U251 | Brain - High grade | 0.25 ± 0.02 | 6.1 ± 0.29 | 0.87 ± 0.13 | 18.0 ± 1.4 |
| T98G | Brain - High grade | 0.09 ± 0.007 | 1.9 ± 0.03 | 0.31 ± 0.05 | 5.3 ± 1.2 |
| U87MG | Brain - Low grade | 3.7 ± 4.5 | 26.2 ± 21.5 | 0.96 ± 0.09 | 13.9 ± 11.1 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

1. Zhao, R. et al. The proton-coupled folate transporter: impact on pemetrexed transport and on antifolates activities compared with the reduced folate carrier. Mol Pharmacol 74, 854-62 (2008). 2. Uwai, Y., Okuda, M., Takami, K., Hashimoto, Y. & Inui, K. Functional characterization of the rat multispecific organic anion transporter OAT1 mediating basolateral uptake of anionic drugs in the kidney. FEBS Lett 438, 321-4 (1998). 3. Badagnani, I. et al. Interaction of methotrexate with organic-anion transporting polypeptide 1A2 and its genetic variants. J Pharmacol Exp Ther 318, 521-9 (2006). 4. Covell, D. G., Huang, R. & Wallqvist, A. Anticancer medicines in development: assessment of bioactivity profiles within the National Cancer Institute anticancer screening data. Mol Cancer Ther 6, 2261-70 (2007). 5. More, S. S. et al. Organic cation transporters modulate the uptake and cytotoxicity of picoplatin, a third-generation platinum analogue. Mol Cancer Ther 9, 1058-69 (2010). 6. Zhang, S. et al. Organic cation transporters are determinants of oxaliplatin cytotoxicity. Cancer Res 66, 8847-57 (2006). 7. Mendelsohn, L. G. et al. The role of dietary folate in modulation of folate receptor expression, folylpolyglutamate synthetase activity and the efficacy and toxicity of lometrexol. Adv Enzyme Regul 36, 365-81 (1996). 8. Raghunathan, K., Schmitz, J. C. & Priest, D. G. Disposition of leucovorin and its metabolites in dietary folic acid-deplete mice—comparison between tumor, liver, and plasma. Cancer Chemother Pharmacol 40, 126-30 (1997). 9. Worzalla, J. F., Shih, C. & Schultz, R. M. Role of folic acid in modulating the toxicity and efficacy of the multitargeted antifolate, LY231514. Anticancer Res 18, 3235-9 (1998).

What is claimed is:

1. A compound, or a pharmaceutically acceptable salt thereof, having the formula:

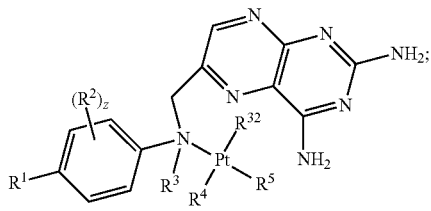

wherein $R^1$ is independently hydrogen, halogen, —$CY^1_3$, —CN, —$SR^9$, —$OSO_2R^8$, —$OSO_3H$, —$NH_2NH_2$, —$ONR^6R^7$, —$NH_2C(O)NHNH_2$, —$C(O)R^8$, —$C(O)NR^6R^7$, —$NH_2C(O)NR^6R^7$, —$NR^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently halogen, —$CY^2_3$, —CN, —$SO_qR^{10}$, —$SO_uNR^{11}R^{12}$, —$NHNH_2$, —$ONR^{11}R^{12}$, —NHC=(O)$NHNH_2$, —NHC=(O)$NR^{11}R^{12}$, —$N(O)_m$, —$NR^{11}R^{12}$, —$C(O)R^{13}$, —C(O)—$OR^{13}$, —$C(O)NR^{11}R^{12}$, —$OR^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ is an unsubstituted $C_1$-$C_4$ alkyl or H;

$R^4$, $R^5$ and $R^{32}$ are independently halogen,

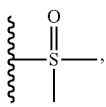

—$N_3$, —SCN, or —CN;

$R^6$, $R^7$, $R^8$, $R^9$, $R^{10}$, $R^{11}$, $R^{12}$, and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z is an integer from 0 to 4;

u is independently an integer from 1 to 2;

m is independently an integer from 1 to 2;

q is independently an integer from 0 to 4;

$Y^1$ and $Y^2$ are independently —Cl, —Br, —I, or —F.

2. The compound of claim 1, wherein $R^1$ is substituted or unsubstituted heteroalkyl.

3. The compound of claim 1, wherein $R^1$ is substituted or unsubstituted 2 to 10 membered heteroalkyl.

4. The compound of claim 1, wherein $R^1$ is substituted or unsubstituted 4 to 8 membered heteroalkyl.

5. The compound of claim 1, wherein $R^1$ is substituted with oxo, —OH, —$NH_2$, —SH, —COOH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, or unsubstituted heteroaryl.

6. The compound of claim 1, having the formula:

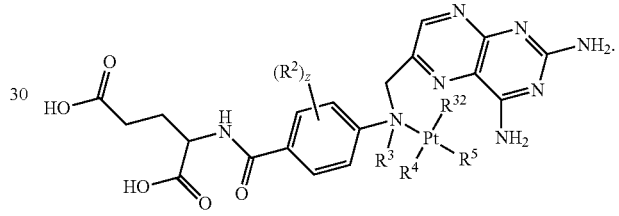

7. The compound of claim 1, wherein $R^3$ is —$CH_3$ or H.

8. The compound of claim 1, wherein $R^4$, $R^5$ and $R^{32}$ are independently halogen or

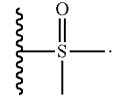

9. The compound of claim 1, wherein $R^4$, $R^5$, and $R^{32}$ are independently Cl.

10. The compound of claim 1, wherein $R^4$, $R^5$, and $R^{32}$ are independently

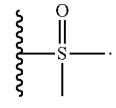

11. The compound of claim 1, wherein $R^4$ and $R^5$ are halogen and $R^{32}$ is

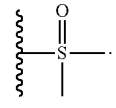

12. The compound of claim 1, wherein z is 0.

13. The compound of claim 1, having the formula:

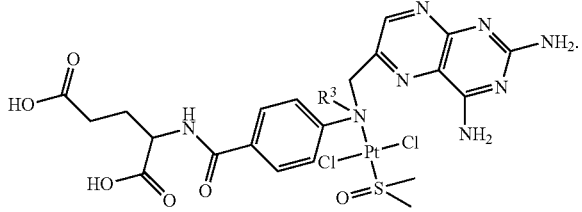

14. The compound of claim 1, having the formula:

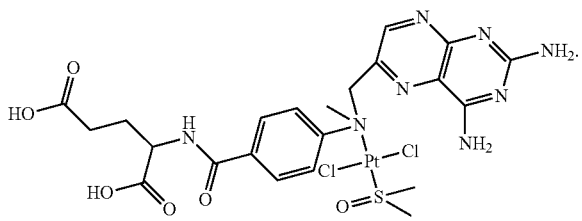

15. A pharmaceutical composition comprising a pharmaceutically acceptable excipient and a compound of claim 1, or a pharmaceutically acceptable salt thereof.

16. A method of treating cancer in a patient in need of such treatment, said method comprising administering a therapeutically effective amount of a compound of claim 1, or a pharmaceutically acceptable salt thereof, wherein said cancer is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, prostate cancer, central nervous system cancer, colon cancer, or melanoma.

17. The method of claim 16, wherein said cancer is glioblastoma, kidney cancer, neuroblastoma, rhabdomyosarcoma, osteosarcoma, colorectal cancer, liver cancer, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer.

18. The method of claim 16, wherein said cancer is osteosarcoma, neuroblastoma, or rhabdomyosarcoma.

19. The method of claim 16, wherein said cancer is breast cancer, central nervous system cancer, colon cancer, leukemia, melanoma, non-small cell lung cancer, ovarian cancer, prostate cancer, or renal cancer.

20. The method of claim 16, wherein said cancer is glioblastoma.

21. The method of claim 16, wherein the patient has cancer cells expressing a folate transporter protein a folate transporter or an organic anion transporter.

22. The method of claim 16, further comprising a method of measuring the level of a folate transporter in a sample from the patient.

23. The method of claim 22, wherein said sample comprises cancer cells.

24. The method of claim 16, wherein the compound or a pharmaceutically acceptable salt thereof binds to DNA.

25. The method of claim 16, wherein the patient has cancer cells expressing a gene involved in the folate pathway.

* * * * *

UNITED STATES PATENT AND TRADEMARK OFFICE
CERTIFICATE OF CORRECTION

PATENT NO. : 10,392,412 B2
APPLICATION NO. : 15/778213
DATED : August 27, 2019
INVENTOR(S) : Kathleen M. Giacomini et al.

It is certified that error appears in the above-identified patent and that said Letters Patent is hereby corrected as shown below:

On the Title Page

Column 1, Item (22), delete "PCT Filed: Nov. 2, 2016" and insert -- PCT Filed: Nov. 22, 2016 --, therefor.

Signed and Sealed this
Twenty-ninth Day of October, 2019

Andrei Iancu
*Director of the United States Patent and Trademark Office*